US012144854B2

(12) United States Patent
Titball et al.

(10) Patent No.: US 12,144,854 B2
(45) Date of Patent: Nov. 19, 2024

(54) EPSILON TOXIN FROM CLOSTRIDIUM PERFRINGENS AS A VACCINE

(71) Applicant: ONE HEALTH VENTURES LTD, London (GB)

(72) Inventors: Richard William Titball, Devon (GB); Monika Bokori-Brown, The Queen's Drive (GB); Helen Morcrette, The Queen's Drive (GB); Nicholas Peter Lewis, Berkshire (GB)

(73) Assignee: ONE HEALTH VENTURES LTD, London (GB)

( * ) Notice: Subject to any disclaimer, the term of this patent is extended or adjusted under 35 U.S.C. 154(b) by 0 days.

(21) Appl. No.: 16/976,869

(22) PCT Filed: Mar. 1, 2019

(86) PCT No.: PCT/GB2019/050588
§ 371 (c)(1),
(2) Date: Aug. 31, 2020

(87) PCT Pub. No.: WO2019/166830
PCT Pub. Date: Sep. 6, 2019

(65) Prior Publication Data
US 2020/0405836 A1    Dec. 31, 2020

(30) Foreign Application Priority Data
Mar. 2, 2018  (GB) ..................... 1803401
Jan. 10, 2019  (GB) ..................... 1900361

(51) Int. Cl.
A61K 39/08   (2006.01)
A61K 39/00   (2006.01)
A61P 37/06   (2006.01)
C07K 14/33   (2006.01)
C07K 16/12   (2006.01)

(52) U.S. Cl.
CPC .............. *A61K 39/08* (2013.01); *A61P 37/06* (2018.01); *C07K 14/33* (2013.01); *C07K 16/1282* (2013.01); *A61K 2039/552* (2013.01)

(58) Field of Classification Search
CPC ......... A61K 39/08; A61P 37/06; C07K 14/33; C07K 16/1282
See application file for complete search history.

(56) References Cited

U.S. PATENT DOCUMENTS

2013/0183344 A1*  7/2013  Garg ............ C07K 14/33
                                                435/6.12
2015/0064207 A1*  3/2015  Titball ............ A61K 39/08
                                                424/190.1

FOREIGN PATENT DOCUMENTS

| CN | 104560780 |   | 4/2015 | |
|---|---|---|---|---|
| CN | 104560780 A | * | 4/2015 | ............. C07K 14/33 |
| WO | 2013/144636 |   | 10/2013 | |
| WO | WO-2013144636 A1 | * | 10/2013 | ............. C07K 14/33 |
| WO | 2014/127258 |   | 8/2014 | |

OTHER PUBLICATIONS

Oyston et al. "Production of a non-toxic site-directed mutant of Clostridium perfringens epsilon-toxin which induces protective immunity in mice", Microbiology (Reading). Feb. 1998; 144 (Pt 2):333-341 (Year: 1998).*
International Search Report issued May 29, 2019 in International (PCT) Application No. PCT/GB2019/050588.
Search Report issued Oct. 31, 2018 in corresponding GB Application No. 1803401.7.
Khalili et al., "Structural pierce into molecular mechanism underlying *Clostridium perfringens* Epsilon toxin function", Toxicon, vol. 127, 2017, pp. 90-99.
Bokori-Brown et al., "Clostridium perfringens epsilon toxin H149A mutant as a platform for receptor binding studies", Protein Science, 2013, 22(5):650-659.
Rumah et al., "The Myelin and Lymphocyte Protein MAL is Required for Binding and Activity of *Clostridium perfringens* ε-Toxin", PLOS Pathogens, 11(5):e1004896, May 2015, pp. 1-29.
Yao et al., "Amino acid residue Y196E substitution and C-terminal peptide synergistically alleviate the toxicity of *Clostridium perfringens* epsilon toxin", Toxicon, vol. 100, 2015, pp. 46-52.
Jiang et al., "Identification of tyrosine 71 as a critical residue for the cytotoxic activity of *Clostridium perfringens* epsilon toxin towards MDCK cells", Journal of Microbiology, 2015, vol. 53, No. 2, pp. 141-146.

(Continued)

*Primary Examiner* — Amy E Juedes
*Assistant Examiner* — Peter Johansen
(74) *Attorney, Agent, or Firm* — Fenwick & West LLP

(57) ABSTRACT

This invention relates to methods and compositions for detecting, diagnosing, preventing, treating or ameliorating the symptoms of a demyelinating condition selected from: enterotoxemia (ET), multiple sclerosis (MS), clinically definite MS (CDMS), clinically isolated syndrome (CIS), neuromyelitis optica spectrum disorder (NMOSD), optic neuritis (ON), neuromyelitis optica (NMO), myelitis, myelitis, transverse myelitis (TM), a disease or condition characterised by the increase or presence of antibodies against aquaporin-4 (AQP-4) and/or astrocyte damage, and acute disseminated encephalomyelitis (ADEM) in a human or animal subject in need. The methods comprise administering to the subject a composition comprising an effective amount of an agent that directly or indirectly interferes with epsilon toxin (ETX) produced by *Clostridium perfringens* type B or type D bacterial strain, an ETX-binding receptor, or an interaction of ETX with its binding receptor so as to inhibit or suppress ETX modulated receptor signalling activities. The invention also provides novel polypeptides useful as a vaccine against diseases caused by or associated with the epsilon toxin of *Clostridium perfringens*.

9 Claims, 7 Drawing Sheets
Specification includes a Sequence Listing.

(56) References Cited

OTHER PUBLICATIONS

Bokori-Brown et al., "*Clostridium perfringens* epsilon toxin mutant Y30A-Y196A as a recombinant vaccine candidate against enterotoxemia", Vaccine, vol. 32, 2014, pp. 2682-2687.

Morcrette, H et al., "*Clostridium perfringens* epsilon toxin vaccine candidate lacking toxicity to cells expressing myelin and lymphocyte protein," npj Vaccines (2019) 4:32, https://doi.org/10.1038/s41541-019-0128-2.

Dorca-Arévalo et al., Correlation between in vitro cytotoxicity and in vivo lethal activity in mice of epsilon toxin mutants from Clostridium perfringens. PLOS One, 2014, 9(7): p. e102417.

Ivie and McClain, Identification of amino acids important for binding of Clostridium perfringens epsilon toxin to host cells and to HAVCRI. Biochemistry, 2012, 51(38): p. 7588-7595.

Li et al., A low-toxic site-directed mutant of Clostridium perfringens ε-toxin as a potential candidate vaccine against enterotoxemia, Human Vaccines & Immunother., 2013, 9(11): p. 2386-2392.

Sakurai et al., Histidine residues in Clostridium perfringens epsilon toxin, FEMS Microbiology Letters, 1987, 41(3): p. 317-319.

Yao et al., Immunization with a novel Clostridium perfringens epsilon toxin mutant rETXY 196E-C confers strong protection in mice, Scientific Reports, 2016; 6: 24162.

Bennett, L. et al. "Investigating the Importance of the Beta-Octyl Glucoside Binding Site for the Toxicity of C. Perfringens Epsilon Toxin," Master's Dissertation, University of Exeter, Oct. 2017, 144 pages.

\* cited by examiner

| PelB | Activated toxin | C-terminal peptide | His |
|---|---|---|---|
| 1 | 25 | H149A | 285 | 315 |

MKYLLPTAAAGLLLLAAQPAMAMGKASYDNVDTL... ...EYVIPVDKKEKS............H

↑ Periplasmic signal peptidase

↑ Trypsin

Figure 1

MKKNLVKSLAIASAVISIYSIVNIVSPTNVIAKEISNTVSNEMSKKASYDNVDTLIEKGRYNTKYNYLKR
                              -13                                 1
         30                                  72                 92
MEKYAPNAMAYFDKVTINPQGNDFYINNPKVELDGEPSMNYLEDVYFGKALLTNDTQQEQKLKSQSATCK
     Y                                      V                   F

NTDTVTATTHTVGTSIQATAKFTVPFNETGVSLTTSYSFANTNTNTNSKEITANVPSQDILVPANTTVE
                                                 149
                                                   H
       196
166
168
AIFYLKKVNVKGNVKLVGQVSGSEWGEIPSALAFPRDGYKFSLSDTVNKSDLNEDGTININGKGNYSAVM
VA

GDELIVKVRNLNTNNVQEYYIPVDKKEKSNDSNIVKYRSLYIKAPGIK

Signal sequence (1-32)
N-terminal pro-peptide (33-45)
C-terminal pro-peptide (305-328)
Mutated residues: Y30A (Y43); V72F; F92A; H129A; V166A, A168F; Y196A (Y209)

Figure 2

| Protein | Mean Tm (°C) ± SD |
|---|---|
| Wild type epsilon toxin | 67.4 ± 1.45 |
| Y30A – Y196A | 60.6 ± 0.15 |
| Y30A – Y196 – A168F | 62.0 ± 0.22 |
| Y30A – Y196A – H149A | 60.9 ± 2.28 |
| Y30A – Y196A – V166A | 59.9 ± 0.47 |
| Y30A – Y196A – V72F | 59.5 ± 0.10 |
| Y30A – Y196A – F92A | 58.2 ± 0.09 |
| Y30A – Y196A – H149A – A168F | 57.4 ± 0.02 |

Red Blood Cell Haemolysis with epsilon toxin triple mutant vaccine candidates

SEQUENCE LISTING

```
<160> NUMBER OF SEQ ID NOS: 68

<210> SEQ ID NO 1
<211> LENGTH: 26
<212> TYPE: PRT
<213> ORGANISM: Artificial Sequence
<220> FEATURE:
<223> OTHER INFORMATION: Protein fragment

<400> SEQUENCE: 1

Val Tyr Val Gly Lys Ala Leu Leu Thr Asn Asp Thr Gln Gln Glu Gln
1               5                   10                  15

Lys Leu Lys Ser Gln Ser Phe Thr Cys Lys
            20                  25

<210> SEQ ID NO 2
<211> LENGTH: 24
<212> TYPE: PRT
<213> ORGANISM: Artificial Sequence
<220> FEATURE:
<223> OTHER INFORMATION: Protein fragment

<400> SEQUENCE: 2
```

Thr His Asn Val Pro Ser Gln Asp Ile Leu Val Pro Ala Asn Thr Thr
1               5                   10                  15

Val Glu Val Ile Ala Tyr Leu Lys
                20

<210> SEQ ID NO 3
<211> LENGTH: 47
<212> TYPE: PRT
<213> ORGANISM: Artificial Sequence
<220> FEATURE:
<223> OTHER INFORMATION: Protein fragment

<400> SEQUENCE: 3

Asp Glu Leu Ile Val Lys Val Arg Asn Leu Asn Thr Asn Asn Val Gln
1               5                   10                  15

Glu Tyr Val Ile Pro Val Asp Lys Lys Glu Lys Ser Asn Asp Ser Asn
                20                  25                  30

Ile Val Lys Tyr Arg Ser Leu Tyr Ile Lys Ala Pro Gly Ile Lys
            35                  40                  45

<210> SEQ ID NO 4
<211> LENGTH: 10
<212> TYPE: PRT
<213> ORGANISM: Artificial Sequence
<220> FEATURE:
<223> OTHER INFORMATION: Protein fragment mutant
<220> FEATURE:
<221> NAME/KEY: Xaa
<222> LOCATION: (6)..(6)
<223> OTHER INFORMATION: any amino acid other than Tyr, or is a deletion

<400> SEQUENCE: 4

Arg Met Glu Lys Tyr Xaa Pro Asn Ala Met
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Protein fragment mutant
<220> FEATURE:
<221> NAME/KEY: Xaa
<222> LOCATION: (6)..(6)
<223> OTHER INFORMATION: any amino acid other than Tyr, or is a deletion

<400> SEQUENCE: 5

Gly Glu Ile Pro Ser Xaa Leu Ala Phe Pro
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Protein fragment mutant
<220> FEATURE:
<221> NAME/KEY: Xaa
<222> LOCATION: (6)..(6)
<223> OTHER INFORMATION: any amino acid other than His, or is a deletion

<400> SEQUENCE: 6

Ser Lys Glu Ile Thr Xaa Asn Val Pro Ser
1               5                   10

<210> SEQ ID NO 7

-continued

```
<211> LENGTH: 10
<212> TYPE: PRT
<213> ORGANISM: Artificial Sequence
<220> FEATURE:
<223> OTHER INFORMATION: Protein fragment mutant
<220> FEATURE:
<221> NAME/KEY: Xaa
<222> LOCATION: (6)..(6)
<223> OTHER INFORMATION: any amino acid other than Val, or is a deletion

<400> SEQUENCE: 7

Leu Glu Asp Val Tyr Xaa Gly Lys Ala Leu
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Protein fragment mutant
<220> FEATURE:
<221> NAME/KEY: Xaa
<222> LOCATION: (6)..(6)
<223> OTHER INFORMATION: any amino acid other than Phe, or is a deletion

<400> SEQUENCE: 8

Leu Lys Ser Gln Ser Xaa Thr Cys Lys Asn
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Protein fragment mutant
<220> FEATURE:
<221> NAME/KEY: Xaa
<222> LOCATION: (6)..(6)
<223> OTHER INFORMATION: any amino acid other than Val, or is a deletion

<400> SEQUENCE: 9

Asn Thr Thr Val Glu Xaa Ile Ala Tyr Leu
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Protein fragment mutant
<220> FEATURE:
<221> NAME/KEY: Xaa
<222> LOCATION: (6)..(6)
<223> OTHER INFORMATION: any amino acid other than Ala, or is a deletion

<400> SEQUENCE: 10

Thr Val Glu Val Ile Xaa Tyr Leu Lys Lys
1               5                   10

<210> SEQ ID NO 11
<211> LENGTH: 328
<212> TYPE: PRT
<213> ORGANISM: Clostridium perfringens

<400> SEQUENCE: 11

Met Lys Lys Asn Leu Val Lys Ser Leu Ala Ile Ala Ser Ala Val Ile
1               5                   10                  15

Ser Ile Tyr Ser Ile Val Asn Ile Val Ser Pro Thr Asn Val Ile Ala
            20                  25                  30
```

```
Lys Glu Ile Ser Asn Thr Val Ser Asn Glu Met Ser Lys Lys Ala Ser
                35                  40                  45

Tyr Asp Asn Val Asp Thr Leu Ile Glu Lys Gly Arg Tyr Asn Thr Lys
 50                  55                  60

Tyr Asn Tyr Leu Lys Arg Met Glu Lys Tyr Tyr Pro Asn Ala Met Ala
 65                  70                  75                  80

Tyr Phe Asp Lys Val Thr Ile Asn Pro Gln Gly Asn Asp Phe Tyr Ile
                 85                  90                  95

Asn Asn Pro Lys Val Glu Leu Asp Gly Glu Pro Ser Met Asn Tyr Leu
                100                 105                 110

Glu Asp Val Tyr Val Gly Lys Ala Leu Leu Thr Asn Asp Thr Gln Gln
                115                 120                 125

Glu Gln Lys Leu Lys Ser Gln Ser Phe Thr Cys Lys Asn Thr Asp Thr
130                 135                 140

Val Thr Ala Thr Thr His Thr Val Gly Thr Ser Ile Gln Ala Thr
145                 150                 155                 160

Ala Lys Phe Thr Val Pro Phe Asn Glu Thr Gly Val Ser Leu Thr Thr
                165                 170                 175

Ser Tyr Ser Phe Ala Asn Thr Asn Thr Asn Ser Lys Glu Ile
                180                 185                 190

Thr His Asn Val Pro Ser Gln Asp Ile Leu Val Pro Ala Asn Thr Thr
                195                 200                 205

Val Glu Val Ile Ala Tyr Leu Lys Lys Val Asn Val Lys Gly Asn Val
                210                 215                 220

Lys Leu Val Gly Gln Val Ser Gly Ser Glu Trp Gly Glu Ile Pro Ser
225                 230                 235                 240

Tyr Leu Ala Phe Pro Arg Asp Gly Tyr Lys Phe Ser Leu Ser Asp Thr
                245                 250                 255

Val Asn Lys Ser Asp Leu Asn Glu Asp Gly Thr Ile Asn Ile Asn Gly
                260                 265                 270

Lys Gly Asn Tyr Ser Ala Val Met Gly Asp Glu Leu Ile Val Lys Val
                275                 280                 285

Arg Asn Leu Asn Thr Asn Asn Val Gln Glu Tyr Val Ile Pro Val Asp
                290                 295                 300

Lys Lys Glu Lys Ser Asn Asp Ser Asn Ile Val Lys Tyr Arg Ser Leu
305                 310                 315                 320

Ser Ile Lys Ala Pro Gly Ile Lys
                325

<210> SEQ ID NO 12
<211> LENGTH: 296
<212> TYPE: PRT
<213> ORGANISM: Artificial Sequence
<220> FEATURE:
<223> OTHER INFORMATION: Construct for crystal structure analysis

<400> SEQUENCE: 12

Lys Glu Ile Ser Asn Thr Val Ser Asn Glu Met Ser Lys Lys Ala Ser
 1               5                  10                  15

Tyr Asp Asn Val Asp Thr Leu Ile Glu Lys Gly Arg Tyr Asn Thr Lys
                20                  25                  30

Tyr Asn Tyr Leu Lys Arg Met Glu Lys Tyr Tyr Pro Asn Ala Met Ala
                35                  40                  45

Tyr Phe Asp Lys Val Thr Ile Asn Pro Gln Gly Asn Asp Phe Tyr Ile
 50                  55                  60
```

Asn Asn Pro Lys Val Glu Leu Asp Gly Glu Pro Ser Met Asn Tyr Leu
65                  70                  75                  80

Glu Asp Val Tyr Val Gly Lys Ala Leu Leu Thr Asn Asp Thr Gln Gln
                85                  90                  95

Glu Gln Lys Leu Lys Ser Gln Ser Phe Thr Cys Lys Asn Thr Asp Thr
            100                 105                 110

Val Thr Ala Thr Thr His Thr Val Gly Thr Ser Ile Gln Ala Thr
        115                 120                 125

Ala Lys Phe Thr Val Pro Phe Asn Glu Thr Gly Val Ser Leu Thr Thr
    130                 135                 140

Ser Tyr Ser Phe Ala Asn Thr Asn Thr Asn Ser Lys Glu Ile
145                 150                 155                 160

Thr His Asn Val Pro Ser Gln Asp Ile Leu Val Pro Ala Asn Thr Thr
                165                 170                 175

Val Glu Val Ile Ala Tyr Leu Lys Lys Val Asn Val Lys Gly Asn Val
            180                 185                 190

Lys Leu Val Gly Gln Val Ser Gly Ser Glu Trp Gly Glu Ile Pro Ser
        195                 200                 205

Tyr Leu Ala Phe Pro Arg Asp Gly Tyr Lys Phe Ser Leu Ser Asp Thr
    210                 215                 220

Val Asn Lys Ser Asp Leu Asn Glu Asp Gly Thr Ile Asn Ile Asn Gly
225                 230                 235                 240

Lys Gly Asn Tyr Ser Ala Val Met Gly Asp Glu Leu Ile Val Lys Val
                245                 250                 255

Arg Asn Leu Asn Thr Asn Asn Val Gln Glu Tyr Val Ile Pro Val Asp
            260                 265                 270

Lys Lys Glu Lys Ser Asn Asp Ser Asn Ile Val Lys Tyr Arg Ser Leu
        275                 280                 285

Ser Ile Lys Ala Pro Gly Ile Lys
    290                 295

<210> SEQ ID NO 13
<211> LENGTH: 263
<212> TYPE: PRT
<213> ORGANISM: Clostridium perfringens

<400> SEQUENCE: 13

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Tyr
            20                  25                  30

Pro Asn Ala Met Ala Tyr Phe Asp Lys Val Thr Ile Asn Pro Gln Gly
        35                  40                  45

Asn Asp Phe Tyr Ile Asn Asn Pro Lys Val Glu Leu Asp Gly Glu Pro
    50                  55                  60

Ser Met Asn Tyr Leu Glu Asp Val Tyr Val Gly Lys Ala Leu Leu Thr
65                  70                  75                  80

Asn Asp Thr Gln Gln Glu Gln Lys Leu Lys Ser Gln Ser Phe Thr Cys
                85                  90                  95

Lys Asn Thr Asp Thr Val Thr Ala Thr Thr His Thr Val Gly Thr
            100                 105                 110

Ser Ile Gln Ala Thr Ala Lys Phe Thr Val Pro Phe Asn Glu Thr Gly
        115                 120                 125

Val Ser Leu Thr Thr Ser Tyr Ser Phe Ala Asn Thr Asn Thr Asn Thr

```
            130                 135                 140
Asn Ser Lys Glu Ile Thr His Asn Val Pro Ser Gln Asp Ile Leu Val
145                 150                 155                 160

Pro Ala Asn Thr Thr Val Glu Val Ile Ala Tyr Leu Lys Lys Val Asn
                165                 170                 175

Val Lys Gly Asn Val Lys Leu Val Gly Gln Val Ser Gly Ser Glu Trp
                180                 185                 190

Gly Glu Ile Pro Ser Tyr Leu Ala Phe Pro Arg Asp Gly Tyr Lys Phe
                195                 200                 205

Ser Leu Ser Asp Thr Val Asn Lys Ser Asp Leu Asn Glu Asp Gly Thr
            210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
                260
```

<210> SEQ ID NO 14
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 14

```
Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Tyr
                20                  25                  30

Pro Asn Ala Met Ala Tyr Phe Asp Lys Val Thr Ile Asn Pro Gln Gly
                35                  40                  45

Asn Asp Phe Tyr Ile Asn Asn Pro Lys Val Glu Leu Asp Gly Glu Pro
            50                  55                  60

Ser Met Asn Tyr Leu Glu Asp Val Tyr Val Gly Lys Ala Leu Leu Thr
65                  70                  75                  80

Asn Asp Thr Gln Gln Glu Gln Lys Leu Lys Ser Gln Ser Phe Thr Cys
                85                  90                  95

Lys Asn Thr Asp Thr Val Thr Ala Thr Thr His Thr Val Gly Thr
                100                 105                 110

Ser Ile Gln Ala Thr Ala Lys Phe Thr Val Pro Phe Asn Glu Thr Gly
            115                 120                 125

Val Ser Leu Thr Thr Ser Tyr Ser Phe Ala Asn Thr Asn Thr Asn Thr
            130                 135                 140

Asn Ser Lys Glu Ile Thr Ala Asn Val Pro Ser Gln Asp Ile Leu Val
145                 150                 155                 160

Pro Ala Asn Thr Thr Val Glu Val Ile Ala Tyr Leu Lys Lys Val Asn
                165                 170                 175

Val Lys Gly Asn Val Lys Leu Val Gly Gln Val Ser Gly Ser Glu Trp
                180                 185                 190

Gly Glu Ile Pro Ser Tyr Leu Ala Phe Pro Arg Asp Gly Tyr Lys Phe
                195                 200                 205

Ser Leu Ser Asp Thr Val Asn Lys Ser Asp Leu Asn Glu Asp Gly Thr
            210                 215                 220

Ile Asn Ile Asn Gly Lys Gly Asn Tyr Ser Ala Val Met Gly Asp Glu
```

```
                225                 230                 235                 240
Leu Ile Val Lys Val Arg Asn Leu Asn Thr Asn Asn Val Gln Glu Tyr
                245                 250                 255
Val Ile Pro Val Asp Lys Lys
                260

<210> SEQ ID NO 15
<211> LENGTH: 315
<212> TYPE: PRT
<213> ORGANISM: Artificial Sequence
<220> FEATURE:
<223> OTHER INFORMATION: Recombinant polypeptide

<400> SEQUENCE: 15

Met Lys Tyr Leu Leu Pro Thr Ala Ala Gly Leu Leu Leu Leu Ala
1               5                   10                  15

Ala Gln Pro Ala Met Ala Met Gly Lys Ala Ser Tyr Asp Asn Val Asp
                20                  25                  30

Thr Leu Ile Glu Lys Gly Arg Tyr Asn Thr Lys Tyr Asn Tyr Leu Lys
                35                  40                  45

Arg Met Glu Lys Tyr Tyr Pro Asn Ala Met Ala Tyr Phe Asp Lys Val
50                  55                  60

Thr Ile Asn Pro Gln Gly Asn Asp Phe Tyr Ile Asn Asn Pro Lys Val
65                  70                  75                  80

Glu Leu Asp Gly Glu Pro Ser Met Asn Tyr Leu Glu Asp Val Tyr Val
                85                  90                  95

Gly Lys Ala Leu Leu Thr Asn Asp Thr Gln Gln Glu Gln Lys Leu Lys
                100                 105                 110

Ser Gln Ser Phe Thr Cys Lys Asn Thr Asp Thr Val Thr Ala Thr Thr
                115                 120                 125

Thr His Thr Val Gly Thr Ser Ile Gln Ala Thr Ala Lys Phe Thr Val
                130                 135                 140

Pro Phe Asn Glu Thr Gly Val Ser Leu Thr Thr Ser Tyr Ser Phe Ala
145                 150                 155                 160

Asn Thr Asn Thr Asn Thr Asn Ser Lys Glu Ile Thr His Asn Val Pro
                165                 170                 175

Ser Gln Asp Ile Leu Val Pro Ala Asn Thr Thr Val Glu Val Ile Ala
                180                 185                 190

Tyr Leu Lys Lys Val Asn Val Lys Gly Asn Val Lys Leu Val Gly Gln
                195                 200                 205

Val Ser Gly Ser Glu Trp Gly Glu Ile Pro Ser Tyr Leu Ala Phe Pro
                210                 215                 220

Arg Asp Gly Tyr Lys Phe Ser Leu Ser Asp Thr Val Asn Lys Ser Asp
225                 230                 235                 240

Leu Asn Glu Asp Gly Thr Ile Asn Ile Asn Gly Lys Gly Asn Tyr Ser
                245                 250                 255

Ala Val Met Gly Asp Glu Leu Ile Val Lys Val Arg Asn Leu Asn Thr
                260                 265                 270

Asn Asn Val Gln Glu Tyr Val Ile Pro Val Asp Lys Lys Glu Lys Ser
                275                 280                 285

Asn Asp Ser Asn Ile Val Lys Tyr Arg Ser Leu Tyr Ile Lys Ala Pro
                290                 295                 300

Gly Ile Lys Leu Glu His His His His His
305                 310                 315
```

<210> SEQ ID NO 16
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 16

```
Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Ala
            20                  25                  30

Pro Asn Ala Met Ala Tyr Phe Asp Lys Val Thr Ile Asn Pro Gln Gly
        35                  40                  45

Asn Asp Phe Tyr Ile Asn Asn Pro Lys Val Glu Leu Asp Gly Glu Pro
    50                  55                  60

Ser Met Asn Tyr Leu Glu Asp Val Tyr Val Gly Lys Ala Leu Leu Thr
65                  70                  75                  80

Asn Asp Thr Gln Gln Glu Gln Lys Leu Lys Ser Gln Ser Phe Thr Cys
                85                  90                  95

Lys Asn Thr Asp Thr Val Thr Ala Thr Thr Thr His Thr Val Gly Thr
            100                 105                 110

Ser Ile Gln Ala Thr Ala Lys Phe Thr Val Pro Phe Asn Glu Thr Gly
        115                 120                 125

Val Ser Leu Thr Thr Ser Tyr Ser Phe Ala Asn Thr Asn Thr Asn Thr
    130                 135                 140

Asn Ser Lys Glu Ile Thr His Asn Val Pro Ser Gln Asp Ile Leu Val
145                 150                 155                 160

Pro Ala Asn Thr Thr Val Glu Val Ile Ala Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Ala Leu Ala Phe Pro Arg Asp Gly Tyr Lys Phe
        195                 200                 205

Ser Leu Ser Asp Thr Val Asn Lys Ser Asp Leu Asn Glu Asp Gly Thr
    210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Val Gln Glu Tyr
                245                 250                 255

Val Ile Pro Val Asp Lys Lys
            260
```

<210> SEQ ID NO 17
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 17

```
Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Ala
            20                  25                  30

Pro Asn Ala Met Ala Tyr Phe Asp Lys Val Thr Ile Asn Pro Gln Gly
        35                  40                  45
```

```
Asn Asp Phe Tyr Ile Asn Asn Pro Lys Val Glu Leu Asp Gly Glu Pro
        50                  55                  60

Ser Met Asn Tyr Leu Glu Asp Val Tyr Val Gly Lys Ala Leu Leu Thr
 65                  70                  75                  80

Asn Asp Thr Gln Gln Glu Gln Lys Leu Lys Ser Gln Ser Phe Thr Cys
                    85                  90                  95

Lys Asn Thr Asp Thr Val Thr Ala Thr Thr His Thr Val Gly Thr
                100                 105                 110

Ser Ile Gln Ala Thr Ala Lys Phe Thr Val Pro Phe Asn Glu Thr Gly
            115                 120                 125

Val Ser Leu Thr Thr Ser Tyr Ser Phe Ala Asn Thr Asn Thr Asn Thr
130                 135                 140

Asn Ser Lys Glu Ile Thr Ala Asn Val Pro Ser Gln Asp Ile Leu Val
145                 150                 155                 160

Pro Ala Asn Thr Thr Val Glu Val Ile Ala Tyr Leu Lys Lys Val Asn
                165                 170                 175

Val Lys Gly Asn Val Lys Leu Val Gly Gln Val Ser Gly Ser Glu Trp
                180                 185                 190

Gly Glu Ile Pro Ser Ala Leu Ala Phe Pro Arg Asp Gly Tyr Lys Phe
            195                 200                 205

Ser Leu Ser Asp Thr Val Asn Lys Ser Asp Leu Asn Glu Asp Gly Thr
210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
                260

<210> SEQ ID NO 18
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 18

Met Gly Lys Ala Ser Tyr Asp Asn Val Asp Thr Leu Ile Glu Lys Gly
 1               5                  10                  15

Arg Tyr Asn Thr Lys Tyr Asn Tyr Leu Lys Arg Met Glu Lys Tyr Ala
                20                  25                  30

Pro Asn Ala Met Ala Tyr Phe Asp Lys Val Thr Ile Asn Pro Gln Gly
            35                  40                  45

Asn Asp Phe Tyr Ile Asn Asn Pro Lys Val Glu Leu Asp Gly Glu Pro
        50                  55                  60

Ser Met Asn Tyr Leu Glu Asp Val Tyr Phe Gly Lys Ala Leu Leu Thr
 65                  70                  75                  80

Asn Asp Thr Gln Gln Glu Gln Lys Leu Lys Ser Gln Ser Phe Thr Cys
                    85                  90                  95

Lys Asn Thr Asp Thr Val Thr Ala Thr Thr Thr His Thr Val Gly Thr
                100                 105                 110

Ser Ile Gln Ala Thr Ala Lys Phe Thr Val Pro Phe Asn Glu Thr Gly
            115                 120                 125

Val Ser Leu Thr Thr Ser Tyr Ser Phe Ala Asn Thr Asn Thr Asn Thr
130                 135                 140
```

```
Asn Ser Lys Glu Ile Thr His Asn Val Pro Ser Gln Asp Ile Leu Val
145                 150                 155                 160

Pro Ala Asn Thr Thr Val Glu Val Ile Ala Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Ala Leu Ala Phe Pro Arg Asp Gly Tyr Lys Phe
        195                 200                 205

Ser Leu Ser Asp Thr Val Asn Lys Ser Asp Leu Asn Glu Asp Gly Thr
    210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
                260
```

<210> SEQ ID NO 19
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 19

```
Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Ala
                20                  25                  30

Pro Asn Ala Met Ala Tyr Phe Asp Lys Val Thr Ile Asn Pro Gln Gly
            35                  40                  45

Asn Asp Phe Tyr Ile Asn Asn Pro Lys Val Glu Leu Asp Gly Glu Pro
        50                  55                  60

Ser Met Asn Tyr Leu Glu Asp Val Tyr Val Gly Lys Ala Leu Leu Thr
65                  70                  75                  80

Asn Asp Thr Gln Gln Glu Gln Lys Leu Lys Ser Gln Ser Ala Thr Cys
                85                  90                  95

Lys Asn Thr Asp Thr Val Thr Ala Thr Thr Thr His Thr Val Gly Thr
            100                 105                 110

Ser Ile Gln Ala Thr Ala Lys Phe Thr Val Pro Phe Asn Glu Thr Gly
        115                 120                 125

Val Ser Leu Thr Thr Ser Tyr Ser Phe Ala Asn Thr Asn Thr Asn Thr
    130                 135                 140

Asn Ser Lys Glu Ile Thr His Asn Val Pro Ser Gln Asp Ile Leu Val
145                 150                 155                 160

Pro Ala Asn Thr Thr Val Glu Val Ile Ala Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Ala Leu Ala Phe Pro Arg Asp Gly Tyr Lys Phe
        195                 200                 205

Ser Leu Ser Asp Thr Val Asn Lys Ser Asp Leu Asn Glu Asp Gly Thr
    210                 215                 220

Ile Asn Ile Asn Gly Lys Gly Asn Tyr Ser Ala Val Met Gly Asp Glu
225                 230                 235                 240
```

```
Leu Ile Val Lys Val Arg Asn Leu Asn Thr Asn Asn Val Gln Glu Tyr
                245                 250                 255

Val Ile Pro Val Asp Lys Lys
            260
```

<210> SEQ ID NO 20
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 20

```
Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Ala
                20                  25                  30

Pro Asn Ala Met Ala Tyr Phe Asp Lys Val Thr Ile Asn Pro Gln Gly
            35                  40                  45

Asn Asp Phe Tyr Ile Asn Asn Pro Lys Val Glu Leu Asp Gly Glu Pro
        50                  55                  60

Ser Met Asn Tyr Leu Glu Asp Val Tyr Val Gly Lys Ala Leu Leu Thr
65                  70                  75                  80

Asn Asp Thr Gln Gln Glu Gln Lys Leu Lys Ser Gln Ser Phe Thr Cys
                85                  90                  95

Lys Asn Thr Asp Thr Val Thr Ala Thr Thr His Thr Val Gly Thr
                100                 105                 110

Ser Ile Gln Ala Thr Ala Lys Phe Thr Val Pro Phe Asn Glu Thr Gly
            115                 120                 125

Val Ser Leu Thr Thr Ser Tyr Ser Phe Ala Asn Thr Asn Thr Asn Thr
        130                 135                 140

Asn Ser Lys Glu Ile Thr His Asn Val Pro Ser Gln Asp Ile Leu Val
145                 150                 155                 160

Pro Ala Asn Thr Thr Val Glu Ala Ile Ala Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Ala Leu Ala Phe Pro Arg Asp Gly Tyr Lys Phe
        195                 200                 205

Ser Leu Ser Asp Thr Val Asn Lys Ser Asp Leu Asn Glu Asp Gly Thr
210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
            260
```

<210> SEQ ID NO 21
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 21

```
Met Gly Lys Ala Ser Tyr Asp Asn Val Asp Thr Leu Ile Glu Lys Gly
1               5                   10                  15
```

-continued

Arg Tyr Asn Thr Lys Tyr Asn Tyr Leu Lys Arg Met Glu Lys Tyr Ala
            20                  25                  30

Pro Asn Ala Met Ala Tyr Phe Asp Lys Val Thr Ile Asn Pro Gln Gly
        35                  40                  45

Asn Asp Phe Tyr Ile Asn Asn Pro Lys Val Glu Leu Asp Gly Glu Pro
    50                  55                  60

Ser Met Asn Tyr Leu Glu Asp Val Tyr Gly Lys Ala Leu Leu Thr
65                  70                  75                  80

Asn Asp Thr Gln Gln Glu Gln Lys Leu Lys Ser Gln Ser Phe Thr Cys
                85                  90                  95

Lys Asn Thr Asp Thr Val Thr Ala Thr Thr Thr His Thr Val Gly Thr
            100                 105                 110

Ser Ile Gln Ala Thr Ala Lys Phe Thr Val Pro Phe Asn Glu Thr Gly
        115                 120                 125

Val Ser Leu Thr Thr Ser Tyr Ser Phe Ala Asn Thr Asn Thr Asn Thr
130                 135                 140

Asn Ser Lys Glu Ile Thr His Asn Val Pro Ser Gln Asp Ile Leu Val
145                 150                 155                 160

Pro Ala Asn Thr Thr Val Glu Val Ile Phe Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Ala Leu Ala Phe Pro Arg Asp Gly Tyr Lys Phe
        195                 200                 205

Ser Leu Ser Asp Thr Val Asn Lys Ser Asp Leu Asn Glu Asp Gly Thr
    210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
            260

<210> SEQ ID NO 22
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 22

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Ala
            20                  25                  30

Pro Asn Ala Met Ala Tyr Phe Asp Lys Val Thr Ile Asn Pro Gln Gly
        35                  40                  45

Asn Asp Phe Tyr Ile Asn Asn Pro Lys Val Glu Leu Asp Gly Glu Pro
    50                  55                  60

Ser Met Asn Tyr Leu Glu Asp Val Tyr Phe Gly Lys Ala Leu Leu Thr
65                  70                  75                  80

Asn Asp Thr Gln Gln Glu Gln Lys Leu Lys Ser Gln Ser Phe Thr Cys
                85                  90                  95

Lys Asn Thr Asp Thr Val Thr Ala Thr Thr Thr His Thr Val Gly Thr
            100                 105                 110

Ser Ile Gln Ala Thr Ala Lys Phe Thr Val Pro Phe Asn Glu Thr Gly
            115                 120                 125

Val Ser Leu Thr Thr Ser Tyr Ser Phe Ala Asn Thr Asn Thr Asn Thr
        130                 135                 140

Asn Ser Lys Glu Ile Thr Ala Asn Val Pro Ser Gln Asp Ile Leu Val
145                 150                 155                 160

Pro Ala Asn Thr Thr Val Glu Val Ile Ala Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Ala Leu Ala Phe Pro Arg Asp Gly Tyr Lys Phe
            195                 200                 205

Ser Leu Ser Asp Thr Val Asn Lys Ser Asp Leu Asn Glu Asp Gly Thr
        210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
            260

<210> SEQ ID NO 23
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 23

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Ala
            20                  25                  30

Pro Asn Ala Met Ala Tyr Phe Asp Lys Val Thr Ile Asn Pro Gln Gly
        35                  40                  45

Asn Asp Phe Tyr Ile Asn Asn Pro Lys Val Glu Leu Asp Gly Glu Pro
50                  55                  60

Ser Met Asn Tyr Leu Glu Asp Val Tyr Val Gly Lys Ala Leu Leu Thr
65                  70                  75                  80

Asn Asp Thr Gln Gln Glu Gln Lys Leu Lys Ser Gln Ser Ala Thr Cys
                85                  90                  95

Lys Asn Thr Asp Thr Val Thr Ala Thr Thr Thr His Thr Val Gly Thr
            100                 105                 110

Ser Ile Gln Ala Thr Ala Lys Phe Thr Val Pro Phe Asn Glu Thr Gly
            115                 120                 125

Val Ser Leu Thr Thr Ser Tyr Ser Phe Ala Asn Thr Asn Thr Asn Thr
        130                 135                 140

Asn Ser Lys Glu Ile Thr Ala Asn Val Pro Ser Gln Asp Ile Leu Val
145                 150                 155                 160

Pro Ala Asn Thr Thr Val Glu Val Ile Ala Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Ala Leu Ala Phe Pro Arg Asp Gly Tyr Lys Phe
            195                 200                 205

Ser Leu Ser Asp Thr Val Asn Lys Ser Asp Leu Asn Glu Asp Gly Thr
    210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
            245                 250                 255

Val Ile Pro Val Asp Lys Lys
            260

<210> SEQ ID NO 24
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 24

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Ala
            20                  25                  30

Pro Asn Ala Met Ala Tyr Phe Asp Lys Val Thr Ile Asn Pro Gln Gly
        35                  40                  45

Asn Asp Phe Tyr Ile Asn Asn Pro Lys Val Glu Leu Asp Gly Glu Pro
    50                  55                  60

Ser Met Asn Tyr Leu Glu Asp Val Tyr Val Gly Lys Ala Leu Leu Thr
65                  70                  75                  80

Asn Asp Thr Gln Gln Glu Gln Lys Leu Lys Ser Gln Ser Phe Thr Cys
                85                  90                  95

Lys Asn Thr Asp Thr Val Thr Ala Thr Thr His Thr Val Gly Thr
            100                 105                 110

Ser Ile Gln Ala Thr Ala Lys Phe Thr Val Pro Phe Asn Glu Thr Gly
        115                 120                 125

Val Ser Leu Thr Thr Ser Tyr Ser Phe Ala Asn Thr Asn Thr Asn Thr
    130                 135                 140

Asn Ser Lys Glu Ile Thr Ala Asn Val Pro Ser Gln Asp Ile Leu Val
145                 150                 155                 160

Pro Ala Asn Thr Thr Val Glu Ala Ile Ala Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Ala Leu Ala Phe Pro Arg Asp Gly Tyr Lys Phe
        195                 200                 205

Ser Leu Ser Asp Thr Val Asn Lys Ser Asp Leu Asn Glu Asp Gly Thr
    210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
            260

<210> SEQ ID NO 25
<211> LENGTH: 263
<212> TYPE: PRT
<213> ORGANISM: Artificial Sequence

```
<220> FEATURE:
<223> OTHER INFORMATION: Mutant polypeptide

<400> SEQUENCE: 25

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Ala
                20                  25                  30

Pro Asn Ala Met Ala Tyr Phe Asp Lys Val Thr Ile Asn Pro Gln Gly
            35                  40                  45

Asn Asp Phe Tyr Ile Asn Asn Pro Lys Val Glu Leu Asp Gly Glu Pro
        50                  55                  60

Ser Met Asn Tyr Leu Glu Asp Val Tyr Val Gly Lys Ala Leu Leu Thr
65                  70                  75                  80

Asn Asp Thr Gln Gln Glu Gln Lys Leu Lys Ser Gln Ser Phe Thr Cys
                    85                  90                  95

Lys Asn Thr Asp Thr Val Thr Ala Thr Thr Thr His Thr Val Gly Thr
                100                 105                 110

Ser Ile Gln Ala Thr Ala Lys Phe Thr Val Pro Phe Asn Glu Thr Gly
            115                 120                 125

Val Ser Leu Thr Thr Ser Tyr Ser Phe Ala Asn Thr Asn Thr Asn Thr
        130                 135                 140

Asn Ser Lys Glu Ile Thr Ala Asn Val Pro Ser Gln Asp Ile Leu Val
145                 150                 155                 160

Pro Ala Asn Thr Thr Val Glu Val Ile Phe Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Ala Leu Ala Phe Pro Arg Asp Gly Tyr Lys Phe
        195                 200                 205

Ser Leu Ser Asp Thr Val Asn Lys Ser Asp Leu Asn Glu Asp Gly Thr
    210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
            260

<210> SEQ ID NO 26
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 26

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Ala
                20                  25                  30

Pro Asn Ala Met Ala Tyr Phe Asp Lys Val Thr Ile Asn Pro Gln Gly
            35                  40                  45

Asn Asp Phe Tyr Ile Asn Asn Pro Lys Val Glu Leu Asp Gly Glu Pro
        50                  55                  60

Ser Met Asn Tyr Leu Glu Asp Val Tyr Phe Gly Lys Ala Leu Leu Thr
```

```
                 65                  70                  75                  80
Asn Asp Thr Gln Gln Glu Gln Lys Leu Lys Ser Gln Ser Ala Thr Cys
                85                  90                  95

Lys Asn Thr Asp Thr Val Thr Ala Thr Thr His Thr Val Gly Thr
            100                 105                 110

Ser Ile Gln Ala Thr Ala Lys Phe Thr Val Pro Phe Asn Glu Thr Gly
            115                 120                 125

Val Ser Leu Thr Thr Ser Tyr Ser Phe Ala Asn Thr Asn Thr Asn Thr
            130                 135                 140

Asn Ser Lys Glu Ile Thr His Asn Val Pro Ser Gln Asp Ile Leu Val
145                 150                 155                 160

Pro Ala Asn Thr Thr Val Glu Val Ile Ala Tyr Leu Lys Lys Val Asn
                165                 170                 175

Val Lys Gly Asn Val Lys Leu Val Gly Gln Val Ser Gly Ser Glu Trp
                180                 185                 190

Gly Glu Ile Pro Ser Ala Leu Ala Phe Pro Arg Asp Gly Tyr Lys Phe
            195                 200                 205

Ser Leu Ser Asp Thr Val Asn Lys Ser Asp Leu Asn Glu Asp Gly Thr
            210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
                260

<210> SEQ ID NO 27
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 27

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Ala
                20                  25                  30

Pro Asn Ala Met Ala Tyr Phe Asp Lys Val Thr Ile Asn Pro Gln Gly
            35                  40                  45

Asn Asp Phe Tyr Ile Asn Asn Pro Lys Val Glu Leu Asp Gly Glu Pro
        50                  55                  60

Ser Met Asn Tyr Leu Glu Asp Val Tyr Phe Gly Lys Ala Leu Leu Thr
65                  70                  75                  80

Asn Asp Thr Gln Gln Glu Gln Lys Leu Lys Ser Gln Ser Phe Thr Cys
                85                  90                  95

Lys Asn Thr Asp Thr Val Thr Ala Thr Thr His Thr Val Gly Thr
            100                 105                 110

Ser Ile Gln Ala Thr Ala Lys Phe Thr Val Pro Phe Asn Glu Thr Gly
            115                 120                 125

Val Ser Leu Thr Thr Ser Tyr Ser Phe Ala Asn Thr Asn Thr Asn Thr
            130                 135                 140

Asn Ser Lys Glu Ile Thr His Asn Val Pro Ser Gln Asp Ile Leu Val
145                 150                 155                 160

Pro Ala Asn Thr Thr Val Glu Ala Ile Ala Tyr Leu Lys Lys Val Asn
```

```
            165                 170                 175
Val Lys Gly Asn Val Lys Leu Val Gly Gln Val Ser Gly Ser Glu Trp
            180                 185                 190

Gly Glu Ile Pro Ser Ala Leu Ala Phe Pro Arg Asp Gly Tyr Lys Phe
            195                 200                 205

Ser Leu Ser Asp Thr Val Asn Lys Ser Asp Leu Asn Glu Asp Gly Thr
            210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
                260

<210> SEQ ID NO 28
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 28

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Ala
                20                  25                  30

Pro Asn Ala Met Ala Tyr Phe Asp Lys Val Thr Ile Asn Pro Gln Gly
            35                  40                  45

Asn Asp Phe Tyr Ile Asn Asn Pro Lys Val Glu Leu Asp Gly Glu Pro
        50                  55                  60

Ser Met Asn Tyr Leu Glu Asp Val Tyr Phe Gly Lys Ala Leu Leu Thr
65                  70                  75                  80

Asn Asp Thr Gln Gln Glu Gln Lys Leu Lys Ser Gln Ser Phe Thr Cys
                85                  90                  95

Lys Asn Thr Asp Thr Val Thr Ala Thr Thr Thr His Thr Val Gly Thr
            100                 105                 110

Ser Ile Gln Ala Thr Ala Lys Phe Thr Val Pro Phe Asn Glu Thr Gly
        115                 120                 125

Val Ser Leu Thr Thr Ser Tyr Ser Phe Ala Asn Thr Asn Thr Asn Thr
    130                 135                 140

Asn Ser Lys Glu Ile Thr His Asn Val Pro Ser Gln Asp Ile Leu Val
145                 150                 155                 160

Pro Ala Asn Thr Thr Val Glu Val Ile Phe Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Ala Leu Ala Phe Pro Arg Asp Gly Tyr Lys Phe
            195                 200                 205

Ser Leu Ser Asp Thr Val Asn Lys Ser Asp Leu Asn Glu Asp Gly Thr
        210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
```

<210> SEQ ID NO 29
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 29

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Ala
            20                  25                  30

Pro Asn Ala Met Ala Tyr Phe Asp Lys Val Thr Ile Asn Pro Gln Gly
        35                  40                  45

Asn Asp Phe Tyr Ile Asn Asn Pro Lys Val Glu Leu Asp Gly Glu Pro
    50                  55                  60

Ser Met Asn Tyr Leu Glu Asp Val Tyr Val Gly Lys Ala Leu Leu Thr
65                  70                  75                  80

Asn Asp Thr Gln Gln Glu Gln Lys Leu Lys Ser Gln Ser Ala Thr Cys
                85                  90                  95

Lys Asn Thr Asp Thr Val Thr Ala Thr Thr His Thr Val Gly Thr
            100                 105                 110

Ser Ile Gln Ala Thr Ala Lys Phe Thr Val Pro Phe Asn Glu Thr Gly
        115                 120                 125

Val Ser Leu Thr Thr Ser Tyr Ser Phe Ala Asn Thr Asn Thr Asn Thr
    130                 135                 140

Asn Ser Lys Glu Ile Thr His Asn Val Pro Ser Gln Asp Ile Leu Val
145                 150                 155                 160

Pro Ala Asn Thr Thr Val Glu Ala Ile Ala Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Ala Leu Ala Phe Pro Arg Asp Gly Tyr Lys Phe
        195                 200                 205

Ser Leu Ser Asp Thr Val Asn Lys Ser Asp Leu Asn Glu Asp Gly Thr
    210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
            260

<210> SEQ ID NO 30
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 30

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Ala
            20                  25                  30

```
Pro Asn Ala Met Ala Tyr Phe Asp Lys Val Thr Ile Asn Pro Gln Gly
             35                  40                  45

Asn Asp Phe Tyr Ile Asn Asn Pro Lys Val Glu Leu Asp Gly Glu Pro
 50                  55                  60

Ser Met Asn Tyr Leu Glu Asp Val Tyr Val Gly Lys Ala Leu Leu Thr
 65                  70                  75                  80

Asn Asp Thr Gln Gln Glu Gln Lys Leu Lys Ser Gln Ser Ala Thr Cys
                 85                  90                  95

Lys Asn Thr Asp Thr Val Thr Ala Thr Thr His Thr Val Gly Thr
                100                 105                 110

Ser Ile Gln Ala Thr Ala Lys Phe Thr Val Pro Phe Asn Glu Thr Gly
             115                 120                 125

Val Ser Leu Thr Thr Ser Tyr Ser Phe Ala Asn Thr Asn Thr Asn Thr
 130                 135                 140

Asn Ser Lys Glu Ile Thr His Asn Val Pro Ser Gln Asp Ile Leu Val
 145                 150                 155                 160

Pro Ala Asn Thr Thr Val Glu Val Ile Phe Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Ala Leu Ala Phe Pro Arg Asp Gly Tyr Lys Phe
        195                 200                 205

Ser Leu Ser Asp Thr Val Asn Lys Ser Asp Leu Asn Glu Asp Gly Thr
    210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
                260

<210> SEQ ID NO 31
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 31

Met Gly Lys Ala Ser Tyr Asp Asn Val Asp Thr Leu Ile Glu Lys Gly
 1               5                  10                  15

Arg Tyr Asn Thr Lys Tyr Asn Tyr Leu Lys Arg Met Glu Lys Tyr Ala
                 20                  25                  30

Pro Asn Ala Met Ala Tyr Phe Asp Lys Val Thr Ile Asn Pro Gln Gly
             35                  40                  45

Asn Asp Phe Tyr Ile Asn Asn Pro Lys Val Glu Leu Asp Gly Glu Pro
 50                  55                  60

Ser Met Asn Tyr Leu Glu Asp Val Tyr Val Gly Lys Ala Leu Leu Thr
 65                  70                  75                  80

Asn Asp Thr Gln Gln Glu Gln Lys Leu Lys Ser Gln Ser Phe Thr Cys
                 85                  90                  95

Lys Asn Thr Asp Thr Val Thr Ala Thr Thr His Thr Val Gly Thr
                100                 105                 110

Ser Ile Gln Ala Thr Ala Lys Phe Thr Val Pro Phe Asn Glu Thr Gly
            115                 120                 125
```

Val Ser Leu Thr Thr Ser Tyr Ser Phe Ala Asn Thr Asn Thr Asn Thr
130                 135                 140

Asn Ser Lys Glu Ile Thr His Asn Val Pro Ser Gln Asp Ile Leu Val
145                 150                 155                 160

Pro Ala Asn Thr Thr Val Glu Ala Ile Phe Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Ala Leu Ala Phe Pro Arg Asp Gly Tyr Lys Phe
            195                 200                 205

Ser Leu Ser Asp Thr Val Asn Lys Ser Asp Leu Asn Glu Asp Gly Thr
210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
            260

<210> SEQ ID NO 32
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 32

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Ala
                20                  25                  30

Pro Asn Ala Met Ala Tyr Phe Asp Lys Val Thr Ile Asn Pro Gln Gly
            35                  40                  45

Asn Asp Phe Tyr Ile Asn Asn Pro Lys Val Glu Leu Asp Gly Glu Pro
    50                  55                  60

Ser Met Asn Tyr Leu Glu Asp Val Tyr Phe Gly Lys Ala Leu Leu Thr
65                  70                  75                  80

Asn Asp Thr Gln Gln Glu Gln Lys Leu Lys Ser Gln Ser Ala Thr Cys
                85                  90                  95

Lys Asn Thr Asp Thr Val Thr Ala Thr Thr Thr His Thr Val Gly Thr
            100                 105                 110

Ser Ile Gln Ala Thr Ala Lys Phe Thr Val Pro Phe Asn Glu Thr Gly
        115                 120                 125

Val Ser Leu Thr Thr Ser Tyr Ser Phe Ala Asn Thr Asn Thr Asn Thr
130                 135                 140

Asn Ser Lys Glu Ile Thr Ala Asn Val Pro Ser Gln Asp Ile Leu Val
145                 150                 155                 160

Pro Ala Asn Thr Thr Val Glu Val Ile Ala Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Ala Leu Ala Phe Pro Arg Asp Gly Tyr Lys Phe
            195                 200                 205

Ser Leu Ser Asp Thr Val Asn Lys Ser Asp Leu Asn Glu Asp Gly Thr
210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
            245                 250                 255

Val Ile Pro Val Asp Lys Lys
            260

<210> SEQ ID NO 33
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 33

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Ala
            20                  25                  30

Pro Asn Ala Met Ala Tyr Phe Asp Lys Val Thr Ile Asn Pro Gln Gly
            35                  40                  45

Asn Asp Phe Tyr Ile Asn Asn Pro Lys Val Glu Leu Asp Gly Glu Pro
50                  55                  60

Ser Met Asn Tyr Leu Glu Asp Val Tyr Phe Gly Lys Ala Leu Leu Thr
65                  70                  75                  80

Asn Asp Thr Gln Gln Glu Gln Lys Leu Lys Ser Gln Ser Phe Thr Cys
            85                  90                  95

Lys Asn Thr Asp Thr Val Thr Ala Thr Thr His Thr Val Gly Thr
            100                 105                 110

Ser Ile Gln Ala Thr Ala Lys Phe Thr Val Pro Phe Asn Glu Thr Gly
            115                 120                 125

Val Ser Leu Thr Thr Ser Tyr Ser Phe Ala Asn Thr Asn Thr Asn Thr
130                 135                 140

Asn Ser Lys Glu Ile Thr Ala Asn Val Pro Ser Gln Asp Ile Leu Val
145                 150                 155                 160

Pro Ala Asn Thr Thr Val Glu Ala Ile Ala Tyr Leu Lys Lys Val Asn
            165                 170                 175

Val Lys Gly Asn Val Lys Leu Val Gly Gln Val Ser Gly Ser Glu Trp
            180                 185                 190

Gly Glu Ile Pro Ser Ala Leu Ala Phe Pro Arg Asp Gly Tyr Lys Phe
            195                 200                 205

Ser Leu Ser Asp Thr Val Asn Lys Ser Asp Leu Asn Glu Asp Gly Thr
210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
            245                 250                 255

Val Ile Pro Val Asp Lys Lys
            260

<210> SEQ ID NO 34
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 34

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Ala
            20                  25                  30

Pro Asn Ala Met Ala Tyr Phe Asp Lys Val Thr Ile Asn Pro Gln Gly
        35                  40                  45

Asn Asp Phe Tyr Ile Asn Asn Pro Lys Val Glu Leu Asp Gly Glu Pro
    50                  55                  60

Ser Met Asn Tyr Leu Glu Asp Val Tyr Phe Gly Lys Ala Leu Leu Thr
65                  70                  75                  80

Asn Asp Thr Gln Gln Glu Gln Lys Leu Lys Ser Gln Ser Phe Thr Cys
                85                  90                  95

Lys Asn Thr Asp Thr Val Thr Ala Thr Thr Thr His Thr Val Gly Thr
                100                 105                 110

Ser Ile Gln Ala Thr Ala Lys Phe Thr Val Pro Phe Asn Glu Thr Gly
            115                 120                 125

Val Ser Leu Thr Thr Ser Tyr Ser Phe Ala Asn Thr Asn Thr Asn Thr
        130                 135                 140

Asn Ser Lys Glu Ile Thr Ala Asn Val Pro Ser Gln Asp Ile Leu Val
145                 150                 155                 160

Pro Ala Asn Thr Thr Val Glu Val Ile Phe Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Ala Leu Ala Phe Pro Arg Asp Gly Tyr Lys Phe
        195                 200                 205

Ser Leu Ser Asp Thr Val Asn Lys Ser Asp Leu Asn Glu Asp Gly Thr
    210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
            260

<210> SEQ ID NO 35
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 35

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Ala
            20                  25                  30

Pro Asn Ala Met Ala Tyr Phe Asp Lys Val Thr Ile Asn Pro Gln Gly
        35                  40                  45

Asn Asp Phe Tyr Ile Asn Asn Pro Lys Val Glu Leu Asp Gly Glu Pro
    50                  55                  60

Ser Met Asn Tyr Leu Glu Asp Val Tyr Val Gly Lys Ala Leu Leu Thr
65                  70                  75                  80

Asn Asp Thr Gln Gln Glu Gln Lys Leu Lys Ser Gln Ser Ala Thr Cys
                85                  90                  95

Lys Asn Thr Asp Thr Val Thr Ala Thr Thr His Thr Val Gly Thr
            100                 105                 110

Ser Ile Gln Ala Thr Ala Lys Phe Thr Val Pro Phe Asn Glu Thr Gly
        115                 120                 125

Val Ser Leu Thr Thr Ser Tyr Ser Phe Ala Asn Thr Asn Thr Asn Thr
130                 135                 140

Asn Ser Lys Glu Ile Thr Ala Asn Val Pro Ser Gln Asp Ile Leu Val
145                 150                 155                 160

Pro Ala Asn Thr Thr Val Glu Ala Ile Ala Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Ala Leu Ala Phe Pro Arg Asp Gly Tyr Lys Phe
            195                 200                 205

Ser Leu Ser Asp Thr Val Asn Lys Ser Asp Leu Asn Glu Asp Gly Thr
        210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
            260

<210> SEQ ID NO 36
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 36

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Ala
            20                  25                  30

Pro Asn Ala Met Ala Tyr Phe Asp Lys Val Thr Ile Asn Pro Gln Gly
        35                  40                  45

Asn Asp Phe Tyr Ile Asn Asn Pro Lys Val Glu Leu Asp Gly Glu Pro
    50                  55                  60

Ser Met Asn Tyr Leu Glu Asp Val Tyr Val Gly Lys Ala Leu Leu Thr
65                  70                  75                  80

Asn Asp Thr Gln Gln Glu Gln Lys Leu Lys Ser Gln Ser Ala Thr Cys
                85                  90                  95

Lys Asn Thr Asp Thr Val Thr Ala Thr Thr His Thr Val Gly Thr
            100                 105                 110

Ser Ile Gln Ala Thr Ala Lys Phe Thr Val Pro Phe Asn Glu Thr Gly
        115                 120                 125

Val Ser Leu Thr Thr Ser Tyr Ser Phe Ala Asn Thr Asn Thr Asn Thr
130                 135                 140

Asn Ser Lys Glu Ile Thr Ala Asn Val Pro Ser Gln Asp Ile Leu Val
145                 150                 155                 160

Pro Ala Asn Thr Thr Val Glu Val Ile Phe Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Ala Leu Ala Phe Pro Arg Asp Gly Tyr Lys Phe
            195                 200                 205

Ser Leu Ser Asp Thr Val Asn Lys Ser Asp Leu Asn Glu Asp Gly Thr
    210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
            260

<210> SEQ ID NO 37
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 37

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Ala
            20                  25                  30

Pro Asn Ala Met Ala Tyr Phe Asp Lys Val Thr Ile Asn Pro Gln Gly
        35                  40                  45

Asn Asp Phe Tyr Ile Asn Asn Pro Lys Val Glu Leu Asp Gly Glu Pro
    50                  55                  60

Ser Met Asn Tyr Leu Glu Asp Val Tyr Val Gly Lys Ala Leu Leu Thr
65                  70                  75                  80

Asn Asp Thr Gln Gln Glu Gln Lys Leu Lys Ser Gln Ser Phe Thr Cys
                85                  90                  95

Lys Asn Thr Asp Thr Val Thr Ala Thr Thr Thr His Thr Val Gly Thr
            100                 105                 110

Ser Ile Gln Ala Thr Ala Lys Phe Thr Val Pro Phe Asn Glu Thr Gly
        115                 120                 125

Val Ser Leu Thr Thr Ser Tyr Ser Phe Ala Asn Thr Asn Thr Asn Thr
    130                 135                 140

Asn Ser Lys Glu Ile Thr Ala Asn Val Pro Ser Gln Asp Ile Leu Val
145                 150                 155                 160

Pro Ala Asn Thr Thr Val Glu Ala Ile Phe Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Ala Leu Ala Phe Pro Arg Asp Gly Tyr Lys Phe
        195                 200                 205

Ser Leu Ser Asp Thr Val Asn Lys Ser Asp Leu Asn Glu Asp Gly Thr
    210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
            260

<210> SEQ ID NO 38

```
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 38

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Ala
            20                  25                  30

Pro Asn Ala Met Ala Tyr Phe Asp Lys Val Thr Ile Asn Pro Gln Gly
        35                  40                  45

Asn Asp Phe Tyr Ile Asn Asn Pro Lys Val Glu Leu Asp Gly Glu Pro
    50                  55                  60

Ser Met Asn Tyr Leu Glu Asp Val Tyr Phe Gly Lys Ala Leu Leu Thr
65                  70                  75                  80

Asn Asp Thr Gln Gln Glu Gln Lys Leu Lys Ser Gln Ser Ala Thr Cys
                85                  90                  95

Lys Asn Thr Asp Thr Val Thr Ala Thr Thr Thr His Thr Val Gly Thr
            100                 105                 110

Ser Ile Gln Ala Thr Ala Lys Phe Thr Val Pro Phe Asn Glu Thr Gly
        115                 120                 125

Val Ser Leu Thr Thr Ser Tyr Ser Phe Ala Asn Thr Asn Thr Asn Thr
    130                 135                 140

Asn Ser Lys Glu Ile Thr His Asn Val Pro Ser Gln Asp Ile Leu Val
145                 150                 155                 160

Pro Ala Asn Thr Thr Val Glu Ala Ile Ala Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Ala Leu Ala Phe Pro Arg Asp Gly Tyr Lys Phe
        195                 200                 205

Ser Leu Ser Asp Thr Val Asn Lys Ser Asp Leu Asn Glu Asp Gly Thr
    210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
            260

<210> SEQ ID NO 39
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 39

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Ala
            20                  25                  30

Pro Asn Ala Met Ala Tyr Phe Asp Lys Val Thr Ile Asn Pro Gln Gly
        35                  40                  45

Asn Asp Phe Tyr Ile Asn Asn Pro Lys Val Glu Leu Asp Gly Glu Pro
```

```
                50                  55                  60
Ser Met Asn Tyr Leu Glu Asp Val Tyr Phe Gly Lys Ala Leu Leu Thr
 65                  70                  75                  80

Asn Asp Thr Gln Gln Glu Gln Lys Leu Lys Ser Gln Ser Ala Thr Cys
                 85                  90                  95

Lys Asn Thr Asp Thr Val Thr Ala Thr Thr His Thr Val Gly Thr
                100                 105                 110

Ser Ile Gln Ala Thr Ala Lys Phe Thr Val Pro Phe Asn Glu Thr Gly
                115                 120                 125

Val Ser Leu Thr Thr Ser Tyr Ser Phe Ala Asn Thr Asn Thr Asn Thr
                130                 135                 140

Asn Ser Lys Glu Ile Thr His Asn Val Pro Ser Gln Asp Ile Leu Val
145                 150                 155                 160

Pro Ala Asn Thr Thr Val Glu Val Ile Phe Tyr Leu Lys Lys Val Asn
                165                 170                 175

Val Lys Gly Asn Val Lys Leu Val Gly Gln Val Ser Gly Ser Glu Trp
                180                 185                 190

Gly Glu Ile Pro Ser Ala Leu Ala Phe Pro Arg Asp Gly Tyr Lys Phe
                195                 200                 205

Ser Leu Ser Asp Thr Val Asn Lys Ser Asp Leu Asn Glu Asp Gly Thr
                210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
                260

<210> SEQ ID NO 40
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 40

Met Gly Lys Ala Ser Tyr Asp Asn Val Asp Thr Leu Ile Glu Lys Gly
 1               5                  10                  15

Arg Tyr Asn Thr Lys Tyr Asn Tyr Leu Lys Arg Met Glu Lys Tyr Ala
                 20                  25                  30

Pro Asn Ala Met Ala Tyr Phe Asp Lys Val Thr Ile Asn Pro Gln Gly
                 35                  40                  45

Asn Asp Phe Tyr Ile Asn Asn Pro Lys Val Glu Leu Asp Gly Glu Pro
                 50                  55                  60

Ser Met Asn Tyr Leu Glu Asp Val Tyr Phe Gly Lys Ala Leu Leu Thr
 65                  70                  75                  80

Asn Asp Thr Gln Gln Glu Gln Lys Leu Lys Ser Gln Ser Phe Thr Cys
                 85                  90                  95

Lys Asn Thr Asp Thr Val Thr Ala Thr Thr His Thr Val Gly Thr
                100                 105                 110

Ser Ile Gln Ala Thr Ala Lys Phe Thr Val Pro Phe Asn Glu Thr Gly
                115                 120                 125

Val Ser Leu Thr Thr Ser Tyr Ser Phe Ala Asn Thr Asn Thr Asn Thr
                130                 135                 140

Asn Ser Lys Glu Ile Thr His Asn Val Pro Ser Gln Asp Ile Leu Val
```

```
145                 150                 155                 160
Pro Ala Asn Thr Thr Val Glu Ala Ile Phe Tyr Leu Lys Lys Val Asn
                165                 170                 175

Val Lys Gly Asn Val Lys Leu Val Gly Gln Val Ser Gly Ser Glu Trp
                180                 185                 190

Gly Glu Ile Pro Ser Ala Leu Ala Phe Pro Arg Asp Gly Tyr Lys Phe
                195                 200                 205

Ser Leu Ser Asp Thr Val Asn Lys Ser Asp Leu Asn Glu Asp Gly Thr
                210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
                260

<210> SEQ ID NO 41
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 41

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Ala
                20                  25                  30

Pro Asn Ala Met Ala Tyr Phe Asp Lys Val Thr Ile Asn Pro Gln Gly
                35                  40                  45

Asn Asp Phe Tyr Ile Asn Asn Pro Lys Val Glu Leu Asp Gly Glu Pro
            50                  55                  60

Ser Met Asn Tyr Leu Glu Asp Val Tyr Val Gly Lys Ala Leu Leu Thr
65              70                  75                  80

Asn Asp Thr Gln Gln Glu Gln Lys Leu Lys Ser Gln Ser Ala Thr Cys
                85                  90                  95

Lys Asn Thr Asp Thr Val Thr Ala Thr Thr His Thr Val Gly Thr
                100                 105                 110

Ser Ile Gln Ala Thr Ala Lys Phe Thr Val Pro Phe Asn Glu Thr Gly
                115                 120                 125

Val Ser Leu Thr Thr Ser Tyr Ser Phe Ala Asn Thr Asn Thr Asn Thr
                130                 135                 140

Asn Ser Lys Glu Ile Thr His Asn Val Pro Ser Gln Asp Ile Leu Val
145                 150                 155                 160

Pro Ala Asn Thr Thr Val Glu Ala Ile Phe Tyr Leu Lys Lys Val Asn
                165                 170                 175

Val Lys Gly Asn Val Lys Leu Val Gly Gln Val Ser Gly Ser Glu Trp
                180                 185                 190

Gly Glu Ile Pro Ser Ala Leu Ala Phe Pro Arg Asp Gly Tyr Lys Phe
                195                 200                 205

Ser Leu Ser Asp Thr Val Asn Lys Ser Asp Leu Asn Glu Asp Gly Thr
                210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
```

```
                        245                 250                 255
Val Ile Pro Val Asp Lys Lys
            260

<210> SEQ ID NO 42
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 42

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Ala
                20                  25                  30

Pro Asn Ala Met Ala Tyr Phe Asp Lys Val Thr Ile Asn Pro Gln Gly
            35                  40                  45

Asn Asp Phe Tyr Ile Asn Asn Pro Lys Val Glu Leu Asp Gly Glu Pro
        50                  55                  60

Ser Met Asn Tyr Leu Glu Asp Val Tyr Phe Gly Lys Ala Leu Leu Thr
65                  70                  75                  80

Asn Asp Thr Gln Gln Glu Gln Lys Leu Lys Ser Gln Ser Ala Thr Cys
                85                  90                  95

Lys Asn Thr Asp Thr Val Thr Ala Thr Thr His Thr Val Gly Thr
            100                 105                 110

Ser Ile Gln Ala Thr Ala Lys Phe Thr Val Pro Phe Asn Glu Thr Gly
        115                 120                 125

Val Ser Leu Thr Thr Ser Tyr Ser Phe Ala Asn Thr Asn Thr Asn Thr
    130                 135                 140

Asn Ser Lys Glu Ile Thr Ala Asn Val Pro Ser Gln Asp Ile Leu Val
145                 150                 155                 160

Pro Ala Asn Thr Thr Val Glu Ala Ile Ala Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Ala Leu Ala Phe Pro Arg Asp Gly Tyr Lys Phe
        195                 200                 205

Ser Leu Ser Asp Thr Val Asn Lys Ser Asp Leu Asn Glu Asp Gly Thr
    210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
            260

<210> SEQ ID NO 43
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 43

Met Gly Lys Ala Ser Tyr Asp Asn Val Asp Thr Leu Ile Glu Lys Gly
1               5                   10                  15
```

Arg Tyr Asn Thr Lys Tyr Asn Tyr Leu Lys Arg Met Glu Lys Tyr Ala
            20                  25                  30

Pro Asn Ala Met Ala Tyr Phe Asp Lys Val Thr Ile Asn Pro Gln Gly
            35                  40                  45

Asn Asp Phe Tyr Ile Asn Asn Pro Lys Val Glu Leu Asp Gly Glu Pro
 50                  55                  60

Ser Met Asn Tyr Leu Glu Asp Val Tyr Phe Gly Lys Ala Leu Leu Thr
 65                  70                  75                  80

Asn Asp Thr Gln Gln Glu Gln Lys Leu Lys Ser Gln Ser Ala Thr Cys
            85                  90                  95

Lys Asn Thr Asp Thr Val Thr Ala Thr Thr Thr His Thr Val Gly Thr
            100                 105                 110

Ser Ile Gln Ala Thr Ala Lys Phe Thr Val Pro Phe Asn Glu Thr Gly
            115                 120                 125

Val Ser Leu Thr Thr Ser Tyr Ser Phe Ala Asn Thr Asn Thr Asn Thr
            130                 135                 140

Asn Ser Lys Glu Ile Thr Ala Asn Val Pro Ser Gln Asp Ile Leu Val
145                 150                 155                 160

Pro Ala Asn Thr Thr Val Glu Val Ile Phe Tyr Leu Lys Lys Val Asn
            165                 170                 175

Val Lys Gly Asn Val Lys Leu Val Gly Gln Val Ser Gly Ser Glu Trp
            180                 185                 190

Gly Glu Ile Pro Ser Ala Leu Ala Phe Pro Arg Asp Gly Tyr Lys Phe
            195                 200                 205

Ser Leu Ser Asp Thr Val Asn Lys Ser Asp Leu Asn Glu Asp Gly Thr
 210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
            245                 250                 255

Val Ile Pro Val Asp Lys Lys
            260

<210> SEQ ID NO 44
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 44

Met Gly Lys Ala Ser Tyr Asp Asn Val Asp Thr Leu Ile Glu Lys Gly
 1                   5                  10                  15

Arg Tyr Asn Thr Lys Tyr Asn Tyr Leu Lys Arg Met Glu Lys Tyr Ala
            20                  25                  30

Pro Asn Ala Met Ala Tyr Phe Asp Lys Val Thr Ile Asn Pro Gln Gly
            35                  40                  45

Asn Asp Phe Tyr Ile Asn Asn Pro Lys Val Glu Leu Asp Gly Glu Pro
 50                  55                  60

Ser Met Asn Tyr Leu Glu Asp Val Tyr Phe Gly Lys Ala Leu Leu Thr
 65                  70                  75                  80

Asn Asp Thr Gln Gln Glu Gln Lys Leu Lys Ser Gln Ser Ala Thr Cys
            85                  90                  95

Lys Asn Thr Asp Thr Val Thr Ala Thr Thr Thr His Thr Val Gly Thr
            100                 105                 110

```
Ser Ile Gln Ala Thr Ala Lys Phe Thr Val Pro Phe Asn Glu Thr Gly
        115                 120                 125

Val Ser Leu Thr Thr Ser Tyr Ser Phe Ala Asn Thr Asn Thr Asn Thr
130                 135                 140

Asn Ser Lys Glu Ile Thr His Asn Val Pro Ser Gln Asp Ile Leu Val
145                 150                 155                 160

Pro Ala Asn Thr Thr Val Glu Ala Ile Phe Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Ala Leu Ala Phe Pro Arg Asp Gly Tyr Lys Phe
        195                 200                 205

Ser Leu Ser Asp Thr Val Asn Lys Ser Asp Leu Asn Glu Asp Gly Thr
210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
            260

<210> SEQ ID NO 45
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 45

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Ala
            20                  25                  30

Pro Asn Ala Met Ala Tyr Phe Asp Lys Val Thr Ile Asn Pro Gln Gly
        35                  40                  45

Asn Asp Phe Tyr Ile Asn Asn Pro Lys Val Glu Leu Asp Gly Glu Pro
    50                  55                  60

Ser Met Asn Tyr Leu Glu Asp Val Tyr Phe Gly Lys Ala Leu Leu Thr
65                  70                  75                  80

Asn Asp Thr Gln Gln Glu Gln Lys Leu Lys Ser Gln Ser Ala Thr Cys
                85                  90                  95

Lys Asn Thr Asp Thr Val Thr Ala Thr Thr His Thr Val Gly Thr
            100                 105                 110

Ser Ile Gln Ala Thr Ala Lys Phe Thr Val Pro Phe Asn Glu Thr Gly
        115                 120                 125

Val Ser Leu Thr Thr Ser Tyr Ser Phe Ala Asn Thr Asn Thr Asn Thr
130                 135                 140

Asn Ser Lys Glu Ile Thr Ala Asn Val Pro Ser Gln Asp Ile Leu Val
145                 150                 155                 160

Pro Ala Asn Thr Thr Val Glu Ala Ile Phe Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Ala Leu Ala Phe Pro Arg Asp Gly Tyr Lys Phe
        195                 200                 205
```

```
Ser Leu Ser Asp Thr Val Asn Lys Ser Asp Leu Asn Glu Asp Gly Thr
        210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
            260

<210> SEQ ID NO 46
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 46

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Tyr
            20                  25                  30

Pro Asn Ala Met Ala Tyr Phe Asp Lys Val Thr Ile Asn Pro Gln Gly
        35                  40                  45

Asn Asp Phe Tyr Ile Asn Asn Pro Lys Val Glu Leu Asp Gly Glu Pro
    50                  55                  60

Ser Met Asn Tyr Leu Glu Asp Val Tyr Phe Gly Lys Ala Leu Leu Thr
65                  70                  75                  80

Asn Asp Thr Gln Gln Glu Gln Lys Leu Lys Ser Gln Ser Phe Thr Cys
                85                  90                  95

Lys Asn Thr Asp Thr Val Thr Ala Thr Thr Thr His Thr Val Gly Thr
            100                 105                 110

Ser Ile Gln Ala Thr Ala Lys Phe Thr Val Pro Phe Asn Glu Thr Gly
        115                 120                 125

Val Ser Leu Thr Thr Ser Tyr Ser Phe Ala Asn Thr Asn Thr Asn Thr
    130                 135                 140

Asn Ser Lys Glu Ile Thr His Asn Val Pro Ser Gln Asp Ile Leu Val
145                 150                 155                 160

Pro Ala Asn Thr Thr Val Glu Val Ile Ala Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Tyr Leu Ala Phe Pro Arg Asp Gly Tyr Lys Phe
        195                 200                 205

Ser Leu Ser Asp Thr Val Asn Lys Ser Asp Leu Asn Glu Asp Gly Thr
    210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
            260

<210> SEQ ID NO 47
<211> LENGTH: 263
<212> TYPE: PRT
<213> ORGANISM: Artificial Sequence
<220> FEATURE:
```

<223> OTHER INFORMATION: Mutant polypeptide

<400> SEQUENCE: 47

```
Met Gly Lys Ala Ser Tyr Asp Asn Val Asp Thr Leu Ile Glu Lys Gly
1               5                   10                  15
Arg Tyr Asn Thr Lys Tyr Asn Tyr Leu Lys Arg Met Glu Lys Tyr Tyr
            20                  25                  30
Pro Asn Ala Met Ala Tyr Phe Asp Lys Val Thr Ile Asn Pro Gln Gly
        35                  40                  45
Asn Asp Phe Tyr Ile Asn Asn Pro Lys Val Glu Leu Asp Gly Glu Pro
    50                  55                  60
Ser Met Asn Tyr Leu Glu Asp Val Tyr Val Gly Lys Ala Leu Leu Thr
65                  70                  75                  80
Asn Asp Thr Gln Gln Glu Gln Lys Leu Lys Ser Gln Ser Ala Thr Cys
                85                  90                  95
Lys Asn Thr Asp Thr Val Thr Ala Thr Thr Thr His Thr Val Gly Thr
            100                 105                 110
Ser Ile Gln Ala Thr Ala Lys Phe Thr Val Pro Phe Asn Glu Thr Gly
        115                 120                 125
Val Ser Leu Thr Thr Ser Tyr Ser Phe Ala Asn Thr Asn Thr Asn Thr
    130                 135                 140
Asn Ser Lys Glu Ile Thr His Asn Val Pro Ser Gln Asp Ile Leu Val
145                 150                 155                 160
Pro Ala Asn Thr Thr Val Glu Val Ile Ala Tyr Leu Lys Lys Val Asn
                165                 170                 175
Val Lys Gly Asn Val Lys Leu Val Gly Gln Val Ser Gly Ser Glu Trp
            180                 185                 190
Gly Glu Ile Pro Ser Tyr Leu Ala Phe Pro Arg Asp Gly Tyr Lys Phe
        195                 200                 205
Ser Leu Ser Asp Thr Val Asn Lys Ser Asp Leu Asn Glu Asp Gly Thr
    210                 215                 220
Ile Asn Ile Asn Gly Lys Gly Asn Tyr Ser Ala Val Met Gly Asp Glu
225                 230                 235                 240
Leu Ile Val Lys Val Arg Asn Leu Asn Thr Asn Asn Val Gln Glu Tyr
                245                 250                 255
Val Ile Pro Val Asp Lys Lys
            260
```

<210> SEQ ID NO 48
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 48

```
Met Gly Lys Ala Ser Tyr Asp Asn Val Asp Thr Leu Ile Glu Lys Gly
1               5                   10                  15
Arg Tyr Asn Thr Lys Tyr Asn Tyr Leu Lys Arg Met Glu Lys Tyr Tyr
            20                  25                  30
Pro Asn Ala Met Ala Tyr Phe Asp Lys Val Thr Ile Asn Pro Gln Gly
        35                  40                  45
Asn Asp Phe Tyr Ile Asn Asn Pro Lys Val Glu Leu Asp Gly Glu Pro
    50                  55                  60
Ser Met Asn Tyr Leu Glu Asp Val Tyr Val Gly Lys Ala Leu Leu Thr
65                  70                  75                  80
```

```
Asn Asp Thr Gln Gln Glu Gln Lys Leu Lys Ser Gln Ser Phe Thr Cys
                85                  90                  95

Lys Asn Thr Asp Thr Val Thr Ala Thr Thr His Thr Val Gly Thr
            100                 105                 110

Ser Ile Gln Ala Thr Ala Lys Phe Thr Val Pro Phe Asn Glu Thr Gly
        115                 120                 125

Val Ser Leu Thr Thr Ser Tyr Ser Phe Ala Asn Thr Asn Thr Asn Thr
130                 135                 140

Asn Ser Lys Glu Ile Thr Ala Asn Val Pro Ser Gln Asp Ile Leu Val
145                 150                 155                 160

Pro Ala Asn Thr Thr Val Glu Val Ile Ala Tyr Leu Lys Lys Val Asn
                165                 170                 175

Val Lys Gly Asn Val Lys Leu Val Gly Gln Val Ser Gly Ser Glu Trp
                180                 185                 190

Gly Glu Ile Pro Ser Tyr Leu Ala Phe Pro Arg Asp Gly Tyr Lys Phe
                195                 200                 205

Ser Leu Ser Asp Thr Val Asn Lys Ser Asp Leu Asn Glu Asp Gly Thr
        210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
                260

<210> SEQ ID NO 49
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 49

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Tyr
                20                  25                  30

Pro Asn Ala Met Ala Tyr Phe Asp Lys Val Thr Ile Asn Pro Gln Gly
            35                  40                  45

Asn Asp Phe Tyr Ile Asn Asn Pro Lys Val Glu Leu Asp Gly Glu Pro
        50                  55                  60

Ser Met Asn Tyr Leu Glu Asp Val Tyr Val Gly Lys Ala Leu Leu Thr
65                  70                  75                  80

Asn Asp Thr Gln Gln Glu Gln Lys Leu Lys Ser Gln Ser Phe Thr Cys
                85                  90                  95

Lys Asn Thr Asp Thr Val Thr Ala Thr Thr His Thr Val Gly Thr
            100                 105                 110

Ser Ile Gln Ala Thr Ala Lys Phe Thr Val Pro Phe Asn Glu Thr Gly
        115                 120                 125

Val Ser Leu Thr Thr Ser Tyr Ser Phe Ala Asn Thr Asn Thr Asn Thr
130                 135                 140

Asn Ser Lys Glu Ile Thr His Asn Val Pro Ser Gln Asp Ile Leu Val
145                 150                 155                 160

Pro Ala Asn Thr Thr Val Glu Ala Ile Ala Tyr Leu Lys Lys Val Asn
                165                 170                 175
```

```
Val Lys Gly Asn Val Lys Leu Val Gly Gln Val Ser Gly Ser Glu Trp
            180                 185                 190

Gly Glu Ile Pro Ser Tyr Leu Ala Phe Pro Arg Asp Gly Tyr Lys Phe
            195                 200                 205

Ser Leu Ser Asp Thr Val Asn Lys Ser Asp Leu Asn Glu Asp Gly Thr
    210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
            260

<210> SEQ ID NO 50
<211> LENGTH: 263
<212> TYPE: PRT
<213> ORGANISM: Artificial Sequence
<220> FEATURE:
<223> OTHER INFORMATION: Mutant polypeptide

<400> SEQUENCE: 50

Met Gly Lys Ala Ser Tyr Asp Asn Val Asp Thr Leu Ile Glu Lys Gly
1               5                   10                  15

Arg Tyr Asn Thr Lys Tyr Asn Tyr Leu Lys Arg Met Glu Lys Tyr Tyr
            20                  25                  30

Pro Asn Ala Met Ala Tyr Phe Asp Lys Val Thr Ile Asn Pro Gln Gly
                35                  40                  45

Asn Asp Phe Tyr Ile Asn Asn Pro Lys Val Glu Leu Asp Gly Glu Pro
    50                  55                  60

Ser Met Asn Tyr Leu Glu Asp Val Tyr Val Gly Lys Ala Leu Leu Thr
65                  70                  75                  80

Asn Asp Thr Gln Gln Glu Gln Lys Leu Lys Ser Gln Ser Phe Thr Cys
                85                  90                  95

Lys Asn Thr Asp Thr Val Thr Ala Thr Thr Thr His Thr Val Gly Thr
            100                 105                 110

Ser Ile Gln Ala Thr Ala Lys Phe Thr Val Pro Phe Asn Glu Thr Gly
            115                 120                 125

Val Ser Leu Thr Thr Ser Tyr Ser Phe Ala Asn Thr Asn Thr Asn Thr
    130                 135                 140

Asn Ser Lys Glu Ile Thr His Asn Val Pro Ser Gln Asp Ile Leu Val
145                 150                 155                 160

Pro Ala Asn Thr Thr Val Glu Val Ile Phe Tyr Leu Lys Lys Val Asn
                165                 170                 175

Val Lys Gly Asn Val Lys Leu Val Gly Gln Val Ser Gly Ser Glu Trp
            180                 185                 190

Gly Glu Ile Pro Ser Tyr Leu Ala Phe Pro Arg Asp Gly Tyr Lys Phe
            195                 200                 205

Ser Leu Ser Asp Thr Val Asn Lys Ser Asp Leu Asn Glu Asp Gly Thr
    210                 215                 220

Ile Asn Ile Asn Gly Lys Gly Asn Tyr Ser Ala Val Met Gly Asp Glu
225                 230                 235                 240

Leu Ile Val Lys Val Arg Asn Leu Asn Thr Asn Asn Val Gln Glu Tyr
                245                 250                 255

Val Ile Pro Val Asp Lys Lys
            260
```

```
<210> SEQ ID NO 51
<211> LENGTH: 83
<212> TYPE: DNA
<213> ORGANISM: Artificial Sequence
<220> FEATURE:
<223> OTHER INFORMATION: Primer sequence

<400> SEQUENCE: 51
gaaaggaaga tataatacaa aatataatta cttaaagaga atggaaaaat atgcgcctaa      60
tgctatggca tattttgata agg                                             83

<210> SEQ ID NO 52
<211> LENGTH: 83
<212> TYPE: DNA
<213> ORGANISM: Artificial Sequence
<220> FEATURE:
<223> OTHER INFORMATION: Primer sequence

<400> SEQUENCE: 52
ccttatcaaa atatgccata gcattaggcg catattttc cattctcttt aagtaattat       60
attttgtatt atatcttcct ttc                                             83

<210> SEQ ID NO 53
<211> LENGTH: 49
<212> TYPE: DNA
<213> ORGANISM: Artificial Sequence
<220> FEATURE:
<223> OTHER INFORMATION: Primer sequence

<400> SEQUENCE: 53
gtgaatgggg agagatacct agtgcgttag cttttcctag ggatggtta                 49

<210> SEQ ID NO 54
<211> LENGTH: 49
<212> TYPE: DNA
<213> ORGANISM: Artificial Sequence
<220> FEATURE:
<223> OTHER INFORMATION: Primer sequence

<400> SEQUENCE: 54
taaccatccc taggaaaagc taacgcacta ggtatctctc cccattcac                 49

<210> SEQ ID NO 55
<211> LENGTH: 65
<212> TYPE: DNA
<213> ORGANISM: Artificial Sequence
<220> FEATURE:
<223> OTHER INFORMATION: Primer sequence

<400> SEQUENCE: 55
caaatacaaa tacaaatact aattcaaaag aaattactgc taatgtccct tcacaagata     60
tacta                                                                 65

<210> SEQ ID NO 56
<211> LENGTH: 65
<212> TYPE: DNA
<213> ORGANISM: Artificial Sequence
<220> FEATURE:
<223> OTHER INFORMATION: Primer sequence

<400> SEQUENCE: 56
tagtatatct tgtgaaggga cattagcagt aatttctttt gaattagtat ttgtatttgt     60
```

```
atttg                                                              65

<210> SEQ ID NO 57
<211> LENGTH: 54
<212> TYPE: DNA
<213> ORGANISM: Artificial Sequence
<220> FEATURE:
<223> OTHER INFORMATION: Primer sequence

<400> SEQUENCE: 57
agaaccatca atgaattatc ttgaagatgt ttattttgga aaagctctct taac         54

<210> SEQ ID NO 58
<211> LENGTH: 54
<212> TYPE: DNA
<213> ORGANISM: Artificial Sequence
<220> FEATURE:
<223> OTHER INFORMATION: Primer sequence

<400> SEQUENCE: 58
gttaagagag cttttccaaa ataaacatct tcaagataat tcattgatgg ttct         54

<210> SEQ ID NO 59
<211> LENGTH: 76
<212> TYPE: DNA
<213> ORGANISM: Artificial Sequence
<220> FEATURE:
<223> OTHER INFORMATION: Primer sequence

<400> SEQUENCE: 59
tcttaactaa tgatactcaa caagaacaaa aattaaaatc acaatcagcg acttgtaaaa   60
atactgatac agtaac                                                   76

<210> SEQ ID NO 60
<211> LENGTH: 76
<212> TYPE: DNA
<213> ORGANISM: Artificial Sequence
<220> FEATURE:
<223> OTHER INFORMATION: Primer sequence

<400> SEQUENCE: 60
gttactgtat cagtattttt acaagtcgct gattgtgatt ttaatttttg ttcttgttga   60
gtatcattag ttaaga                                                   76

<210> SEQ ID NO 61
<211> LENGTH: 64
<212> TYPE: DNA
<213> ORGANISM: Artificial Sequence
<220> FEATURE:
<223> OTHER INFORMATION: Primer sequence

<400> SEQUENCE: 61
atactagtac cagctaatac tactgtagaa gcgatagcat atttaaaaaa agttaatgtt   60
aaag                                                                64

<210> SEQ ID NO 62
<211> LENGTH: 64
<212> TYPE: DNA
<213> ORGANISM: Artificial Sequence
<220> FEATURE:
<223> OTHER INFORMATION: Primer sequence

<400> SEQUENCE: 62
ctttaacatt aacttttttt aaatatgcta tcgcttctac agtagtatta gctggtacta   60
```

```
gtat                                                                64
```

<210> SEQ ID NO 63
<211> LENGTH: 82
<212> TYPE: DNA
<213> ORGANISM: Artificial Sequence
<220> FEATURE:
<223> OTHER INFORMATION: Primer sequence

<400> SEQUENCE: 63

```
gatatactag taccagctaa tactactgta gaagtaatat tttatttaaa aaaagttaat    60
gttaaaggaa atgtaaagtt ag                                            82
```

<210> SEQ ID NO 64
<211> LENGTH: 82
<212> TYPE: DNA
<213> ORGANISM: Artificial Sequence
<220> FEATURE:
<223> OTHER INFORMATION: Primer sequence

<400> SEQUENCE: 64

```
ctaactttac atttccttta acattaactt ttttaaata aaatattact tctacagtag     60
tattagctgg tactagtata tc                                            82
```

<210> SEQ ID NO 65
<211> LENGTH: 260
<212> TYPE: PRT
<213> ORGANISM: Artificial Sequence
<220> FEATURE:
<223> OTHER INFORMATION: Protein fragment

<400> SEQUENCE: 65

Lys Ala Ser Tyr Asp Asn Val Asp Thr Leu Ile Glu Lys Gly Arg Tyr
1               5                   10                  15

Asn Thr Lys Tyr Asn Tyr Leu Lys Arg Met Glu Lys Tyr Tyr Pro Asn
            20                  25                  30

Ala Met Ala Tyr Phe Asp Lys Val Thr Ile Asn Pro Gln Gly Asn Asp
        35                  40                  45

Phe Tyr Ile Asn Asn Pro Lys Val Glu Leu Asp Gly Glu Pro Ser Met
    50                  55                  60

Asn Tyr Leu Glu Asp Val Tyr Val Gly Lys Ala Leu Leu Thr Asn Asp
65                  70                  75                  80

Thr Gln Gln Glu Gln Lys Leu Lys Ser Gln Ser Phe Thr Cys Lys Asn
                85                  90                  95

Thr Asp Thr Val Thr Ala Thr Thr His Thr Val Gly Thr Ser Ile
            100                 105                 110

Gln Ala Thr Ala Lys Phe Thr Val Pro Phe Asn Glu Thr Gly Val Ser
        115                 120                 125

Leu Thr Thr Ser Tyr Ser Phe Ala Asn Thr Asn Thr Asn Thr Asn Ser
    130                 135                 140

Lys Glu Ile Thr His Asn Val Pro Ser Gln Asp Ile Leu Val Pro Ala
145                 150                 155                 160

Asn Thr Thr Val Glu Val Ile Ala Tyr Leu Lys Lys Val Asn Val Lys
                165                 170                 175

Gly Asn Val Lys Leu Val Gly Gln Val Ser Gly Ser Glu Trp Gly Glu
            180                 185                 190

Ile Pro Ser Tyr Leu Ala Phe Pro Arg Asp Gly Tyr Lys Phe Ser Leu
        195                 200                 205

-continued

```
Ser Asp Thr Val Asn Lys Ser Asp Leu Asn Glu Asp Gly Thr Ile Asn
        210                 215                 220
Ile Asn Gly Lys Gly Asn Tyr Ser Ala Val Met Gly Asp Glu Leu Ile
225                 230                 235                 240
Val Lys Val Arg Asn Leu Asn Thr Asn Asn Val Gln Glu Tyr Val Ile
                245                 250                 255
Pro Val Asp Lys
            260

<210> SEQ ID NO 66
<211> LENGTH: 32
<212> TYPE: PRT
<213> ORGANISM: Artificial Sequence
<220> FEATURE:
<223> OTHER INFORMATION: Protein fragment

<400> SEQUENCE: 66

Met Lys Lys Asn Leu Val Lys Ser Leu Ala Ile Ala Ser Ala Val Ile
1               5                   10                  15
Ser Ile Tyr Ser Ile Val Asn Ile Val Ser Pro Thr Asn Val Ile Ala
            20                  25                  30

<210> SEQ ID NO 67
<211> LENGTH: 13
<212> TYPE: PRT
<213> ORGANISM: Artificial Sequence
<220> FEATURE:
<223> OTHER INFORMATION: Protein fragment

<400> SEQUENCE: 67

Lys Glu Ile Ser Asn Thr Val Ser Asn Glu Met Ser Lys
1               5                   10

<210> SEQ ID NO 68
<211> LENGTH: 23
<212> TYPE: PRT
<213> ORGANISM: Artificial Sequence
<220> FEATURE:
<223> OTHER INFORMATION: Protein fragment

<400> SEQUENCE: 68

Lys Glu Lys Ser Asn Asp Ser Asn Ile Val Lys Tyr Arg Ser Leu Tyr
1               5                   10                  15
Ile Lys Ala Pro Gly Ile Lys
            20
```

EPSILON TOXIN FROM CLOSTRIDIUM PERFRINGENS AS A VACCINE

FIELD OF THE INVENTION

This invention relates to methods and compositions for detecting, diagnosing, preventing, treating or ameliorating the symptoms of a demyelinating condition.

BACKGROUND

The rod-shaped, spore-forming, Gram-negative, anaerobe bacterium *Clostridium perfringens* is able to produce at least 17 toxins, making *C. perfringens* one of the most pathogenic species in the *Clostridium* genus. Depending on its ability to produce the four typing toxins, namely α-, β-, ε-, and ι-toxin, *C. perfringens* strains are classified into one of five toxinotypes, referred to as types A-E (Petit et al. (1999) Trends Microbiol. vol. 7, 104-110).

Epsilon toxin (Etx) is produced by toxinotypes B and D. These strains are responsible for a severe disease called enterotoxemia, which affects predominantly sheep and lambs but also causes infections in other ruminant species, including goats and calves (Songer (1996) Clin. Microbiol. Rev. vol. 9, 216-234). Enterotoxemia in naturally infected animals is usually characterised by systemic lesions in sheep and enterocolitis in goats. In addition to the typing toxins, the bacterium is able to produce a variety of so-called minor toxins such as β1, β2, δ, θ, λ, μ, ν, and enterotoxin (Rood (1998) Annu. Rev. Microbiol. vol. 52, 333-360).

The most important factor in initiating disease in sheep and other ruminants is overeating rich food, resulting in the presence of high amounts of carbohydrates in the intestine. This leads to disruption of the microbial balance in the gut, leading to proliferation of *C. perfringens* and consequent overproduction of Etx. The toxin causes an increase in intestinal permeability, facilitating its entry into the bloodstream and allowing its dissemination to the main target organs of the kidneys and the brain (McDonel (1980) Pharmacol Ther 10(3): 617-655). Here, intoxication results in fluid accumulation due to increased permeability of blood vessels. Accumulation in the central nervous system results in neurological disorder rapidly leading to death (Finnie (2003) Aust. Vet. J. vol. 81, 219-221).

More recently, Etx has been suggested to play a role in the development of multiple sclerosis in humans (Rumah et al. (2013) PLoS One 8: e76359).

Multiple sclerosis (MS) is a demyelinating disease in which the insulating covers of nerve cells in the brain and spinal cord are damaged. This damage disrupts the ability of parts of the nervous system to communicate, resulting in a range of symptoms, which can include double vision, blindness in one eye, muscle weakness, trouble with sensation, or trouble with coordination. The condition often begins as a clinically isolated syndrome (CIS) over a period of time, before being confirmed as Clinically Definite MS (CDMS).

Neuromyelitis optica spectrum disorder (NMOSD) is a rare neurological condition characterised by episodes of optic neuritis (ON), transverse myelitis (TM), together with one or more other diagnostic criteria including in some cases the presence of a specific antibody, aquaporin-4 (AQP-4).

Optic neuritis (ON) is a demyelinating inflammation of the optic nerve. It is frequently associated with multiple sclerosis. The autoimmune disease neuromyelitis optica (NMO) is a heterogeneous condition consisting of the simultaneous inflammation and demyelination of the optic nerve (optic neuritis) and the spinal cord (myelitis). Approximately 80% of patients diagnosed with NMO test positive for Aquaporin 4 (AQP-4) antibodies (www.nmouk.nhs.uk/healthcare-professionals/aqp4-antibodies) Zamvil et al., (Neurotherapeutics (2018) 15:92-101) speculate that gut microbiota, and possibly *C. perfringens* itself, could participate in NMO pathogenesis.

Transverse myelitis (TM) is an inflammation of both sides of one section of the spinal cord, and may also result in myelin damage.

Acute disseminated encephalomyelitis (ADEM) is characterized by a brief but widespread attack of inflammation in the brain and spinal cord that damages myelin. ADEM often follows viral or bacterial infections, or less often, vaccination for measles, mumps, or rubella. ADEM typically damages white matter, leading to neurological symptoms such as visual loss (due to inflammation of the optic nerve) in one or both eyes.

Etx is expressed with a signal sequence that directs export of the prototoxin from the bacterium (McDonel (1986) in *Pharmacology of bacterial toxins* eds. Dorner & Drew, Pergamon Press, 477-517). In development of disease, the relatively inactive prototoxin is converted to the active toxin by proteolytic cleavage in the gut lumen, either by digestive proteases of the host, such as trypsin and chymotrypsin (Bhown & Habeerb (1977) Biochem. Biophys. Res. Commun. vol. 78, 889-896), or by *C. perfringens* λ-protease (Minami et al. (1997) Microbiol. Immun. vol. 41, 527-535). Proteolytic activation of Etx can also be achieved in vitro by controlled proteolysis (Hunter et al. (1992) Infect. Immun. vol. 60, 102-110). Depending on the protease, proteolytic cleavage results in the removal of 10-13 amino-terminal and 22-29 carboxy-terminal amino acids (Bhown & Habeerb (1977); Minami et al. (1997)). Maximal activation occurs when both N- and C-termini are cleaved (Worthington & Mulders (1977) Infect. Immun. vol. 18, 549-551).

The 3D structure of Etx has been determined (Cole et al. (2004) Nature Structural & Molecular Biology vol. 11, 797-798) and reveals a molecule composed mainly of β-sheets, which can be divided into three functional domains. Domain I at the N-terminus contains the suggested receptor interaction region. Domain II in the middle contains an amphipathic β-hairpin, which is predicted to play a role in membrane insertion. Domain III at the C-terminus contains the C-terminal peptide, which has to be removed for activation to occur.

Epsilon toxin is an aerolysin-like β-pore forming toxin (β-PFT), with the amphipathic β-hairpin loops inserting into the membrane to form β-barrel structures. The overall fold of Etx shows similarity to the structure of aerolysin from the Gram-negative bacterium *Aeromonas hydrophila* (Parler et al. (1994) Nature vol. 367, 292-295), to parasporin-2 (PS) from *Bacillus thuringiensis* (Akiba et al. (2009) J. Mol. Biol. vol. 386, 121-133) and to a pore-forming lectin, LSL, from *Laetiporus sulphurous* (Mancheno et al. (2005) J. Biol. Chem. vol. 280, 17251-17259). The structural similarities between these toxins are most striking in their two C-terminal domains. Their N-terminal domains show a greater structural variation, which is likely to account for their differences in target cell specificities and potencies (Bokori-Brown et al. (2011) FEBS J. vol. 278, 4589-4601).

In aerolysin, the two amino-terminal domains (Domains I-II) are thought to play a role in binding to cell surfaces with overlapping functions (MacKenzie et al. (1999) J. Biol. Chem. vol. 274, 22604-22609) and it has been suggested that domain I of Etx, which is equivalent to domain II of aerolysin, performs a similar function (Cole et al. (2004)), but this has yet to be demonstrated. Domain II of aerolysin contains the mannose 6-phosphate binding loops. However, the residues of domain II involved in mannose-6-phosphate binding in aerolysin are not conserved in domain I of Etx, suggesting that the structural variation in the N-terminal receptor binding domains of these toxins is likely to account for the differences between their target cell specificities.

Etx is unique among β-PFTs because it is highly potent and has high cell specificity. Because of its high potency, Etx is considered to be a potential biological weapon for international terrorism by the U.S. Government Centres for Disease Control and Prevention (Morbidity and Mortality Weekly Report (MMWR) Recommendations and Reports (2000) vol. 49, 1-14). The 50% lethal dose ($LD_{50}$) of Etx in mice after intravenal injection is typically 100 ng/kg (Gill (1982) Microbiol. Rev. vol. 46, 86-94), making Etx the most potent clostridial toxin after botulinum neurotoxin. Etx also shows high cell specificity. Among the many cell lines tested, only four have been identified to be susceptible to the toxin. These include kidney cell lines of dog (MDCK (Knight et al. (1990) Biologicals vol. 18, 263-270)), mouse (mpkCCDcl4 (Chassin et al. (2007) Am. J. Physiol. Renal Physiol. vol. 293, F927-937)) and human (G-402 (Shortt et al. (2000) Hum. Exp. Toxicol. vol. 19, 108-116) and ACHN (Ivie et al. (2011) PloS ONE vol. 6, e17787) origin. Most in vitro studies on Etx have been carried out using the Madin-Darby Canine Kidney (MDCK) cell line, as this cell line is the most susceptible to the toxin (Payne et al. (1994) FEMS Microbiol. Lett. vol. 116, 161-167). The dose of Etx to kill 50% of MDCK cells ($CT_{50}$) is reported to be as low as 15 ng/ml.

The binding of Etx to MDCK cells is associated with the formation of a stable, high molecular weight complex (Petit et al. (1997) J. Bacteriol. vol. 179, 6480-6487). Intoxicated cells undergo morphological changes that include swelling and membrane blebbing before cell death (Petit et al. (1997) J. Bacteriol. vol. 179, 6480-6487). The rapid toxin-induced cell death and the specificity of epsilon toxin for only a few cell lines suggest the presence of a specific receptor(s) on target cells. Etx acts by binding to host cells and there is evidence that seven monomers of the protein assemble into a pore which spans the cell membrane (Miyata et al. (2002) J Biol Chem. 277: 39463-8), resulting in unregulated ion movement across the membrane and cell death. Toxicity appears to be a consequence of the formation of pores in the target cell membrane (Petit et a. (2001) J. Biol. Chem. vol. 276, 15736-15740).

The identity of the cell surface receptor for the toxin is still not fully clarified. There is evidence that the toxin binds to the hepatitis A virus cell receptor 1 proteins (HAVCR1) on MDCK.2 cells (Ivie et al. (2011) PLoS One 6: e17787). More recently, evidence has been presented that the receptor is myelin and lymphocyte protein (MAL) (Rumah et al. (2015) PLoS Pathog. 11: e1004896). CHO cells which are normally highly resistant to the toxin become sensitive when expressing MAL, and MAL knock-out mice are reported to be highly resistant to the toxin (Rumah et al. (2015)).

A number of commercial vaccines are available for the prevention of enterotoxaemia. These vaccines are typically produced by treating a C. perfringens culture filtrate with formaldehyde, resulting in detoxification of Etx. These vaccines contain a wide range of proteins in addition to Etx, and there can be considerable batch to batch variation in the immunogenicity of these preparations. Inflammatory responses following vaccination have been reported to result in reduced feed consumption. These shortfalls have prompted work to devise improved vaccines, and a number of recombinant immunogens have been reported including formaldehyde treated Etx produced from E. coli (Lobato et al. (2010) Vaccine 28:6125-7) and site directed mutants (genetic toxoids) of Etx with reduced toxicity (Kang et al. (2017) Human vaccines & immunotherapeutics 13:1598-608). Site directed mutants overcome the problem of batch to batch variation in immunogenicity associated with chemical detoxification methods of vaccine production. However, the high potency of the toxin can make it difficult to abolish toxicity. The toxicity of the mutants has been assessed using either MDCK cell cultures (Ivie and McClain (2012) Biochemistry 51:7588-95; Kang et al. (2017)) or in mice.

A site-directed mutant of Etx, Y30A-Y196A, was reported to have >430-fold decrease in cytotoxicity towards MDCK.2 cells compared with the wild type toxin and showed reduced but not abolished toxicity in mice (Bokori-Brown et al., (2014) Vaccine vol. 32, 2682-2687).

There is a continued need to identify improved molecules with potential for use as a vaccine against disease caused by or associated with the presence of Etx and/or caused by infection by C. perfringens.

DETAILED DESCRIPTION OF THE INVENTION

This invention relates to methods and compositions for detecting, diagnosing, preventing, treating or ameliorating the symptoms of a demyelinating condition selected from: enterotoxemia (ET), multiple sclerosis (MS), clinically definite MS (CDMS), clinically isolated syndrome (CIS), neuromyelitis optica spectrum disorder (NMOSD), optic neuritis (ON), neuromyelitis optica (NMO), myelitis, transverse myelitis (TM), a disease or condition characterised by the increase or presence of antibodies against aquaporin-4 (AQP4) and/or astrocyte damage, and acute disseminated encephalomyelitis (ADEM) in a human or animal subject in need. The methods comprise administering to the subject a composition comprising an effective amount of an agent that directly or indirectly interferes with epsilon toxin (Etx) produced by Clostridium perfringens type B or type D bacterial strain, an Etx-binding receptor, or an interaction of Etx with its binding receptor so as to inhibit or suppress Etx modulated receptor signalling activities.

The invention relates to novel polypeptides useful as a vaccine against diseases caused by or associated with the epsilon toxin of Clostridium perfringens, particularly in animals susceptible to development of enterotoxemia and in the treatment of a demyelinating condition.

The present inventors have found that subjects having demyelinating conditions, such as enetrotoxemia (ET), neuromyelitis optica (NMO) and transverse myelitis (TM), the latter two being examples of neuromyelitis optica spectrum disorder (NMOSD), also tested positive for the presence of epsilon toxin (Etx) produced by Clostridium perfringens type B or type D and/or tested positive for the presence of antibodies against aquaporin-4 (AQP4).

Demyelinating conditions are characterised by damage to the myelin sheath and include conditions selected from: enterotoxemia (ET), multiple sclerosis (MS), clinically definite MS (CDMS), clinically isolated syndrome (CIS), neuromyelitis optica spectrum disorder (NMOSD), optic neuritis (ON), neuromyelitis optica (NMO), myelitis, transverse myelitis (TM), a disease or condition characterised by the increase or presence of antibodies against aquaporin-4 (AQP4) and/or astrocyte damage, and acute disseminated encephalomyelitis (ADEM).

According to a first aspect of the present invention, there is provided a method for preventing, treating or ameliorating the symptoms of a demyelinating condition selected from: enterotoxemia (ET), multiple sclerosis (MS), clinically definite MS (CDMS), clinically isolated syndrome (CIS), neuromyelitis optica spectrum disorder (NMOSD), optic neuritis (ON), neuromyelitis optica (NMO), myelitis, transverse myelitis (TM), a disease or condition characterised by the increase or presence of antibodies against aquaporin-4 (AQP-4) and/or astrocyte damage, and acute disseminated encephalomyelitis (ADEM) in a human or animal subject in need. The methods comprise administering to the subject a composition comprising an effective amount of an agent that directly or indirectly interferes with epsilon toxin (ETX) produced by *Clostridium perfringens* type B or type D bacterial strain, an ETX-binding receptor, or an interaction of ETX with its binding receptor so as to inhibit or suppress ETX modulated receptor signalling activities.

According to a second aspect of the invention, the composition comprising an agent that directly or indirectly interferes with epsilon toxin (ETX) produced by *Clostridium perfringens* type B or type D bacterial strain, an ETX-binding receptor, or an interaction of ETX with its binding receptor so as to inhibit or suppress ETX modulated receptor signalling activities is a *C perfringens* epsilon toxin (Etx) polypeptide having reduced toxicity to cells expressing Myelin And Lymphocyte (MAL) protein and comprising a modified domain III compared to wild type Etx polypeptide having sequence SEQ ID NO:65, wherein said reduced toxicity is relative to SEQ ID NO: 65 and/or SEQ ID NO: 14 and wherein said Etx polypeptide is capable of binding to at least one antibody which binds to a sequence represented by SEQ ID NO:65 and/or SEQ ID NO:14.

Alternatively or additionally to the ability to bind an antibody which binds to SEQ ID NO:13 and/or SEQ ID NO:14, the polypeptide may bind to at least one antibody which binds to SEQ ID NO:11, the non-activated prototoxin form of the epsilon toxin.

A modified domain III may be any modification in the glycan (β-octyl-glucoside) binding site of domain III and/or in the sugar binding capacity of domain III and/or a modification of domain III which confers to the Etx polypeptide a reduced capacity to bind to CHO cells expressing MAL, compared to the corresponding wild type sequence when activated.

A modified domain III may comprise one or more amino acid mutations within the amino acid sequences making up domain III (SEQ ID NOs 1, 2 and 3): VYVGKALLTNDTQQEQKLKSQSFTCK (SEQ ID NO: 1), THNVPSQDILVPANTTVEVIAYLK (SEQ ID NO: 2); and DELIVKVRNLNTNNVQEYVIPVDKKEKSNDSNIV-KYRSLYIKAPGIK (SEQ ID NO: 3), a mutation being a substitution or deletion of at least 1, 2, 3, 4, 5, 6, 7, 8, 9, 10 or more or substantially all of the amino acid residues in domain III (SEQ ID NOs 1, 2 and 3). Where there is more than one mutation in domain III, the mutations may optionally be a combination of substitutions and deletions.

The modified domain III may comprise one or more of the following mutations in SEQ ID NOs 1 and 2: VY̲VGKALLTNDTQQEQKLKSQSF̲TCK (SEQ ID NO: 1), where the underlined and bold V and F may be substituted for any other amino acid or may be deleted. For example, V may be substituted for F (V[F]) and/or F substituted for A (F[A]); TH̲NVPSQDILVPANTTVEVI-AYLK (SEQ ID NO: 2), where the underlined and bold H̲, V and A may be substituted for any other amino acid or may be deleted. For example, H may be substituted for A (H[A]), V substituted for A (V[A]) and/or A substituted for F (A[F]).

The polypeptide of the invention may comprise a mutation at a position as set out in Table 1 below, which gives examples of suitable mutations in domain III (SEQ ID NOs 6-10). The mutations shown in SEQ ID NOs 4 and 5 are domain I mutations. The Etx polypeptide of the invention may therefore comprise one or more of the following sequences representing a mutation in domain III: SEQ ID NO:6, SEQ ID NO:7, SEQ ID NO:8, SEQ ID NO:9 and SEQ ID NO: 10; or one or more of the mutations comprised in SEQ ID NOs 1 and/or 2.

TABLE 1

MUTATIONS COMPRISED IN SEQ ID NOS 4-10

| SEQ ID NO | Sequence | Change | Mutation position compared to equivalent in SEQ ID NO: 65 |
|---|---|---|---|
| SEQ ID NO: 4 | RMEKYXPNAM | Where X is any amino acid other than Y (tyrosine), preferably wherein X is A (alanine) or wherein X is a deletion | 30 |
| SEQ ID NO: 5 | GEIPSXLAFP | Where X is any amino acid other than Y (tyrosine), preferably wherein X is A (alanine) or wherein X is a deletion | 196 |
| SEQ ID NO: 6 | SKEITXNVPS | Where X is any amino acid other than H (histidine), preferably wherein X is A (alanine) or wherein X is a deletion | 149 |
| SEQ ID NO: 7 | LEDVYXGKAL | Where X is any amino acid other than V (valine), preferably wherein X is F (phenylalanine) or wherein X is a deletion | 72 |

TABLE 1-continued

MUTATIONS COMPRISED IN SEQ ID NOS 4-10

| SEQ ID NO | Sequence | Change | Mutation position compared to equivalent in SEQ ID NO: 65 |
|---|---|---|---|
| SEQ ID NO: 8 | LKSQSXTCKN | Where X is any amino acid other than F (phenylalanine), preferably wherein X is A (alanine) or wherein X is a deletion | 92 |
| SEQ ID NO: 9 | NTTVEXIAYL | Where X is any amino acid other than V (valine), preferably wherein X is A (alanine) or wherein X is a deletion | 166 |
| SEQ ID NO: 10 | TVEVIXYLKK | Where X is any amino acid other than A (alanine), preferably wherein X is F (phenylalanine) or wherein X is a deletion | 168 |

The mutation comprised within any one or more of SEQ ID NOs 4-10 may be comprised within a stretch of at least 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 255, 260, 261, 262, 263 contiguous amino acids from SEQ ID NO: 13, comprising one or more of SEQ ID NOs 4-10.

The invention need not be limited to the specific mutations of Table 1 and any mutation(s) which affect the sugar binding capacity of domain III and/or which mutation(s) confer a reduced capacity of an Etx polypeptide to bind to (CHO) cells expressing MAL equally form part of the present invention. A person skilled in the art could readily identify suitable mutations using known tools and routine techniques, for example those described herein.

As shown in Table 2 below, SEQ ID NO: 11 is full length wild type *C. perfringens* epsilon toxin and SEQ ID NO: 12 is the same sequence, but lacking the first 32 amino acids. This sequence, SEQ ID NO:12, is the sequence published for the crystal structure (see the Research Collaboratory for Structural Bioinformatics (RCSB) databank at www.rcsb.org/pdb; PDB ID: 1UYJ).

SEQ ID NO:65 is the trypsin activated wild type *C. perfringens* epsilon toxin which remains after trypsin protease cleavage, with N- and C-termini removed. SEQ ID NOs:11 and 65 have 79% identity at the global alignment level, when determined as outlined below.

SEQ ID NO:13 is a recombinant toxin comprising SEQ ID NO:65 and two additional amino acid residues at the N-terminal end. SEQ ID NO:14 is a sequence equivalent to SEQ ID NO:13 but with a H>A mutation at position 151 of SEQ ID NO:13 (mentioned in the Examples below as the H149A mutation, with the difference in residue numbering explained below). This is a variant of the activated toxin which may be studied in the laboratory at ACGM level 2 (Oyston et al. (1998) Microbiol. vol. 144 (Pt 2), 333-341) and so may be more convenient practically for determining antibody binding. Inclusion of the H149A mutation described herein would doubly ensure that the polypeptide according to the invention could be used at ACGM level 2.

TABLE 2

IDENTITY OF SEQUENCES

| SEQ ID NO | Identity of sequence |
|---|---|
| 11 | full length wild-type native epsilon toxin |
| 12 | sequence used to obtain crystal structure (PDB ID:1YUJ) |
| 13 | trypsin activated recombinant epsilon toxin |
| 14 | trypsin activated recombinant epsilon toxin with H149A mutation |
| 15 | recombinant epsilon toxin sequence |
| 65 | trypsin activated wild-type epsilon toxin |

Reference herein to the following mutation positions mentioned in Table 1, i.e. 30, 196, 72, 92, 149, 166 and 168 are as counted from position 1 of SEQ ID NO: 65. The same residue positions may be found in SEQ ID NO: 11 (counting starting from residue 46, i.e. SEQ ID NO:65 lacks residues 1-32 of SEQ ID NO:11 (the signal sequence) and residues 33-45 (the N-terminal pro-peptide)). The same residue positions may be found in SEQ ID NO: 12 (counting staring from residue 14, i.e. SEQ ID NO:65 lack residues 1-13 of SEQ ID NO:12 (the N-terminal pro-peptide)). The same residue positions may be found in SEQ ID NOs 13 and 14 (counting starting from residue 3, i.e. SEQ ID NO:65 lacks residues 1-2 of SEQ ID NOs: 13 and 14 (part of a synthetic signal sequence)). The same residue positions may be found in SEQ ID NO: 15 (counting starting from residue 25, i.e. SEQ ID NO:65 lacks residues 1-24 of SEQ ID NO:15 (synthetic signal sequence). A person skilled in the art would readily be able to determine mutations at positions equivalent to positions 30, 196, 72, 92, 149, 166 and 168 in any given Etx polypeptide.

Reference to "Y30A-Y196A" and "Y43A-Y209A" double mutants are used interchangeably herein to refer to the same mutation positions within the Etx wild-type sequence (represented by SEQ ID NO:65), with the position numbering depending on whether the position is within activated toxin or the inactive precursor thereof. The positions 30 and 196 when the double mutant is referred to as Y30A-Y196A are counted from the start of the activated protein (position 1 of the sequence shown in SEQ ID NO:65)

and the equivalent positions 43 and 209 when the double mutant is referred to as Y43A-Y209A are counted from the start of the inactive precursor (i.e., starting from position −13 of the sequence shown in FIG. 2 or starting from position 1 of SEQ ID NO: 12). The mutation positions for the V72F, F92A, H149A, V166A, A168F mutations are as found in SEQ ID NO:65.

In a previous study (WO 2013/144636), it was shown that Y30A-Y196A double mutants (located in domain I) markedly reduced the ability of the toxin to bind to and kill MDCK cells and had reduced toxicity in mice, suggesting that Y30A-Y196A mutant could form the basis of an improved recombinant vaccine against enterotoxemia.

The previous study however used the MDCK cell line to measure cytotoxicity. Surprisingly, the double mutant did not give the same reduced toxicity results in CHO cells expressing MAL. It has surprisingly now been found that modifying domain III of the Etx polypeptide, for example by introducing one or more mutations into domain III, reduces toxicity in CHO cells expressing MAL. The modification to domain III may, for example, be any modification described herein.

The modification(s) to domain III therefore improved known vaccine candidate Y30A-Y196A as described in WO 2013/144636. Most in vitro studies on Etx have been carried out using the MDCK cell line, as this cell line was considered the most susceptible to the toxin (Payne et al. (1994) FEMS Microbiol. Lett. vol. 116, 161-167). Given that Etx vaccine candidates will likely not have been tested on (CHO) cells expressing MAL, the present invention provides an opportunity to improve existing Etx vaccines and Etx vaccine candidates by modifying domain III as described herein.

The polypeptide according to the invention may comprise a modified domain III compared to the wild type polypeptide SEQ ID NO:65, the polypeptide according to the invention showing reduced toxicity compared to an Etx polypeptide comprising SEQ ID NO: 4 and SEQ ID NO: 5 or compared to an Etx polypeptide comprising SEQ ID NO: 4, SEQ ID NO: 5 and SEQ ID NO: 6. In this context, the "Etx polypeptide" may be one having at least about 60%, 65%, 70%, 75%, 80%, 85%, 90%, 95%, 96%, 97%, 98%, 99% or about 100% sequence identity at a global level to SEQ ID NO:65, the polypeptide being capable of binding to at least one antibody which can bind to SEQ ID NO:65.

SEQ ID NOs 4 and 5 are present in the Y30A-Y196A double mutant, but the mutation of other tyrosine residues in domain I has also been shown to be effective in reducing toxicity of MDCK cells. For example, the mutated tyrosine residue(s) may, for example, be mutations (substitutions or deletions) of one or more of Y29, Y33, Y42, Y43, Y49 and/or Y209, the residue numbering here being counted from the start of the inactive precursor (i.e., starting from position −13 of the sequence shown in FIG. 2 or starting from position 1 of SEQ ID NO:12). The tyrosine mutation(s) may be comprised within a stretch of at least 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 255, 256, 257, 258, 259 or 260 contiguous amino acids from SEQ ID NO:65.

According to the present invention, there is also provided an Etx polypeptide having a modified domain III compared to wild type polypeptide SEQ ID NO:65 and showing reduced toxicity compared to other Etx vaccine polypeptides and polypeptides which are candidates for use as vaccines. For example, the following publications disclose polypeptides which have been shown to reduce toxicity towards MCDK cells and may be further improved by modifying domain III: Kang J et al. (2017) Hum Vaccin Immunother 13: 1598-1608 describes a proposed human vaccine with a mutation, F199, in domain 1; Yao et al. (2016) Sci Rep. 6: 24162 describes a Y196 mutation in domain 1; Li et al. (2013) Hum Vaccin Immunother 9: 2386-92 describes F199E and H106P mutants (F199 is in domain 1 and H106 is in domain 2); Oyston et a. (1998) Microbiology 144:333-41 describes a H106P mutant and also mentions H149P mutant as non-toxic (H106 is in domain 2); Dorca-Arevalo et al. (2014) PLoS One 9:e102417 describes V56C/F118C and H106P mutations as being non-toxic to MDCK cells (V56 is in domain 2 and F118 is in domain 2).

It was further surprisingly found that the Y30A-Y196A double mutant showed different toxicity results depending on the species from which the MAL is derived. For example, the double mutant was only marginally less toxic towards CHO cells expressing sheep MAL, but was more toxic to CHO cells expressing human MAL compared to wild type Etx. However, in CHO cells expressing dog MAL, the mutant was markedly less toxic. This finding suggests that MAL from different species interacts differently with Etx, indicating that MDCK cells may not be a good model for testing the toxicity of Etx vaccine candidates and that CHO cells expressing MAL might be a better model for such testing. Therefore, according to a further aspect of the present invention, there is provided use of (CHO) cells expressing MAL as a model in the testing for toxicity of epsilon vaccine candidates.

Table 3 below shows examples of mutations introduced into domain III of a Y30A-Y196A double mutant.

TABLE 3

Y30A-Y196A FURTHER MUTATIONS

| SEQ ID NO of trypsin activated recombinant epsilon toxin | Mutation Positions (counted from residue 1 of SEQ ID NO: 65) X may be any other amino acid than the one shown preceding the position number | Mutation Example |
|---|---|---|
| SEQ ID NO: 16 | Y30X + Y196X | Y30A + Y196A |
| SEQ ID NO: 17 | Y30X + Y196X + H149X | Y30A + Y196A + H149A |
| SEQ ID NO: 18 | Y30X + Y196X + V72X | Y30A + Y196A + V72F |
| SEQ ID NO: 19 | Y30X + Y196X + F92X | Y30A + Y196A + F92A |
| SEQ ID NO: 20 | Y30X + Y196X + V166X | Y30A + Y196A + V166A |
| SEQ ID NO: 21 | Y30X + Y196X + A168X | Y30A + Y196A + A168F |
| SEQ ID NO: 22 | Y30X + Y196X + H149X + V72X | Y30A + Y196A + H149A + V72F |
| SEQ ID NO: 23 | Y30X + Y196X + H149X + F92X | Y30A + Y196A + H149A + F92A |
| SEQ ID NO: 24 | Y30X + Y196X + H149X + V166X | Y30A + Y196A + H194A + V166A |
| SEQ ID NO: 25 | Y30X + Y196X + H149X + A168X | Y30A + Y196A + H149A + A168F |
| SEQ ID NO: 26 | Y30X + Y196X + V72X + F92X | Y30A + Y196A + V72F + F92A |
| SEQ ID NO: 27 | Y30X + Y196X + V72X + V166X | Y30A + Y196A + V72F + V166A |
| SEQ ID NO: 28 | Y30X + Y196X + V72X + A168X | Y30A + Y196A + V72F + A168F |
| SEQ ID NO: 29 | Y30X + Y196X + V92X + V166X | Y30A + Y196A + V92F + V166A |
| SEQ ID NO: 30 | Y30X + Y196X + V92X + A168X | Y30A + Y196A + V92F + A168F |
| SEQ ID NO: 31 | Y30X + Y196X + V166X + A168X | Y30A + Y196A + V166A + A168F |
| SEQ ID NO: 32 | Y30X + Y196X + H149X + V72X + F92X | Y30A + Y196A + H149A + V72F + F92A |

TABLE 3-continued

Y30A-Y196A FURTHER MUTATIONS

| SEQ ID NO of trypsin activated recombinant epsilon toxin | Mutation Positions (counted from residue 1 of SEQ ID NO: 65) X may be any other amino acid than the one shown preceding the position number | Mutation Example |
|---|---|---|
| SEQ ID NO: 33 | Y30X + Y196X + H149X + V72X + V166X | Y30A + Y196A + H149A + V72F + V166X |
| SEQ ID NO: 34 | Y30X + Y196X + H149X + V72X + A168X | Y30A + Y196A + H149A + V72F + A168X |
| SEQ ID NO: 35 | Y30X + Y196X + H149X + F92X + V166X | Y30A + Y196A + H149A + F92A + V166A |
| SEQ ID NO: 36 | Y30X + Y196X + H149X + F92X + A168X | Y30A + Y196A + H149A + F92A + A168F |
| SEQ ID NO: 37 | Y30X + Y196X + H149X + V166X + A168X | Y30A + Y196A + H149A + V166A + A168F |
| SEQ ID NO: 38 | Y30X + Y196X + V72X + F92X + V166X | Y30A + Y196A + V72F + F92A + V166A |
| SEQ ID NO: 39 | Y30X + Y196X + V72X + F92X + A168X | Y30A + Y196A + V72F + F92A + A168F |
| SEQ ID NO: 40 | Y30X + Y196X + V72X + V166X + A168X | Y30A + Y196A + V72F + V166A + A168F |
| SEQ ID NO: 41 | Y30X + Y196X + F92X + V166X + A168X | Y30A + Y196A + F92A + V166A + A168F |
| SEQ ID NO: 42 | Y30X + Y196X + H149X + V72X + F92X + V166X | Y30A + Y196A + H149A + V72F + F92A + V166A |
| SEQ ID NO: 43 | Y30X + Y196X + H149X + V72X + F92X + A168X | Y30A + Y196A + H149A + V72F + F92A + A168F |
| SEQ ID NO: 44 | Y30X + Y196X + V72X + F92X + V166X + A168X | Y30A + Y196A + V72F + F92A + V166A + A168F |
| SEQ ID NO: 45 | Y30X + Y196X + H149X + V72X + F92X + V166X + A168X | Y30A + Y196A + H149A + V72F + F92A + V166A + A168F |
| SEQ ID NO: 46 | V72X | V72F |
| SEQ ID NO: 47 | F92X | F92A |
| SEQ ID NO: 48 | H149X | H149A |
| SEQ ID NO: 49 | V166X | V166A |
| SEQ ID NO: 50 | A168X | A168F |

The new sequences described herein (SEQ ID NOs 18 to 50 of Table 3) are therefore genetic toxoids suitable for incorporation into next generation enterotoxaemia or demyelinating disease vaccines; and vaccines against developing a disease caused by or associated with *Clostridium perfringens* and/or Etx. In particular, SEQ ID NO: 21 is suitable.

The mutations shown in Table 3 are described as comprised in a trypsin activated recombinant Etx (SEQ ID NO:13 or SEQ ID NO: 65), but the same mutations may also be comprised at equivalent positions in a full length Etx polypeptide (SEQ ID NO:11) or at equivalent positions in the full length recombinant Etx polypeptide (SEQ ID NO:15); or the mutations shown in Table 3 may be comprised at equivalent positions in a sequence having at least 60%, 65%, 70%, 75%, 80%, 85%, 90%, 95%, 96%, 97%, 98% or 99% sequence identity to SEQ ID NOs 11, 12, 13, 14, 15 or 65.

Any of the mutations described herein may be comprised in a sequence having at least 60%, 65%, 70%, 75%, 80%, 85%, 90%, 95%, 96%, 97%, 98% or 99% sequence identity to SEQ ID NOs 11, 12, 13, 14, 15 or 65.

The polypeptides of SEQ ID NOs 18 to 50 may have equal or similar or reduced toxicity to SEQ ID NO:14, or SEQ ID NO:14 lacking the first 2 N-terminal amino acid residues, and/or be non-toxic.

The polypeptide according to the invention may include a sequence of at least 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310 or 315 contiguous amino acids from any of SEQ ID NO: 11, SEQ ID NO: 12, SEQ ID NO: 13, SEQ ID NO: 14, SEQ ID NO: 15 or SEQ ID NO: 65 and comprising a double mutation at positions equivalent to positions 30-196 of SEQ ID NO:65 and additionally at least one, two or more mutations at positions equivalent to positions 72, 92, 149, 166 and 168. The numbering of the mutation positions is as described herein. The mutations may comprise a substitution or deletion.

The polypeptide according to the invention may include a sequence of at least 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 261, 262 or 263 contiguous amino acids from any one of SEQ ID NOs 18 to 50 from Table 3 and comprising or consisting of the mutations indicated for the relevant SEQ ID NO in Table 3.

The inclusion of one of amino acid sequences SEQ ID NOs 4 to 10 in the polypeptide according to the invention has the result that the sequence included in the polypeptide is identical to the equivalent (i.e., corresponding) sequence from any of SEQ ID NO: 11, SEQ ID NO: 12, SEQ ID NO: 13, SEQ ID NO: 14, SEQ ID NO: 15 or SEQ ID NO: 65, apart from the mutated position included as "X" within one or SEQ ID NOs 4 to 10.

The polypeptide according to the invention may have at least 60%, 65%, 70%, 75%, 80%, 85%, 90%, 95%, 96%, 97%, 98%, 99% or 100% sequence identity to any one of SEQ ID NOs 18 to 50 from Table 3 and comprising or consisting of the mutations indicated for the relevant SEQ ID NO.

The level of toxicity may be determined as described herein, in vitro or in vivo. For example, by use of a cell-based assay, such as MDCK.2 cell-based LDH assay, ACHN cells, the use of Chinese hamster ovary (CHO) cells (for example, CHO cells expressing green fluorescent protein (GFP), Human MAL (CHO-hMAL), sheep MAL (CHO-sMAL), dog MAL (CHO-dMAL) etc.). Toxicity studies may also be carried out in vivo, for example, in mice or any other suitable animal.

The polypeptides of the invention provide protection, when administered to a subject such as a human or a non-human animal such as lamb, sheep, goat, pig, cows, horses or rabbits, to the subject from developing a disease (such as enterotoxemia) caused by infection by *Clostridium perfringens* and/or caused by the presence of active epsilon toxin (or associated with the presence of *Clostridium perfringens* or the toxin) and/or a condition associated with demyelination. Such protection may be partial, whereby the probability of an individual subject within a population of developing disease is reduced, or complete, whereby the subject will not develop disease (i.e., the probability of developing disease caused by or associated with *C. perfringens* and/or by Etx is 0%).

The term "subject" as used throughout this specification, in relation to any aspect of the invention, indicates any human or animal individual, including (but not limited to) a cat, dog or horse, or a ruminant animal, cow, sheep, goat or pig. The human or animal may be a human or animal exhibiting symptoms of a demyelinating disease, for example enterotoxemia (ET), multiple sclerosis (MS), clinically definite MS (CDMS), clinically isolated syndrome (CIS), neuromyelitis optica spectrum disorder (NMOSD), optic neuritis (ON) or neuromyelitis optica (NMO), myelitis, transverse myelitis (TM), a disease or condition characterised by the increase or presence of antibodies against aquaporin-4 (AQP-4) and/or astrocyte damage, and acute disseminated encephalomyelitis (ADEM).

As outlined further below, sequence identity may be determined using the Needleman-Wunsch Global Sequence Alignment Tool available from the National Center for Biotechnology Information (NCBI), Bethesda, Maryland, USA, for example via blast.ncbi.nlm.nih.gov/Blast.cgi, using default parameter settings. When comparing the level of sequence identity to (for example) SEQ ID NO: 65, this typically should be done relative to the whole length of SEQ ID NO: 65, to avoid short regions of high identity overlap resulting in a high overall assessment of identity (i.e., a global alignment method is used). For example, a short polypeptide fragment having, for example, five amino acids might have a 100% identical sequence to a five amino acid region within the whole of SEQ ID NO: 65, but this does not provide a 100% amino acid identity unless the fragment forms part of a longer sequence which also has identical amino acids at the other positions equivalent to positions in SEQ ID NO:65. For example, SEQ ID NO: 11 is 79% identical at a global level to SEQ ID NO:65; positions 46-305 of SEQ ID NO:11 are 100% identical to positions 1-260 of SEQ ID NO:65, with positions 1-45 and 306-328 of SEQ ID NO:11 being absent from SEQ ID NO: 65. SEQ ID NO:65 is the sequence equivalent to (or corresponding to) positions 46-305 of SEQ ID NO:11 and positions 46-305 of SEQ ID NO: 11 are equivalent to (or correspond to) SEQ ID NO: 65.

Therefore, the skilled person is readily able to determine equivalent positions between two sequences, by aligning sequences to achieve maximum identical amino acids at as many positions as possible, for example by using a global sequence alignment program such as is available via blast.ncbi.nlm.nih.gov/Blast.cgi, discussed further below.

The present invention also encompasses polypeptides comprising variants of the polypeptides and methods utilising these variant polypeptides. As used herein, a "variant" means a polypeptide in which the amino acid sequence differs from the base sequence from which it is derived in that one or more amino acids within the sequence are substituted for other amino acids. The variant is a functional variant, in that the functional characteristics of the polypeptide from which the variant is derived are maintained. For example, the variant polypeptide may have a similar ability to bind an antibody capable of binding to a non-variant polypeptide (such as, by way of non-limiting example, any of SEQ ID NOs 18 to 50 of Table 3). In particular, any amino acid substitutions, additions or deletions must not alter or significantly alter the tertiary structure of one or more epitopes contained within the polypeptide from which the variant is derived, so that the variant polypeptide retains the ability to bind to an antibody which binds to SEQ ID NO:65 or 14. The skilled person is readily able to determine appropriate functional variants and to determine the tertiary structure of an epitope and any alterations thereof, without the application of inventive skill.

Amino acid substitutions may be regarded as "conservative" where an amino acid is replaced with a different amino acid with broadly similar properties. Non-conservative substitutions are where amino acids are replaced with amino acids of a different type.

By "conservative substitution" is meant the substitution of an amino acid by another amino acid of the same class, in which the classes are defined as follows:

| CLASS | AMINO ACID EXAMPLES |
|---|---|
| Nonpolar: | Ala, Val, Leu, Ile, Pro, Met, Phe, Trp |
| Uncharged polar: | Gly, Ser, Thr, Cys, Tyr, Asn, Gln |
| Acidic: | Asp, Glu |
| Basic: | Lys, Arg, His. |

As is well known to those skilled in the art, altering the primary structure of a polypeptide by a conservative substitution may not significantly alter the activity of that polypeptide because the side-chain of the amino acid which is inserted into the sequence may be able to form similar bonds and contacts as the side chain of the amino acid which has been substituted out. This is so even when the substitution is in a region which is critical in determining the polypeptide's conformation.

As mentioned above, non-conservative substitutions are possible provided that these do not disrupt the tertiary structure of an epitope within the polypeptide, for example, which do not interrupt the immunogenicity (for example, the antigenicity) of the polypeptide.

Broadly speaking, fewer non-conservative substitutions will be possible without altering the biological activity of the polypeptide. As mentioned above, variants may suitably be at least about 60%, 65%, 70%, 75%, 80%, 85%, 90%, 95%, 96%, 97%, 98%, 99% identical to the base sequence.

As already briefly mentioned, sequence identity between amino acid sequences can be determined by comparing an alignment of the sequences. When an equivalent position in the compared sequences is occupied by the same amino acid, then the molecules are identical at that position. Scoring an alignment as a percentage of identity is a function of the number of identical amino acids at positions shared by the compared sequences. When comparing sequences, optimal alignments may require gaps to be introduced into one or more of the sequences, to take into consideration possible insertions and deletions in the sequences. Sequence comparison methods may employ gap penalties so that, for the same number of identical molecules in sequences being compared, a sequence alignment with as few gaps as possible, reflecting higher relatedness between the two compared sequences, will achieve a higher score than one with many gaps. Calculation of maximum percent identity involves the production of an optimal alignment, taking into consideration gap penalties. As mentioned above, the percentage sequence identity should be determined using the Needleman-Wunsch Global Sequence Alignment tool, publicly available via blast.ncbi.nlm.nih.gov/Blast.cgi, using default parameter settings. The Needleman-Wunsch algorithm was published in J. Mol. Biol. (1970) vol. 48:443-53.

A further aspect of the invention provides a polynucleotide having a nucleic acid sequence which encodes for a polypeptide according to the first aspect of the invention. The invention also encompasses variant nucleic acids encoding the polypeptides of the invention. The term "variant" in relation to a nucleic acid sequence means any substitution of, variation of, modification of, deletion of, or addition of one or more nucleic acid(s) from or to a polynucleotide sequence, providing the resultant polypeptide sequence encoded by the polynucleotide exhibits at least the same properties as the polypeptide encoded by the basic sequence. The term therefore includes allelic variants and also includes a polynucleotide (a "probe sequence") which substantially hybridises to the polynucleotide sequence of the present invention. Such hybridisation may occur at or between low and high stringency conditions. In general terms, low stringency conditions can be defined as hybridisation in which the washing step takes place in a 0.330-0.825 M NaCl buffer solution at a temperature of about 40-48° C. below the calculated or actual melting temperature ($T_m$) of the probe sequence (for example, about ambient laboratory temperature to about 55 C), while high stringency conditions involve a wash in a 0.0165-0.0330 M NaCl buffer solution at a temperature of about 5-10° C. below the calculated or actual $T_m$ of the probe sequence (for example, about 65° C.). The buffer solution may, for example, be SSC buffer (0.15M NaCl and 0.015M tri-sodium citrate), with the low stringency wash taking place in 3×SSC buffer and the high stringency wash taking place in 0.1×SSC buffer. Steps involved in hybridisation of nucleic acid sequences have been described for example in Sambrook et al. (2001; "Molecular Cloning: a laboratory manual", $3^{rd}$ Edition, Cold Spring Harbor Laboratory Press, New York).

Polypeptides and nucleic acids of the invention may be prepared synthetically using conventional synthesisers. Alternatively, they may be produced using recombinant DNA technology and may be incorporated into a suitable expression vector, which is then used to transform a suitable host cell, such as a prokaryotic cell such as *E. coli*. The transformed host cells are cultured and the polypeptide isolated therefrom.

Therefore, the invention also provides a vector comprising such a polynucleotide. This includes recombinant constructs comprising one or more of the nucleic acid molecules described above. The constructs comprise a vector, such as a plasmid or viral vector, into which a nucleic acid molecule of the invention has been inserted, in a forward or reverse orientation. In a preferred aspect of this embodiment, the construct further comprises regulatory sequences, including, for example, a promoter operably linked to the sequence. Large numbers of suitable vectors and promoters are known to those of skill in the art and are commercially available. Appropriate cloning and expression vectors for use with prokaryotic and eukaryotic hosts are also described in Sambrook, et al.

A further aspect of the invention provides a cell comprising any of the polypeptide, polynucleotide or vector according to the invention. For example, a suitable cell may be a *Salmonella* cell, such as a *Salmonella enterica* cell, in some embodiments from the serovar *typhimurium*. The *Salmonella* may be an attenuated strain. Strains χ8914 and χ9241 may optionally be employed. For example, a suitable system is described in Kulkarni et al. (2008, Vaccine vol. 26, 4194-4203). Preferably the host cell is not a stem cell, especially not a human stem cell such as a human embryonic stem cell.

A further aspect of the invention provides an affinity reagent which is capable of binding to one of the polypeptides according to the first aspect of the invention and facilitating an immune response in the body of an individual to which the affinity reagent is administered. For example, the affinity reagent may be an antibody which may be a monoclonal antibody or a synthetic antibody, an Affibody® molecule or other antibody mimetic, an aptamer, a protein scaffold or a major histocompatibility complex (MHC) protein or portion thereof. The affinity reagent may be an antibody raised against a polypeptide according to the first aspect of the invention.

A further aspect of the invention provides a subunit or conjugate vaccine comprising a polypeptide according to the first aspect of the invention. For example, this may be in the form of a fusion protein and/or in the form of a recombinant viral vaccine.

A further aspect of the invention provides a method for the preparation of a vaccine, comprising adapting an Etx polypeptide or a vaccine or vaccine candidate comprising an Etx polypeptide by modifying domain III relative to wild type Etx polypeptide SEQ ID NO:65. A further aspect provides a vaccine composition prepared by a method comprising the aforementioned method.

The vaccine or vaccine candidate for improvement (by modification of domain III compared to a wild type polypeptide) may be selected from any of the following, which after modification of domain III show reduced toxicity compared to the original vaccine or candidate vaccine. For example, the following publications disclose polypeptides which have been shown to reduce toxicity towards MCDK cells and may be further improved by modifying domain III: Kang J et al. (2017) Hum Vaccin Immunother 13: 1598-1608 describes a proposed human vaccine with mutation F199 in domain 1; Yao et al. (2016) Sci Rep. 6: 24162 describes a Y196 mutation in domain 1; Li et al. (2013) Hum Vaccin Immunother 9: 2386-92 describes F199E and H106P mutants (F199 is in domain 1 and H106 is in domain 2); Oyston et al. (1998) Microbiology 144:333-41 describes a H106P mutant and also mentions H149P mutant as non-toxic (H106 is in domain 2); Dorca-Arevalo et al. (2014) PLoS One 9:e102417 describes V56C/F118C and H106P mutations as being non-toxic to MDCK cells (V56 is in domain 2 and F118 is in domain 2).

A further aspect provides an immunotherapy composition comprising a polypeptide, polynucleotide, vector, affinity reagent, subunit vaccine and/or conjugate vaccine according to preceding aspects of the invention, in a pharmaceutically acceptable formulation. For example, the immunotherapy composition may be a vaccine composition comprising a polypeptide according to the first aspect of the invention and an adjuvant. The composition may further comprise excipients and/or diluents appropriate for the means by which the composition is to be administered to a subject in need of treatment or vaccination against developing disease caused by *C. perfringens* and/or Etx. Selection of appropriate components is within the routine capability of the skilled person without the application of inventive activity.

For example, the immunotherapy composition of the invention may conveniently be formulated using a pharmaceutically acceptable excipient or diluent, such as, for example, an aqueous solvent, non-aqueous solvent, non-toxic excipient, such as a salt, preservative, buffer and the like. Examples of non-aqueous solvents are propylene glycol, polyethylene glycol, vegetable oil and injectable organic esters such as ethyloleate. Aqueous solvents include water, alcoholic/aqueous solutions, saline solutions, parenteral vehicles such as sodium chloride, Ringer's dextrose, etc. Preservatives include antimicrobial, anti-oxidants, chelating agents and inert gases. The pH and exact concentration of the various components the vaccine composition are adjusted according to routine skills.

Optionally, the immunotherapy formulation may include a carrier. Commonly used carrier molecules are bovine serum albumin (BSA), keyhole limpet hemocyanin (KLH), ovalbumin, mouse serum albumin, rabbit serum albumin and the like. Synthetic carriers may be used and are readily available. Means for conjugating peptides to carrier proteins are well known in the art and include glutaraldehyde, m-maleimidobenzoyl-N-hydroxysuccinimide ester, carbodiimide and bis-biazotized benzidine.

In certain situations, it may also be desirable to formulate the immunotherapy composition to comprise an adjuvant to enhance the immune response. Such adjuvants include all acceptable immunostimulatory compounds such as, for example, a cytokine, toxin, or synthetic composition. Commonly used adjuvants include aluminium hydroxide, aluminium phosphate, calcium phosphate, Freund's adjuvants and Quil-A saponin. An adjuvant provided by SEPPIC Inc (New Jersey, USA) as a Montanid™ adjuvant, for example Montanid™ ISA 61VG, may also be a suitable adjuvant. The inventors found that the use of Montanide™ ISA 61VG adjuvant resulted in the induction of better antibody responses compared to the use of an alhydrogel adjuvant. In addition to adjuvants, it may be desirable to co-administer biologic response modifiers (BRM) with the peptide or variant or derivative to down regulate suppressor T cell activity.

Possible vehicles for administration of the immunotherapy formulation include liposomes. Liposomes are microscopic vesicles that consist of one or more lipid bilayers surrounding aqueous compartments. Liposomes are similar in composition to cellular membranes and, as a result, liposomes generally can be administered safely and are biodegradable. Techniques for preparation of liposomes and the formulation (e.g., encapsulation) of various molecules, including peptides and oligonucleotides, with liposomes are well known.

Depending on the method of preparation, liposomes may be unilamellar or multilamellar and can vary in size with diameters ranging from 0.02 µm to greater than 10 µm. Liposomes can also adsorb to virtually any type of cell and then release the encapsulated agent. Alternatively, the liposome fuses with the target cell, whereby the contents of the liposome empty into the target cell. Alternatively, an absorbed liposome may be endocytosed by cells that are phagocytic. Endocytosis is followed by intralysosomal degradation of liposomal lipids and release of the encapsulated agents. In the present context, the polypeptide according to the invention can be localized on the surface of the liposome, to facilitate antigen presentation without disruption of the liposome or endocytosis. Irrespective of the mechanism or delivery, however, the result is the intracellular disposition of the associated polypeptide.

Liposomal vectors may be anionic or cationic. Anionic liposomal vectors include pH sensitive liposomes which disrupt or fuse with the endosomal membrane following endocytosis and endosome acidification. Cationic liposomes are preferred for mediating mammalian cell transfection in vitro, or general delivery of nucleic acids, but are used for delivery of other therapeutics, such as peptides.

Other suitable liposomes that are used in the methods of the invention include multilamellar vesicles (MLV), oligolamellar vesicles (OLV), unilamellar vesicles (UV), small unilamellar vesicles (SUV), medium-sized unilamellar vesicles (MIN), large unilamellar vesicles (LUV), giant unilamellar vesicles (GUV), multivesicular vesicles (MVV), single or oligolamellar vesicles made by reverse-phase evaporation method (REV), multilamellar vesicles made by the reverse-phase evaporation method (MLV-REV), stable plurilamellar vesicles (SPLV), frozen and thawed MLV (FATMLV), vesicles prepared by extrusion methods (VET), vesicles prepared by French press (FPV), vesicles prepared by fusion (FUV), dehydration-rehydration vesicles (DRV), and bubblesomes (BSV). Techniques for preparing these liposomes are well known in the art.

Other forms of delivery particle, for example, microspheres and the like, also are contemplated for delivery of the peptide epitopes or polyepitopes.

Alternatively, nucleic acid-based vaccines may be produced that comprise nucleic acid, such as, for example, DNA or RNA, encoding the immunologically active peptide epitope or polyepitope and cloned into a suitable vector (e.g., vaccinia, canarypox, adenovirus, or other eukaryotic virus vector).

Alternatively, the polypeptide may be administered in the form of a cellular vaccine via the administration of autologous or allogeneic APCs or dendritic cells that have been treated in vitro so as to present the peptide on their surface. *Salmonella enterica* or *Escherichia coli* strains harbouring mutations which reduce their virulence and allow them to colonise a host animal without causing disease might be used to deliver vaccine antigens, especially for administration to non-human animals. The bacteria used might include strains which are already used as vaccine in livestock where the attenuating lesion is not fully characterised. In addition, strains in which mutations have been deliberately introduced into the bacterium to rationally attenuate virulence could be used to deliver the polypeptide, as described in WO2013/144636. The antigen might also be delivered as a naked DNA vaccine where the gene encoding the epsilon toxoid is cloned into a mammalian expression vector and expressed from a eukaryotic promoter.

One of the most widely studied classes of attenuated *Salmonella* used as carriers of foreign antigens are auxotrophs. For example, genetically defined mutants of the aroA gene, encoding 5-enolpyruvylshikimate-3-phosphate synthase, have been constructed in both *S. enterica* var. *Typhimurium* and var. *Typhi*. These mutants are attenuated and immunogenic in mice. Examples of other auxotrophic mutants include *Salmonella* with deletions in the genes involved in the purine biosynthetic pathway. Another well-studied group of attenuated *Salmonella* are mutants that have defined deletions in genes involved in the regulation of *Salmonella* virulence. For example, mutations in genes encoding adenylate cyclase (cya) and camp receptor protein (crp) affect the expression of genes involved.

In one embodiment, the immunotherapy composition may be included in a foodstuff (i.e., a food material suitable for consumption by a human or an animal) comprising a polypeptide and/or a polynucleotide and/or a vector and/or a cell and/or a subunit vaccine and/or vaccine composition according to preceding aspects of the invention. This may, in non-limiting examples, be in the form of pellets, crumbs or a mash which may further comprise, again for example only, grain, grass and/or protein components. The composition may also be included in drinking liquids and/or administered via a spray into the atmosphere surrounding the animal which is, consequently, inhaled by the animal.

If the vaccine composition is for administration to a human subject, it may be in a form suitable for administration orally (e.g. in a dietary supplement) and/or parenterally, for example, by injection, inhalation, or by transdermal administration via a patch, lotion or gel. The particular forms outlined above are also generally useful for administration to a human subject.

A polypeptide, polynucleotide, vector, subunit vaccine, conjugate vaccine, antibody, affinity reagent, vaccine composition and/or immunotherapy composition according to the invention may be for use in a method of treating or vaccinating a subject against developing a disease caused by *Clostridium perfringens* and/or Etx, the disease for example involving accumulation in the subject's bloodstream of epsilon toxin which may be released by *C. perfringens*, particularly active epsilon toxin lacking the N- and C-termini of the full length prototoxin and/or for use in treating or vaccinating a subject against a condition associated with demyelination. A polypeptide, polynucleotide, vector, subunit vaccine, conjugate vaccine, affinity reagent, vaccine composition and/or immunotherapy composition according to the invention may be for use in a method of treatment or vaccinating a subject against developing a disease associated with infection by *Clostridium perfringens* or associated with the presence of Etx or condition associated with demyelination. According to one embodiment, the disease is enterotoxemia or a demyelinating disease, such as multiple sclerosis, neuromyelitis optica (NMO), optic neuritis (ON) or myelitis.

The invention also provides a method of vaccinating a subject against developing a disease caused by *Clostridium perfringens* and/or caused by the epsilon toxin, especially the active toxin; or associated with infection by *Clostridium perfringens* or associated with the presence of Etx or a condition associated with demyelination, the method comprising administering to a subject a polypeptide, polypeptide, polynucleotide, vector, subunit vaccine, conjugate vaccine, affinity reagent, vaccine composition and/or immunotherapy reagent according to the invention (for example, in a protective amount). The subject may be a human or a non-human animal. The non-human animal may be a horse or ruminant animal, such as a sheep, pig or goat, or a bovine animal such as a domestic cow or a companion animal, such as a dog, cat or rabbit. Young animals, such as lambs, piglets, kids and calves are also included.

A "protective amount" is an amount sufficient to induce an immune response in the subject, such that the probability of the subject developing a disease caused by *C. perfringens*, for example caused by (or associated with the presence of) epsilon toxin, especially active toxin, is reduced or removed. For example, antibodies capable of binding to SEQ ID NO:65 and/or 14 may be detectable after the administration, where such antibodies were not detectable prior to the administration, or only detectable at lower concentrations than after administration.

The invention also provides a kit comprising a polypeptide, polynucleotide, vector, subunit vaccine, conjugate vaccine, affinity reagent, vaccine composition and/or immunotherapy reagent according to the invention, the kit having uses, for example, in methods of treatment or vaccinating a subject against developing a disease caused by infection with *Clostridium perfringens* and/or Etx; or in methods of treatment or vaccinating a subject against developing a disease associated with infection by *Clostridium perfringens* or associated with the presence of Etx or a condition associated with demyelination. The kit may comprise means for administering the polypeptide, polynucleotide, vector, subunit vaccine, conjugate vaccine, affinity reagent, vaccine composition and/or immunotherapy reagent to an individual. For example, the kit may comprise one or more buffer reagents or diluents and/or one or more administration devices such as a syringe or other injection device. The kit may alternatively or additionally comprise instructions enabling a user to carry out a method of treatment or vaccinating a subject against developing a disease caused by or associated with *Clostridium perfringens* and/or Etx and/or a demyelinating disease, such as enterotoxemia (ET), multiple sclerosis (MS), clinically definite MS (CDMS), clinically isolated syndrome (CIS), neuromyelitis optica spectrum disorder (NMOSD), neuromyelitis optica (NMO), optic neuritis (ON), myelitis, transverse myelitis (TM), a disease or condition characterised by the increase or presence of antibodies against aquaporin-4 (AQP-4) and/or astrocyte damage, and acute disseminated encephalomyelitis (ADEM).

A disease caused by or associated with *Clostridium perfringens* and/or (active) epsilon toxin, as mentioned herein may be, for example, enterotoxemia including pre-disease symptoms such as systemic lesions and enterocolitis. Other symptoms may include oedema of the main target organs of the kidneys and brain and damage to vascular endothelial cells. The terminal phase of enterotoxaemia is characterized by severe neurological disorders that include opisthotonus, seizures and agonal struggling. The disease may be a demyelinating disease, such as multiple sclerosis (MS), clinically definite MS (CDMS), clinically isolated syndrome (CIS), neuromyelitis optica spectrum disorder (NMOSD), neuromyelitis optica (NMO), optic neuritis (ON), myelitis, transverse myelitis (TM), a disease or condition characterised by the increase or presence of antibodies against aquaporin-4 (AQP-4) and/or astrocyte damage, and acute disseminated encephalomyelitis (ADEM).

Throughout the description and claims of this specification, the words "comprise" and "contain" and variations of the words, for example "comprising" and "comprises", mean "including but not limited to" and do not exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Preferred features of each aspect of the invention may be as described in connection with any of the other aspects.

Other features of the present invention will become apparent from the following examples. Generally speaking the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

BRIEF DESCRIPTION OF THE FIGURES

Embodiments of the invention will now be described, by way of example only, with reference to FIGS. 1-5 in which:

FIG. 1 is a schematic representation of recombinant epsilon protoxin (P-Etx), with a N-terminal PelB leader peptide in place of the 13 amino acids N-terminal peptide sequence and with a C-terminal His-tag to aid purification (the amino acid sequences around the processing sites are also shown);

FIG. 2 shows the Etx amino acid sequence with positions of the signal sequence (residues 1-32); N-terminal pro-peptide (residues 33-45); C-terminal pro-peptide (residues 305-328); and mutated residues Y30A (Y43); V72F; F92A; H129A; V166A, A168F; Y196A(Y209), with the original unmutated amino acids shown under the mutation position;

Figure 3A:
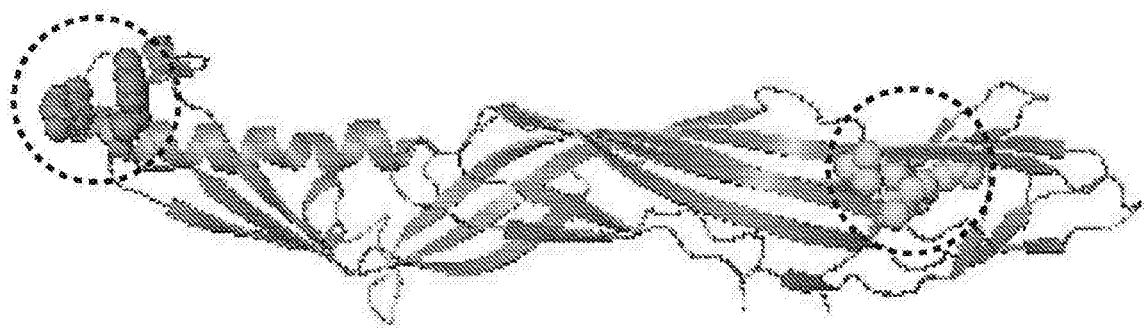
FIG. 3A shows 5 residues flanking a glycan (β-octyl-glucoside) binding site in domain III of Etx (a suggested second receptor binding site) identified for mutagenesis.
Figure 3B:
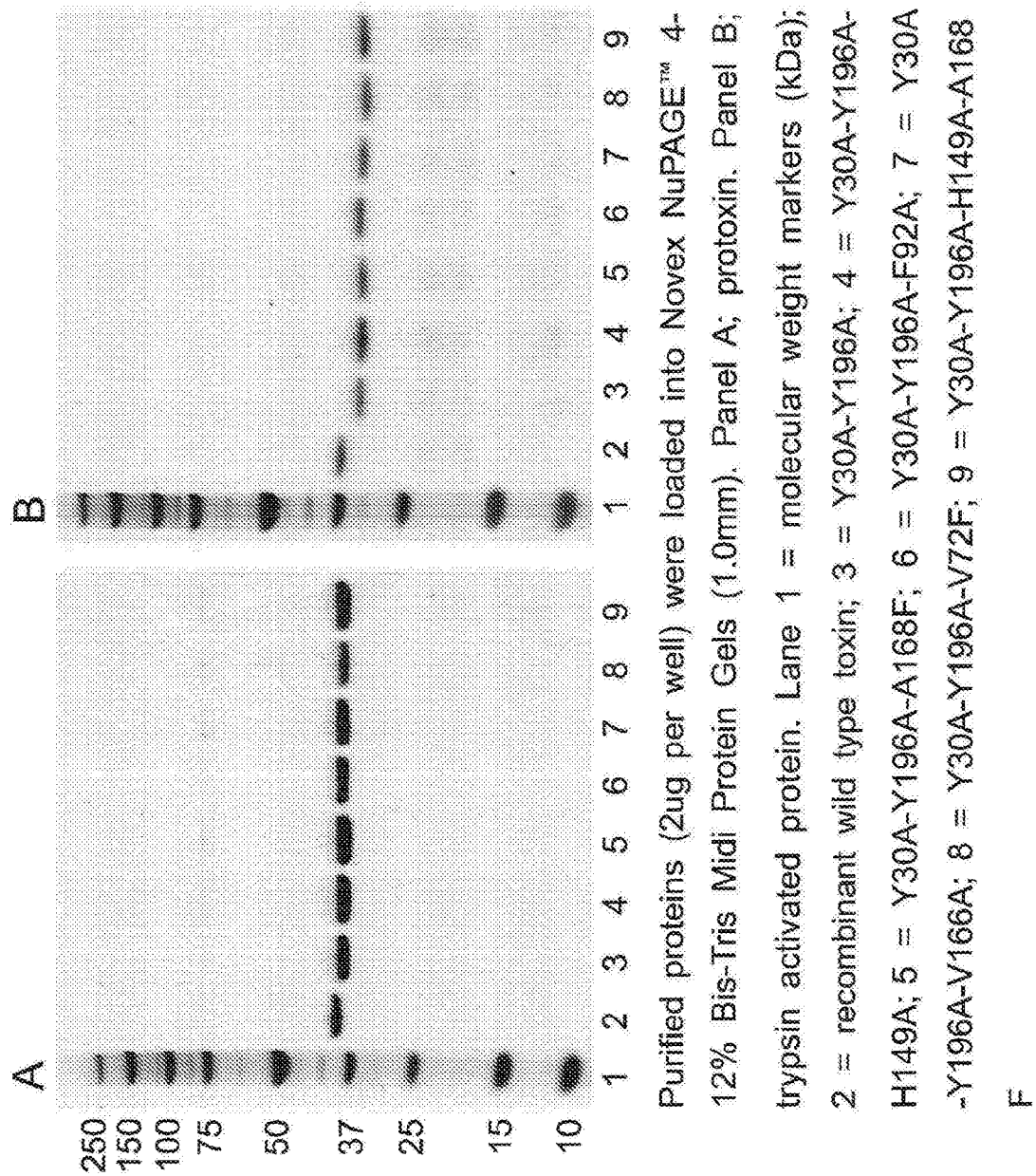
Figure 4:
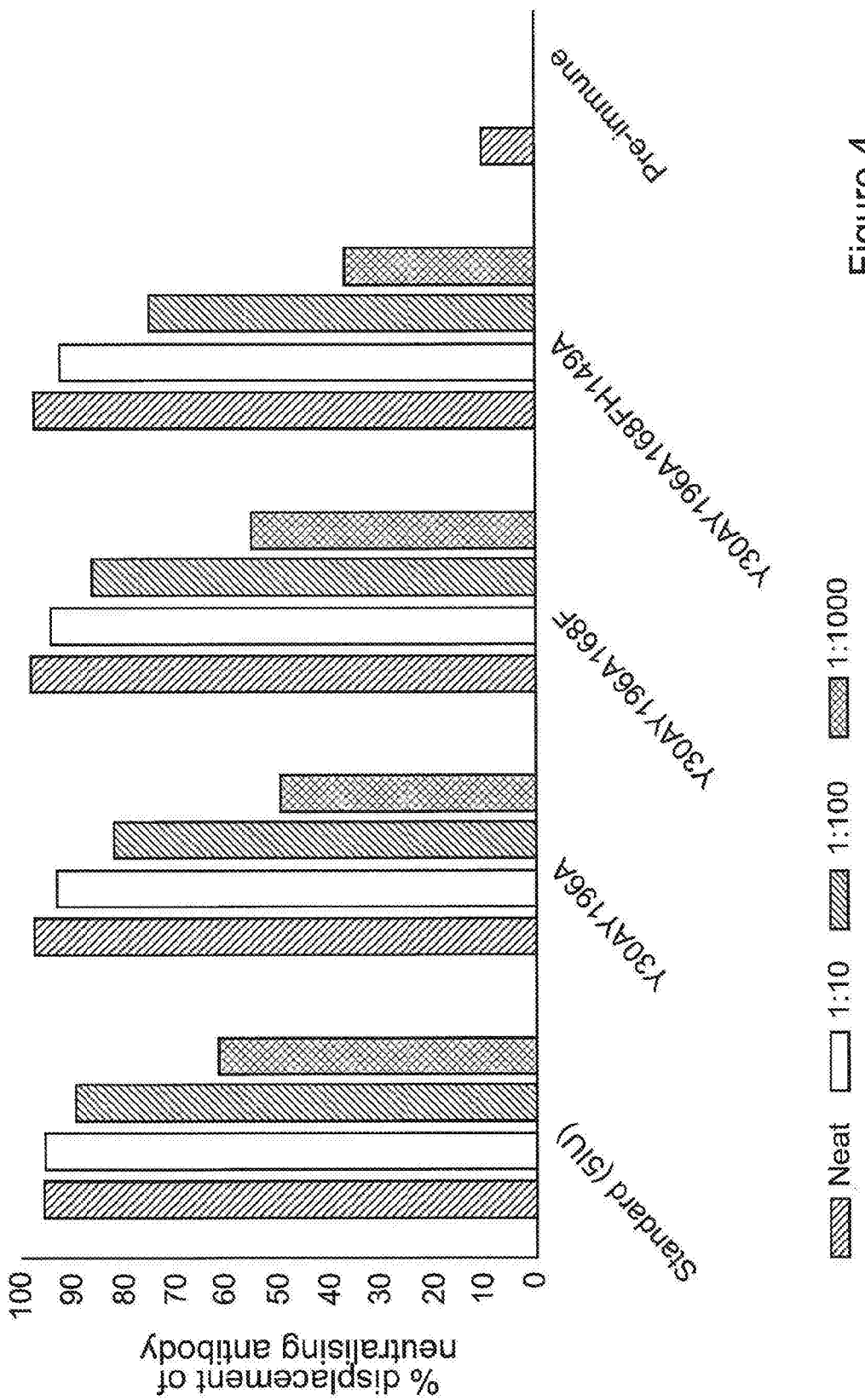

V72, F92, H149, V166, A168. Locations of residues previously mutated (shown in dark grey and circled (top); Y30 and Y196) and residues in the β-octyl-glucoside binding cleft (V72, F92, H149, V166, A168; shown in pale grey and circled (bottom);

FIG. 3B shows SDS-PAGE gel of purified proteins tested in this study. Using a plasmid which encoded the Y30A-Y196A variant form of Etx, additional mutations V72, F92, H149, V166 and A168 were introduced. These residues were mutated to alanine (H149, F92, V166) or phenylalanine (A168, V72) and the his-tagged proteins encoded by the mutated genes were expressed in *E. coli* and purified;

FIG. 4 shows the ability of WHO standard antitoxin (5 IU/ml) or rabbit sera raised against genetic toxoids, to displace binding of a neutralising monoclonal antibody in a competitive ELISA. The sera were diluted as indicated in the legend before testing. Data shown is the mean of two assays with SEM bars shown.

FIG. 5 shows the melting temperature (Tm) of wild type and variant proteins. Thermostability of Etx prototoxins was determined by the Boltzmann method using the Protein Thermal Shift software (Applied Biosystems). Results represent the mean and standard deviation of triplicate samples.

FIG. 6 show the results of the treatment of human red blood cells with epsilon toxin (wild type Etx; Y30AY196A; Y30AY196A+H149A; Y30AY196A+A168F; Y30AY196A+F92A; Y30AY196A+V166A, and a Quad: Y30AY196+A168F+H149A). Y30AY196A+A168F, Y30AY196A+H149A and the quad were not haemolytic even when trypsin activated.

ITEMS

The present invention will now be described with reference to the following items in which:

1. A method for preventing or treating a demyelinating condition selected from: enterotoxemia (ET), multiple sclerosis (MS), clinically definite MS (CDMS), clinically isolated syndrome (CIS), neuromyelitis optica spectrum disorder (NMOSD), optic neuritis (ON), neuromyelitis optica (NMO), myelitis, transverse myelitis (TM), a disease or condition characterised by the increase or presence of antibodies against aquaporin-4 (AQP-4) and/or astrocyte damage, and acute disseminated encephalomyelitis (ADEM) in a human or animal subject in need, comprising: administering to said subject a composition comprising an effective amount of an agent that directly or indirectly interferes with epsilon toxin (Etx) produced by *Clostridium perfringens* type B or type D bacterial strain, an Etx-binding receptor, or an interaction of Etx with its binding receptor so as to inhibit or suppress Etx modulated receptor signalling activities.
2. Method of item 1, wherein said agent is an inhibitor of Etx, such as an antibody or a functional component thereof.
3. Method of item 1, wherein said agent is an inhibitor or antagonist of an Etx-binding receptor.
4. Method of item 3, wherein said Etx-binding receptor is myelin and lymphocyte protein (MAL) or the hepatitis A virus cell receptor 1 proteins (HAVCR1).
5. Method of item 1, wherein said agent is a vaccine against *Clostridium perfringens* type B or type D bacterial strain, or the epsilon toxin (Etx) produced therefrom.
6. Method according to any preceding item, wherein said agent and comprises an epsilon toxin (Etx) polypeptide having reduced toxicity to cells expressing Myelin And Lymphocyte (MAL) protein and comprising a modified domain III compared to wild type Etx polypeptide SEQ ID NO:65, wherein said reduced toxicity is relative to SEQ ID NO: 65 and/or SEQ ID NO: 14 and wherein said Etx polypeptide is capable of binding at least one antibody which binds to a sequence represented by SEQ ID NO:65 and/or SEQ ID NO:14.
7. Method of item 6, wherein said modified domain III is a modification in the glycan (β-octyl-glucoside) binding site of domain III.
8. Method according to item 6 or 7, wherein said modified domain III comprises one or more mutations of the amino acids within the amino acid sequences making up domain III as represented by SEQ ID NOs 1, 2 and 3.
9. Method according to any one of items 6 to 8, comprising one or more of the following: SEQ ID NO: 10, SEQ ID NO: 6, SEQ ID NO: 7, SEQ ID NO: 8 and SEQ ID NO: 9.
10. Method according to any one of items 6 to 9, comprising SEQ ID NO: 4 and/or SEQ ID NO: 5 and/or SEQ ID NO: 6.
11. Method according to any one of items 6 to 10, comprising at least the following sequences:
    i) SEQ ID NO: 4 and SEQ ID NO: 5;
    and optionally in addition to (i)
    ii) SEQ ID NO: 6;
    and
    iii) one or more of the following: SEQ ID NO:10, SEQ ID NO:7, SEQ ID NO:8 and SEQ ID NO:9.
12. Method according to any one of items 6 to 11, wherein said reduced toxicity is reduced compared to an Etx polypeptide comprising SEQ ID NO: 4 and SEQ ID NO: 5; or an Etx polypeptide comprising SEQ ID NO: 4, SEQ ID NO: 5 and SEQ ID NO: 6; or compared to a known Etx vaccine or Etx vaccine candidate.
13. Method according to any one of items 6 to 12 having at least 60% sequence identity to any one of SEQ ID NOs 18 to 50 and comprising or consisting of the mutation(s) indicated in Table 3 for the relevant SEQ ID NO.
14. A polynucleotide having a nucleic acid sequence which encodes for a polypeptide according to any preceding items.
15. A vector comprising a polynucleotide according to item 14 or an agent according to any of items 1-5.
16. A cell comprising an agent according to any of items 1-5, a polypeptide according to any of items 6-13 and/or a polynucleotide according to item 14 and/or a vector according to item 15.
17. A subunit or conjugate vaccine comprising an agent according to any one of items 1-5, a polypeptide according to any of item 6-13.
18. An affinity reagent which is capable of binding to an agent according to any of items 1-5, one of the polypeptides according to any of items 6-13 and facilitating an immune response in the body of an individual to which the affinity reagent is administered.
19. A method for the preparation of an immunotherapy composition, optionally a vaccine composition, comprising adapting an Etx polypeptide or a vaccine comprising an Etx polypeptide by modifying domain III relative to a wild type Etx polypeptide.
20. An immunotherapy or vaccine composition prepared by a method according to item 19.

21. An immunotherapy or vaccine composition comprising an agent according to any of items 1-5, a polypeptide according to any of item 6-13 and/or a polynucleotide according to item 14 and/or a vector according to item 15 and/or a cell according to item 16 and/or a subunit vaccine according to item 17 and/or affinity reagent according to item 14.

22. An immunotherapy composition, optionally a vaccine composition, according to item 20 or 21 which is a foodstuff for a human or animal.

23. An agent according to any of items 1-5, a polypeptide according to any of items 6-13 and/or a polynucleotide according to item 14 and/or a vector according to item 15 and/or a cell according to item 16 and/or a subunit or conjugate vaccine according to item 17 and/or an affinity reagent according to item 18 and/or an immunotherapy or vaccine composition according to any one of item 20-22 for use in a method of treating or vaccinating a subject against developing a disease caused by or associated with *Clostridium perfringens* and/or caused by or associated with (active) epsilon toxin and/or against a demyelinating disease.

24. A polypeptide according to item 23, wherein the disease is selected from enterotoxemia (ET), multiple sclerosis (MS), clinically definite MS (CDMS), clinically isolated syndrome (CIS), neuromyelitis optica spectrum disorder (NMOSD), optic neuritis (ON), neuromyelitis optica (NMO), myelitis, transverse myelitis (TM), a disease or condition characterised by the increase or presence of antibodies against aquaporin-4 (AQP-4) and/or astrocyte damage, and acute disseminated encephalomyelitis (ADEM).

25. A method of treating a subject having a disease caused by or associated with the presence of *Clostridium perfringens* and/or caused by or associated with the presence of (active) epsilon toxin and/or against a demyelinating disease, or a method for vaccinating a subject against developing such a disease, the method comprising administering to a subject an agent according to any of items 1-5, a polypeptide according to any of items 6-13 and/or a polynucleotide according to item 14 and/or a vector according to item 15 and/or a cell according to item 16 and/or a subunit vaccine according to item 17 and/or affinity reagent according to item 18 and/or a vaccine or immunotherapy composition according to any one of items 20-22, wherein the demyelinating condition is selected from: enterotoxemia (ET), multiple sclerosis (MS), clinically definite MS (CDMS), clinically isolated syndrome (CIS), neuromyelitis optica spectrum disorder (NMOSD), optic neuritis (ON), neuromyelitis optica (NMO), myelitis, transverse myelitis (TM), a disease or condition characterised by the increase or presence of antibodies against aquaporin-4 (AQP-4) and/or astrocyte damage, and acute disseminated encephalomyelitis (ADEM).

26. An agent, polypeptide, polynucleotide, vector, cell, affinity reagent, vaccine composition or immunotherapy composition according to any one of items 20-22, or a method according to item 25, wherein the subject is a ruminant animal, a horse, a companion animal or a human.

27. Use of MAL cells as a model in the testing for toxicity of epsilon vaccine candidates.

28. A kit comprising an agent according to any of items 1-5, polypeptide according to any of item 6-13 and/or a polynucleotide according to item 14 and/or a vector according to item 15 and/or a cell according to item 16 and/or a subunit vaccine according to item 17 and/or an affinity reagent according to item 18 and/or a vaccine or immunotherapy composition according to any one of items 20-22.

29. A polypeptide, polynucleotide, vector, cell, subunit vaccine, a conjugate vaccine, affinity reagent, vaccine composition or immunotherapy composition or method substantially as herein described.

Examples

Materials and Methods

Chemicals

All chemicals were obtained from Sigma Chemical Co. (St. Louis, MO) unless otherwise specified.

Expression and Purification of Recombinant Epsilon Toxin Wild Type and Mutants

The etxD gene, encoding epsilon prototoxin D from *C. perfringens* Type D strain NCTC 8346, was cloned into the expression vector pET-26b(+) (Merck, Darmstadt, Germany) with a N-terminal PelB leader peptide in place of the 13 amino acids N-terminal peptide sequence (residues KEISNTVSNEMSK) and with a C-terminal polyhistidine (6×His) tag to aid affinity purification of recombinant prototoxin (Bokori-Brown et al., (2013) Protein science: a publication of the Protein Society 22:650-9). Amino acid numbering corresponds to prototoxin without the 13 amino acid N-terminal peptide sequence. Mutations H149A, A168F, F92A, V166A and V72F (residues flanking the β-octyl-glucoside binding site) were introduced into the previously generated Y30A-Y196A mutant (Bokori-Brown et al. (2014) Vaccine 32:2682-7) using the QuickChange Lightning Site-Directed Mutagenesis Kit (Agilent Technologies, Inc. Santa Clara, US) according to the manufacturer's instructions (amino acid numbering corresponds to prototoxin without the 13 amino acids N-terminal peptide sequence). Primers used for site-directed mutagenesis are shown in Table 4 below. Recombinant proteins were expressed in *E. coli* Rosetta 2 (DE3) cells (Merck, Darmstadt, Germany) and grown in ZYM-5052 auto-induction medium (Studier FW (2005) Protein expression and purification 41:207-34) supplemented with 50 µg/mL kanamycin and 34 µg/mL chloramphenicol. Cells (100 mL) were grown at 37° C. for 3 h and cultured for a further 24 h at 20° C., 300 rpm.

TABLE 4

PRIMERS USED FOR SITE DIRECTED MUTAGENESIS

| Amino acid change | SEQ ID NO | Primer sequence[a] |
|---|---|---|
| Y30A | 51 | PRIMER 'Y43A_FORWARD': GAAAGGAAGATATAATACAAAATATAATTACTTAAAGAGAATGGAAAAATATGCGCCTAATGCTATGGCATATTTTGATAAGG |
|  | 52 | PRIMER 'Y43A_REVERSE': CCTTATCAAAATATGCCATAGCATTAGGCGCATATTTTTCCATTCTCTTTAAGTAATTATATTTTGTATTATATCTTCCTTTC |

TABLE 4-continued

| PRIMERS USED FOR SITE DIRECTED MUTAGENESIS | | |
|---|---|---|
| Amino acid change | SEQ ID NO | Primer sequence[a] |
| Y196A | 53 | PRIMER 'Y209A_FORWARD': GTGAATGGGGAGAGATACCTAGTGCGTTAGCTTTTCCTAGGGATGGTTA |
| | 54 | PRIMER 'Y209A_REVERSE': TAACCATCCCTAGGAAAAGCTAACGCACTAGGTATCTCTCCCCATTCAC |
| H149A | 55 | PRIMER 'H149A_FORWARD': CAAATACAAATACAAATACTAATTCAAAAGAAATTACTGCTAATGTCCCTTCACAAGATATACTA |
| | 56 | PRIMER 'H149A_REVERSE': TAGTATATCTTGTGAAGGGACATTAGCAGTAATTTCTTTTGAATTAGTATTTGTATTTGTATTTG |
| V72F | 57 | PRIMER 'V72F_FORWARD': AGAACCATCAATGAATTATCTTGAAGATGTTTATTTTGGAAAAGCTCTCTTAAC |
| | 58 | PRIMER 'V72F_REVERSE': GTTAAGAGAGCTTTTCCAAAATAAACATCTTCAAGATAATTCATTGATGGTTCT |
| F92A | 59 | PRIMER 'F92A_FORWARD': TCTTAACTAATGATACTCAACAAGAACAAAAATTAAAATCACAATCAGCGACTTGTAAAAATACTGATACAGTAAC |
| | 60 | PRIMER 'F92A_REVERSE': GTTACTGTATCAGTATTTTTACAAGTCGCTGATTGTGATTTTAATTTTTGTTCTTGTTGAGTATCATTAGTTAAGA |
| V166A | 61 | PRIMER 'V166A_FORWARD': ATACTAGTACCAGCTAATACTACTGTAGAAGCGATAGCATATTTAAAAAAAGTTAATGTTAAAG |
| | 62 | PRIMER 'V166A_REVERSE': CTTTAACATTAACTTTTTTTAAATATGCTATCGCTTCTACAGTAGTATTAGCTGGTACTAGTAT |
| A168F | 63 | PRIMER 'A168F_FORWARD': GATATACTAGTACCAGCTAATACTACTGTAGAAGTAATATTTTATTTAAAAAAAGTTAATGTTAAAGGAAATGTAAAGTTAG |
| | 64 | PRIMER 'A168F_REVERSE': CTAACTTTACATTTCCTTTAACATTAACTTTTTTTAAATAAAATATTACTTCTACAGTAGTATTAGCTGGTACTAGTATATC |

[a]Underlined bases are the codons used for substitution. All primer sequences are shown in 5' to 3' orientation. Amino acid numbering corresponds to prototoxin without the N-terminal peptide sequence.

Protein Purification

For protein purification, cells were harvested by centrifugation, lysed enzymatically using BugBuster™ Protein Extraction Reagent (Merck, Darmstadt, Germany), and Y30A-Y196A and its derivatives were purified by Ni-NTA chromatography columns (GE Healthcare Life Sciences, Little Chalfont, UK) according to the manufacturer's instructions. For buffer exchange and further sample clean up, prototoxin containing eluate was applied to a PD-10 Desalting Column (GE Healthcare Life Sciences, Little Chalfont, UK) and eluted in 10 mM phosphate buffer, 2.7 mM potassium chloride, 137 mM NaCl, pH 7.4. Protein concentrations were determined using the BCA assay (Fisher Scientific UK Ltd, Loughborough, UK).

For studies in mice, rabbits or sheep the proteins were treated to remove endotoxin using a commercially available kit containing a high capacity endotoxin removal resin (Pierce™ High Capacity Endotoxin Removal Spin Columns, Thermo Scientific) according to the manufacturer's instructions. Residual levels of endotoxin were measured using a quantitative chromogenic assay (Pierce LAL Chromogenic Endotoxin Quantitation kit, Thermo Scientific).

Trypsin Activation

Purified recombinant epsilon prototoxin and its derivatives were activated with trypsin, TPCK treated from bovine pancreas (Sigma-Aldrich Company Ltd., Gillingham, UK), which removes the C-terminal peptide sequence. Trypsin was prepared in PBS and added to recombinant P-Etx at 1:100 (w/w) ratio and incubated at room temperature for 1 h. Protease Inhibitor Cocktail, EDTA-Free (Fisher Scientific UK Ltd, Loughborough, UK) was added to the digest to inhibit trypsin in the samples. Removal of the C-terminal peptide sequence was assessed by SDS-PAGE.

SDS-PAGE Analyses

Protein purity was analysed by SDS-PAGE on 4-12% Bis-Tris NuPAGE gels (Invitrogen Ltd., Paisley, UK) using XCell SureLock™ Mini-Cell Electrophoresis System (Invitrogen Ltd., Paisley, UK) and NuPAGE MES SDS running buffer (Invitrogen Ltd., Paisley, UK). All samples were heated prior to loading at 70° C. for 10 min in NuPAGE LDS sample buffer (Invitrogen Ltd., Paisley, UK). Gels were typically run at 200 V for 45 min. After electrophoretic separation, proteins were visualized by SimplyBlue staining (Invitrogen Ltd., Paisley, UK). The Perfect Protein molecular weight standard (Merck, Darmstadt, Germany) was used as marker.

Thermostability Assay

Thermostability was assessed by mixing purified protein (0.25 mg/mL) with 240×SYPRO Orange protein gel stain (Sigma-Aldrich Company Ltd., UK). Fluorescence was monitored using a StepOnePlus quantitative PCR machine (Applied Biosystems, USA) with a 1% thermal gradient from 25° C. to 99° C. The fluorescence data obtained was analysed using the Protein Thermal Shift Software (Applied Biosystems, USA) to calculate the melting temperature (Tm) using the Boltzmann method. All measurements were performed in triplicate.

Cell Culture

MDCK.2 cells (ATCC-LGC Standards, Teddington, UK) and ACHN cells (ECACC, Salisbury, UK) were routinely cultured in Eagle's Minimum Essential Medium (EMEM; ATCC-LGC Standards, Teddington, UK) supplemented with 10% Foetal Bovine Serum Gold (PAA, Pasching, Austria) at 37° C. in a humidified atmosphere of 95% air/5% $CO_2$. The culture medium was replaced every 2-3 days. Cells were routinely detached by incubation in trypsin/EDTA and split as appropriate (typically 1:6 dilutions).

Chinese hamster ovary (CHO) cells or CHO cells expressing green fluorescent protein (GFP)-tagged Human MAL (CHO-hMAL), sheep MAL (CHO-sMAL) or dog MAL (CHO-dMAL) were routinely cultured in Dulbecco's Modified Eagle's Medium/Ham's F12 (DMEM/F12) medium (Life Technologies) supplemented with 10% Foetal Bovine Serum at 37° C. in a humidified atmosphere of 95% air/5% $CO_2$. The culture medium was replaced every 2-3 days. Cells were routinely detached by incubation in trypsin/EDTA and split as appropriate (typically 1:6 dilutions).

Cytotoxicity Assay

The cytotoxic activity of trypsin-activated toxins toward MDCK.2 cells was determined by measuring the amount of lactate dehydrogenase (LDH) released from the cytosol of lysed cells into the cell culture medium using the CytoTox 96 nonradioactive cytotoxicity assay kit (Promega UK, Southampton, UK) according to the manufacturer's protocol. In brief, a two-fold dilution series of each activated toxin (ranging from 10 μM to 0.15 nM) was prepared in PBS and added to cells seeded into 96-well plate ($3 \times 10^4$ cells/well). Following incubation at 37° C. for 3 h, cell culture medium (50 μL) was harvested from cell monolayers, transferred to a fresh 96-well enzymatic assay plate and 50 μL of reconstituted substrate mix was added to each well. The plate was incubated for 30 min at room temperature, protected from light. Absorbance was read at 490 nm using a Model 680 Microplate Reader (Bio-Rad). The absorbance values for each sample were normalized by subtracting the absorbance value obtained for the culture medium from untreated cells. The toxin dose required to kill 50% of the cell monolayer ($CT_{50}$) was determined by nonlinear regression analysis (GraphPad). All experiments were performed in triplicates with three technical replicates each.

Immunisation of Rabbits

Groups of three New Zealand White rabbits were each immunized subcutaneously with 100 ug of Y30A-Y196A, Y30A-Y196A-A168F or Y30A-Y196A-H149A-A168F by Cambridge Research Biochemicals. Freund's Complete adjuvant was used for the initial immunisation and Freund's Incomplete adjuvant was use for 4 subsequent immunisations given at 14 day intervals. Blood was collected 7 days after booster dose 3 (day 49) and 7 days after booster dose 4 (day 63).

WHO International Standard *C. perfringens* epsilon horse antitoxin serum (CPEPAT) was obtained from the National Institute for Biological Standards and Control (NIBSC, South Mimms, UK).

Immunisation of Sheep with Y30AY196A+A168F Toxoid

Lambs were reared without vaccination against *C. perfringens* epsilon toxin and tested at intervals for the presence of antibody against epsilon toxin using Western blotting. After 12 months one group of 5 lambs received nothing, one group of 6 lambs received 200 μg of Y30AY196A+A168F toxoid adjuvanted (1:1) with Montanide™ ISA 61VG (Seppic, Paris, France), and a group of 5 lambs received 200 μg of the Y30AY196A+A168F toxoid adjuvanted with aluminium hydroxide gel (alhydrogel; Sigma-Aldrich, Poole UK; 0.25% w/v final concentration) adjuvant. We also immunised a group of 4 lambs, which had significant levels of pre-existing reactivity with epsilon toxin, with 200 μg of the Y30AY196A+A168F toxoid mixed with Montanide™ ISA 61VG adjuvant (1:1). All of the adjuvanted mixtures were given subcutaneously (s.c.) as 6×0.5 ml doses. Three weeks later the lambs were given a second dose of the adjuvanted protein. Blood samples were taken at the start of the study and at weeks 3, 7 and 12. Lamb immunisations were carried out by Orygen Antibodies Ltd, Penicuik, Scotland).

Competition ELISA Assay for Measuring Neutralising Antibodies

A competitive ELISA to measure neutralising antibodies was carried out using a Monoscreen ELISA kit (BioX Diagnostics, BIO K 222/2), according to the manufacturers' instructions. Absorbance was read at 450 nm and inhibition calculated using the following formula:

% inhibition sample=[($OD_{450\ nm}$ negative sera−OD sample)/$OD_{450\ nm}$ negative sera]×100

% inhibition positive=[($OD_{450\ nm}$ negative sera−OD positive sera)/$OO_{450\ nm}$ negative sera]×100

The test was validated only if the OD negative−OD positive was greater than 0.7 and inhibition of the positive control was greater than 30%.

Neutralisation of Toxicity Towards Cell Cultures

CHO cells expressing Human MAL were seeded at $3 \times 10^4$ cells per well of a 96 well plate and left to settle overnight. Rabbit sera from neat and a standard epsilon antitoxin (National Institute of Biological Standards and Control) from 20 IU/ml were diluted in a series of doubling dilutions in DPBS and incubated with an equal volume of trypsin activated wild type epsilon toxin ($5 \times CT_{50}$) for an hour at room temperature. The CHO hMAL cells were washed twice with serum free DMEM/F12 and the toxin:antibody/standard antitoxin mix was then added, along with DPBS only and toxin only controls ($5 \times CT_{50}$). Following incubation for 3 hours at 37° C. in a humidified atmosphere, the media was replaced with 100 μls of fresh serum free DMEM/F12 and 10 μl of WST-1 cell proliferation reagent (Abcam). The absorbance at 420 nm was read after incubation for 1 hour at 37° C. in a humidified atmosphere.

Toxicity in Mice

Groups of six female BALB/c mice were challenged by the intraperitoneal (i.p.) or subcutaneous (s.c.) route with either un-activated or trypsin-activated protein 100 W volumes. The experiments were was terminated at 24 hours post i.p. challenge or 7 days post s.c. challenge. The studies were performed with the approval of the on-site animal ethics committee. At intervals the animals were assessed for neurological symptoms, changes in appearance or changes in behaviour according to a pre-determined scoring matrix. Animals with a combined score of 5 or more were culled.

Results

Mutagenesis of Residues Flanking the β-Octyl-Glucoside Binding Site

In a previous study the inventors identified a glycan (β-octyl-glucoside) binding site in domain III of Etx and suggested that this site may be a second receptor binding site (Bokori-Brown (2013)). In this study, 5 residues flanking this site were identified for mutagenesis (V72, F92, H149, V166, A168; FIG. 3a) to evaluate their role in toxicity. Using a plasmid which encoded the Y30A-Y196A variant form of Etx, additional mutations in V72, F92, H149, V166 and A168 were introduced. These residues were mutated to alanine (H149, F92, V166) or phenylalanine (A168, V72) and the his-tagged proteins encoded by the mutated genes were expressed in E. coli and purified. Also expressed and purified was the Y30A-Y196A variant form of Etx and a mutant which contained both H149A and A168A in addition to Y30A-Y196A. The authenticity of the proteins was verified in two ways. First, the genes encoding the mutant genes were sequenced to validate the presence of the expected mutation. Secondly, the purified proteins were analysed by mass spectrometry to confirm that the experimentally determined mass matched the expected molecular mass of the protein. For studies in mice, rabbits or sheep the proteins had endotoxin levels below 1 endotoxin units (EU)/ml for mice and rabbits, and below 40 (EU)/ml for sheep.

Thermostability of Proteins

The structural stability of the wild type Epsilon toxin, the Y30A-Y196A variant protein and the 4 mutants of Y30A-Y196A were assessed using a thermostability assay. This revealed that the melting temperature (Tm in ° C.) of the Y30A-Y196A was lower than that of wild type toxin. However, the introduction of additional mutations (V72, F92, H149, V166 and A168) into the Y30A-Y196A variant protein only resulted in small changes in the thermostability of the proteins (FIG. 5) indicating that these substitutions did not destabilise the tertiary structures of the protein. The Y30A-Y196A-H149A-A168F has the lowest melting temperature, indicating that this was the least stable of the mutants tested.

Toxicity of the Variant Proteins in Cell Culture

The trypsin activated purified Etx proteins were tested for toxicity towards MDCK.2 cells, CHO cells and CHO cells expressing hMAL, sMAL or dMAL (Table 5). As previously found, the Y30AY196A mutations resulted in over 400-fold reduction in toxicity towards MDCK cells. However, this mutant showed 57-fold increased toxicity towards CHO cells expressing hMAL, 12-fold reduction in toxicity towards CHO cells expressing sMAL and 180 fold reduction in toxicity towards CHO cells expressing dMAL, all compared with wild type toxin. The additional introduction of the H149A, A168F, F92A or V72F mutations into the β-octyl-glucoside binding site reduced toxicity towards CHO-cells expressing hMAL.

TABLE 5

TOXICITY OF THE VARIANT ETX PROTEINS TESTED

| Mutant | Toxicity towards MDCK cells | Toxicity (activated Epsilon toxin) in mice (i.p.) | Toxicity (non-activated Epsilon toxin) in mice (s.c.) | Toxicity towards CHO-cell expressing human MAL | Toxicity towards CHO-cell expressing sheep MAL | Toxicity towards CHO-cell expressing dog MAL |
|---|---|---|---|---|---|---|
| Wild type toxin | 3.47 nM | 20 ng-200 ng | ND | 12.7 nM ± 0.68 nM | 1.6 nM ± 0.5 nM | 1.7 nM |
| Y30AY196A | 1.49 μM | 2 μg-20 μg | ND | 5.5 nM ± 0.43 nM | 13.75 nM ± 0.98 nM | 305 nM |
| Y30AY196A + H149A | >3 μM | 2 μg-20 μg | ND | >3 μM | >2 μM | TBD |
| Y30AY196A + A168F | >3 μM | >20 μg | >200 μg | >3 μM | >3.0 μM | 1.5 μM |
| Y30AY196A + F92A | 3 μM | ND | ND | >3 μM | 52.9 nM ± 17.0 nM | TBD |
| Y30AY196A + V166A | <3 μM | ND | ND | 14.6 nM ± 1.4 nM | 76.3 nM ± 11.0 nM | TBD |
| Y30AY196A + V72F | <3 μM | <2 μg | ND | >3 μM | TBD | TBD |
| Y30AY196A + H149A + A168F | >3 μM | >20 μg | ND | TBD | >3 μM | 788 nM |

Toxicity of the Variant Proteins in Mice

Variant proteins that had reduced toxicity in CHO-hMAL cell cultures (Y30A-Y196A-H149A, Y30A-Y196A-A168F and Y30A-Y196A-H149A-A168F) were tested for toxicity in mice (Table 5). When given by the i.p. route the MLD dose of trypsin-activated Y30A-Y196A-H149A was between 2 µg and 20 µg whereas the MLD dose of trypsin-activated Y30A-Y196A-A168F or Y30A-Y196A-H149A-A168F was above the highest dose tested (20 µg). The Y30A-Y196A-A168F protein was selected for further testing for toxicity by the s.c. route, either before or after trypsin activation. The MLD doses of the trypsin activated protein was between 20 µg and 200 µg, whereas the non-activated protein was not toxic at the doses tested.

Antibody Responses to the Variant Proteins

Groups of 3 rabbits were immunised with the Y30A-Y196A, Y30A-Y196A-A168F or Y30A-Y196A-H149A-A168F genetic toxoids given with Freund's incomplete adjuvant. This work was carried out by Cambridge Research Biochemicals (Cleveland, UK). One week after the fourth immunising dose, sera was tested for antibodies able to displace a neutralising monoclonal antibody against epsilon toxin, which indicated the presence of neutralising antibodies in the sera. For comparison we included WHO International Standard Epsilon toxin antitoxin, diluted to 5 IU/ml. The results indicated that all of the rabbits had developed antibodies which reacted with wild type epsilon toxin when tested using competition ELISA. The titres were broadly similar in the sera from individual rabbits in each immunisation group, and we therefore pooled the sera for subsequent tests.

We found that undiluted sera or sera diluted 10-fold in PBS were similar to each other and to the International Standard Epsilon toxin antitoxin in their abilities to displace the neutralising antibody. When diluted 100-fold, the sera raised against Y30A-Y196A, Y30A-Y196A-A168F and Y30A-Y196A-H149A-A168F were all more potent in displacing the neutralising antibody than the International Standard epsilon toxin antitoxin (FIG. 4).

Immunisation of Lambs

We immunised groups of 5 or 6 lambs with 2 doses of Y30A-Y196A-A168F prototoxin given with either Montanide™ ISA 61VG or alhydrogel adjuvant (Table 6). One additional group of lambs had pre-existing antibodies against epsilon toxin at the start of the study, detected using Western blotting, and these lambs were immunised with 2 doses of Y30A-Y196A-A168F protein with Montanide™ ISA 61VG adjuvant. The sera from these animals and control sera from lambs which had not been immunised were tested for the presence of antibody able to neutralise epsilon toxin using two different assays. First, we used a competition ELISA to measure the ability of the lamb sera to displace a neutralising monoclonal antibody. We also tested the ability of the sera to neutralise toxicity of epsilon toxin towards CHO-hMAL cells. In both of these assays we included dilutions of standardised sera containing a known concentration of neutralising antibody, expressed as international units (IU/ml).

We did not detect antibody in the control lambs using either assay. Using the competition ELISA we detected low levels of antibody in the group immunised with toxoid and alhydrogel adjuvant, but using the CHO-hMAL assay we could not detect any neutralising antibody. In contrast, lambs immunised with toxoid in Montanide™ ISA 61VG adjuvant developed high levels of neutralising antibody in both assays, in excess of 64 IU/ml in the CHO-hMAL assay and 200 IU/ml in the competition ELISA assay (Table 6). Lambs that were immunised with toxoid in Montanide™ ISA 61VG adjuvant but had pre-existing antibodies against epsilon toxin developed lower levels of neutralising antibodies after immunisation relative to lambs immunised with toxoid in Montanide™ ISA 61VG adjuvant that had no pre-existing antibodies against epsilon toxin.

TABLE 6

NEUTRALISING ANTIBODY IN LAMBS IMMUNISED WITH Y30A-Y196A-A168F

| Treatment Group | Neutralising antibody (IU/ml) measured using competition ELISA assay | Neutralising antibody (IU/ml) measured using CHO-hMal cells | Neutralising antibody (IU/ml) measured using CHO-sMal cells |
|---|---|---|---|
| Control | 0 | 0 | 0 |
| Y30A-Y196A-A168F + Montanide ™ ISA 61VG adjuvant | 200 IU/ml | >64 IU/ml | >160 IU/ml |
| Y30A-Y196A-A168F + alhydrogel adjuvant | 12.5 IU/ml | 0 | 0 |
| Y30A-Y196A-A168F + Montanide ™ ISA 61VG adjuvant (lambs with pre-existing antibodies to epsilon toxin) | 25 IU/ml | >8 IU/ml | >40 IU/ml | hMAL = human MAL
sMAL = sheep MAL

Discussion

In a previous study, the inventors investigated the potential of a site-directed mutant of Etx with mutations in the putative receptor binding domain (domain 1) and showed that a combination of Y30A and Y196A mutations markedly reduced the ability of the toxin to bind to and kill MDCK cells. The inventors also previously showed that Y30A-Y196A had reduced toxicity in mice, suggesting that Y30A-Y196A mutant could form the basis of an improved recombinant vaccine against enterotoxemia. Polyclonal antibody raised against Y30A-Y196A provided protection against wild type toxin in an in vitro neutralisation assay.

The previous study however used the MDCK cell line to measure cytotoxicity, and subsequently it has been shown that CHO cell expressing MAL are also highly sensitive to the toxin. The possibility that MAL is a receptor for the toxin is supported by the finding that MAL knockout mice become resistant to the effects of Etx. In the present study forming the basis of this application, it was found that the Y30A-Y196A mutant is only marginally less toxic towards CHO cells expressing sheep MAL, and is more toxic to CHO cells expressing human MAL compared to wild type Etx. However, in CHO cells expressing dog MAL the mutant is markedly less toxic. This finding suggests that MAL from different species interacts differently with Etx, indicating that in future studies MDCK cells as well as CHO cells expressing MAL should both be used in parallel.

The inventors introduced additional mutations to reduce the toxicity of Y30A-Y196A towards CHO cells expressing MAL. The mutations were introduced into a region in domain 3 that has been implicated in sugar binding. A number of these mutants showed reduced toxicity in CHO-hMAL cell cultures and also towards MDCK cells and in mice. The data confirm the role of this region in toxicity. The inventors were able to produce all of these proteins and on the basis of thermostability measurement they did not appear to show major changes in stability, suggesting that the conformation of the proteins was broadly similar to that of the wild type epsilon toxin. The Y30AY196A+A168F mutant was selected for testing in sheep because it induced robust antibody responses in rabbits.

Livestock vaccines containing aluminium hydroxide or saponin as adjuvants often induce short-lived antibody responses (Khorasani et al., (2016) Iranian journal of veterinary research 17: 8-12). This necessitates boosting at intervals, sometimes as short as 4 months apart. Montanide™ ISA 61 VG is a new ready-to-use mineral oil-based adjuvant for use in livestock which offers the potential to induce high level and long-lasting responses in animals (Khorasani et al., (2016)). The finding that the use of Montanide™ ISA 61VG adjuvant resulted in the induction of better antibody responses compared to the use of an alhydrogel adjuvant is similar to previous finding with a foot and mouth disease vaccine (Khorasani et al., (2016)). A previous report has also shown that ISA 61VG is superior to ISA 201 VG (water-in-oil) adjuvant or Montanide™ Gel 01 (aqueous polymer) adjuvant for the induction of antibody responses (Petermann et al., (2017) Exp Appl Acarol. 72:303-315). No evidence of local side effects after using Montanide™ ISA 61VG adjuvanted protein in lambs was seen, although others have reported evidence of local side effects using this adjuvant (Petermann et al., (2017) Exp Appl Acarol. 72:303-315). For licensing of epsilon-toxoid vaccine in Europe, compliance with the European Pharmacopoeia (Ph. Eur.) monograph on *Clostridium perfringens* vaccines for veterinary use (0363) would be required. The toxoid generated shows residual toxicity which is lower than that required, and the levels of neutralising antibody that we have achieved using Montanide™ ISA 61VG adjuvant is at least 10 times the threshold required of 5 U/ml.

The finding here that lambs with pre-existing antibodies against epsilon toxin responded less well to vaccination is in line with studies in other species. For example, antibodies inhibit responses to a broad range of vaccines (Voysey et al., (2017) JAMA paediatrics 171:637-46; Edwards et al., (2015) Vaccine 33:6469-72; Idoko et al., (2014) Vaccine 32:4220-7; Zarnitsyna et al., (2016) PLoS Pathog. 12:e1005692). These pre-existing antibodies might result in clearance of the antigen or the formation of antigen-antibody complexes limiting B cell activation or by physically masking the epitope from B cells (Zarnitsyna et al., (2016)).

The vaccine devised here would be used in livestock susceptible to enterotoxaemia caused by *C. perfringens* epsilon toxin. It would have a number of advantages over existing vaccines because it does not require de-toxification before use. The purity of the antigen and use of an adjuvant such as Montanide™ ISA 61VG should promote long term immunity, reducing or eliminating the need for booster immunisations. In addition, it could serve as a protein carrier for polysaccharides which induce protective antibodies against other diseases of livestock (Petermann et al., (2017) Exp Appl Acarol. 72:303-315; Voysey et al., (2017); Edwards et al., (2015) Idoko et al., (2014); Zarnitsyna et al., (2016); Byrd et al., (1992) Veterinary immunology and immunopathology 34:307-24). A glycoconjugate would promote T-cell responses to the polysaccharide moiety (Avci et al., (2011) Nature medicine 17:1602-9) with increases in the magnitude of the antibody response and the induction of memory responses to the polysaccharide (Avci (2013) Current Topics in Medicinal Chemistry 13:2535-40); Pace (2013) Expert opinion on biological therapy 13:11-33). In addition, the linking of the polysaccharide to the epsilon toxin carrier would allow the vaccine to be used in young animals (Pace (2013)). The Y30AY196A+A168F protein could be chemically coupled to polysaccharides or it could be further modified to serve as an acceptor for recombinant glycoconjugates generated by exploiting the naturally occurring glycosylation systems in bacteria (Valguarnera et al., (2016) J Mol Biol. 428:3206-20; Cuccui et al., (2015) The Journal of pharmacy and pharmacology 67:338-50.

Finally, the Y30AY196A+A168F protein could in the future be exploited as a vaccine for use in humans. *C. perfringens* epsilon toxin has been suggested to be a potential biothreat agent (Greenfield et al., (2002) Am J Med Sci. 323:326-40;

Berger et al., (2016) Disaster and military medicine 2:7), and vaccination of at risk individuals would protect them from disease. In addition, epsilon toxin has recently been implicated as playing a role in the development of multiple sclerosis (Rumah et al., (2013) PLoS One 8:e76359; Rumah et al., (2015) PLoS Pathog. 11:e1004896; Linden et al., (2015) mBio. 6). Should this link be established then vaccination to protect against the toxin could be a potential preventative or therapeutic option.

Longevity of the Protective Antibody Response

Lambs were reared without vaccination against *C. perfringens* epsilon toxin and after 12 months one group of 5 lambs received 200 μg of Y30AY196A+A168F toxoid adjuvanted (1:1) with Montanide ISA 61VG (Seppic, Paris, France) given subcutaneously (s.c.) as 6×0.5 ml doses. Three weeks later the lambs were given a second dose of the adjuvanted protein. Blood samples were taken at the start of the study and at intervals up to 12 months post immunisation. A competitive ELISA to measure neutralising antibodies was carried out using a Monoscreen ELISA kit (BioX Diagnostics, BIO K 222/2), according to the manufacturers' instructions. We included dilutions of standardised sera containing a known concentration of neutralising antibody, expressed as international units (IU/ml) to enable us to calculate the antibody level expressed as IU/l of neutralising antibody. The results are shown below in Table 7.

TABLE 7

Neutralising antibody in the sera after immunisation with Y30AY196A + A168F adjuvanted with Montanide ISA 61VG at week 0 and week 3

| | Weeks post first immunisation | | | | | | |
|---|---|---|---|---|---|---|---|
| | 3 | 7 | 13 | 16 | 25 | 38 | 52 |
| neutralising antibody (IU/ml) | 107 | 311 | 231 | 207 | 146 | 85 | 68 |

The neutralising antibody titres found in sheep dosed with our toxoid with Montanide ISA 61VG adjuvant are well in excess of the reported minimum protective titres in sheep (0.1-0.3 IU/ml (de la Rosa et al. 1997 (J Amin Sci 75(9): 2328-2334); Uzal and Kelly 1998 (Veterinary Record 142 (26): 722-725); or in goats (1 IU/ml (Uzal, Bodero et al. 1998 (Vet Rec 143(17): 472-474), Uzal and Kelly 1998 (Veterinary Record 142(26): 722-725)) and were still above this threshold one year after immunisation. Additionally, neutralising antibody levels were in excess of the protective titres after one dose of our vaccine (i.e. at week 3) indicating that a single dose vaccine for use in livestock is achievable.

NMO, ON and TM Patient Sample Testing

Table 8 below shows Western blot data from samples taken from subjects with NMO, almost all of whom initially presented with ON and/or TM. 15 of the 30 samples (50%) show very strongly positive (3), strongly positive (2), positive (8) or weakly positive (2) reactivity towards Etx compared with controls, of which 2/25 (8%) were positive.

All subjects tested positive for AQP-4 antibodies and 11 of the 15 subjects who tested positive for Etx initially showed features of Transverse Myelitis (TM) and/or optic neuritis (ON), examples of neuromyelitis optica spectrum disorder (NMOSD).

TABLE 8

Western Blot Data

| NMO/ON/TM patient sample ID | Reactivity towards Etx by Western Blot | Age & gender Matched Control (from MS study) | Control Reactivity towards Etx by Western Blot (from MS study) |
|---|---|---|---|
| 1 | ++ | | |
| 2 | − | C1 | − |
| 3 | + | B8 | − |
| 4 | + | A1 | + |
| 5 | + | *B12* | − |
| 6 | − | A6/A7 | − |
| 7 | − | D6 | − |
| 8 | − | B7 | − |
| 9 | − | C1 | − |
| 10 | − | A6 | − |
| 11 | − | *C1* | − |
| 12 | − | B9/E3/E2 | − |
| 13 | + (very weak) | A1 | − |
| 14 | + | B7 | − |
| 15 | + | D6/D2/B2/D11 | − |
| 16 | − | | |
| 17 | + | C2 | − |

TABLE 8-continued

Western Blot Data

| NMO/ON/TM patient sample ID | Reactivity towards Etx by Western Blot | Age & gender Matched Control (from MS study) | Control Reactivity towards Etx by Western Blot (from MS study) |
|---|---|---|---|
| 18 | − | F2 | − |
| 19 | +++ | B1 | − |
| 20 | ++ | B1 | − |
| 21 | − | | |
| 22 | + | B1 | − |
| 23 | − | Exeter 19 | − |
| 24 | − | | |
| 25 | − | *B11* | + |
| 26 | + (very weak) | *C9* | − |
| 27 | +++ | C9/C10 | − |
| 28 | +++ | | |
| 29 | − | *B3* | − |
| 30 | + | B5 | − |
| TOTAL +ve | 15/30 (50%) | | 2/25 (8%) |

Controls in bold italics - Gender and age matched +/− 2 years

Treatment of Human Red Blood Cells (RBCs) with Epsilon Toxin

Human red blood cells were tested for haemolysis when exposed to wild type Etx; Y30AY196A; Y30AY196A+H149A; Y30AY196A+A168F; Y30AY196A+F92A; Y30AY196A+V166A, and a Quad: Y30AY196+A168F+H149A. The prototoxin at 10 μM was tested and trypsin activated toxin at 10 μM and 1 μM with 3.3% RBCs. Each toxin was tested in triplicate at each dose. Results are expressed with respect to 1% Tx100 control (resulting in 100% haemolysis); negative control=PBS. The results are shown in FIG. 6 and illustrate that Y30AY196A+H149A, Y30AY196A+A168F and Y30AY196+A168F+H149A are not haemolytic even when trypsin activated.

```
SEQUENCES (MUTATION POSITIONS SHOWN IN BOLD)

SEQ ID NO: 1
VYVGKALLTNDTQQEQKLKSQSFTCK

SEQ ID NO: 2
THNVPSQDILVPANTTVEVIAYLK

SEQ ID NO: 3
DELIVKVRNLNTNNVQEYVIPVDKKEKSNDSNIVKYRSLYIKAPGIK

SEQ ID NO: 4 Y30A mutation
RMEKYXPNAM

SEQ ID NO: 5 Y196A mutation
GEIPSXLAFP

SEQ ID NO: 6 H149A mutation
SKEITXNVPS

SEQ ID NO: 7 V72F mutation
LEDVYXGKAL

SEQ ID NO: 8 F92A mutation
LKSQSXTCKN

SEQ ID NO: 9 V166A mutation
NTTVEXIAYL

SEQ ID NO: 10 A168F mutation
TVEVIXYLKK
```

SEQUENCES (MUTATION POSITIONS SHOWN IN BOLD)

SEQ ID NO: 11 full length wild-type native epsilon toxin
MKKNLVKSLAIASAVISIYSIVNIVSPTNVIAKEISNTVSNEMSKKASYD
NVDTLIEKGRYNTKYNYLKRMEKYYPNAMAYFDKVTINPQGNDFYINNPK
VELDGEPSMNYLEDVYVGKALLTNDTQQEQKLKSQSFTCKNTDTVTATTT
HTVGTSIQATAKFTVPFNETGVSLTTSYSFANTNTNINSKEITHNVPSQD
ILVPANTTVEVIAYLKKVNVKGNVKLVGQVSGSEWGEIPSYLAFPRDGYK
FSLSDTVNKSDLNEDGTININGKGNYSAVMGDELIVKVRNLNTNNVQEYV
IPVDKKEKSNDSNIVKYRSLSIKAPGIK SEQ ID NO: 12 sequence used to obtain crystal structure
(PDB ID:1YUJ)
KEISNTVSNEMSKKASYDNVDTLIEKGRYNTKYNYLKRMEKYYPNAMAYF
DKVTINPQGNDFYINNPKVELDGEPSMNYLEDVYVGKALLINDTQQEQKL
KSQSFTCKNTDTVTATTTHTVGTSIQATAKFTVPFNETGVSLTTSYSFAN
TNTNTNSKEITHNVPSQDILVPANTTVEVIAYLKKVNVKGNVKLVGQVSG
SEWGEIPSYLAFPRDGYKFSLSDTVNKSDLNEDGTININGKGNYSAVMGD
ELIVKVRNLNTNNVQEYVIPVDKKEKSNDSNIVKYRSLSIKAPGIK SEQ ID NO: 13 trypsin activated wild-type recombinant
epsilon toxin
MGKASYDNVDTLIEKGRYNTKYNYLKRMEKYYPNAMAYFDKVTINPQGND
FYINNPKVELDGEPSMNYLEDVYVGKALLTNDTQQEQKLKSQSFTCKNTD
TVTATTTHTVGTSIQATAKFTVPFNETGVSLTTSYSFANTNTNTNSKEIT
HNVPSQDILVPANTTVEVIAYLKKVNVKGNVKLVGQVSGSEWGEIPSYLA
FPRDGYKFSLSDTVNKSDLNEDGTININGKGNYSAVMGDELIVKVRNLNT
NNVQEYVIPVDKK SEQ ID NO: 14 trypsin activated recombinant epsilon toxin
with H149A mutation
MGKASYDNVDTLIEKGRYNTKYNYLKRMEKYYPNAMAYFDKVTINPQGND
FYINNPKVELDGEPSMNYLEDVYVGKALLTNDTQQEQKLKSQSFTCKNTD
TVTATTTHTVGTSIQATAKFTVPFNETGVSLTTSYSFANTNTNTNSKEIT
ANVPSQDILVPANTTVEVIAYLKKVNVKGNVKLVGQVSGSEWGEIPSYLA
FPRDGYKFSLSDTVNKSDLNEDGTININGKGNYSAVMGDELIVKVRNLNT
NNVQEYVIPVDKK SEQ ID NO: 15 full length recombinant epsilon toxin
MKYLLPTAAAGLLLLAAQPAMAMGKASYDNVDTLIEKGRYNTKYNYLKRM
EKYYPNAMAYFDKVTINPQGNDFYINNPKVELDGEPSMNYLEDVYVGKAL
LTNDTQQEQKLKSQSFTCKNTDTVTATTTHTVGTSIQATAKFTVPFNETG
VSLTTSYSFANTNTNTNSKEITHNVPSQDILVPANTTVEVIAYLKKVNVK
GNVKLVGQVSGSEWGEIPSYLAFPRDGYKFSLSDTVNKSDLNEDGTININ
GKGNYSAVMGDELIVKVRNLNTNNVQEYVIPVDKKEKSNDSNIVKYRSLY
IKAPGIKLEHHHHHH SEQ ID NO: 16 trypsin activated recombinant epsilon toxin
(Y30A + Y196A)
MGKASYDNVDTLIEKGRYNTKYNYLKRMEKYAPNAMAYFDKVTINPQGND
FYINNPKVELDGEPSMNYLEDVYVGKALLTNDTQQEQKLKSQSFTCKNID
TVTATTTHTVGTSIQATAKFTVPFNETGVSLTTSYSFANTNTNTNSKEIT
HNVPSQDILVPANTTVEVIAYLKKVNVKGNVKLVGQVSGSEWGEIPSALA
FPRDGYKFSLSDTVNKSDLNEDGTININGKGNYSAVMGDELIVKVRNLNT
NNVQEYVIPVDKK SEQ ID NO: 17 trypsin activated recombinant epsilon toxin
(Y30A + Y196A + H149A)
MGKASYDNVDTLIEKGRYNTKYNYLKRMEKYAPNAMAYFDKVTINPQGND
FYINNPKVELDGEPSMNYLEDVYVGKALLTNDTQQEQKLKSQSFTCKNTD
TVTATTTHTVGTSIQATAKFTVPFNETGVSLTTSYSFANTNTNTNSKEIT
ANVPSQDILVPANTTVEVIAYLKKVNVKGNVKLVGQVSGSEWGEIPSALA
FPRDGYKFSLSDTVNKSDLNEDGTININGKGNYSAVMGDELIVKVRNLNT
NNVQEYVIPVDKK SEQ ID NO: 18 trypsin activated recombinant epsilon toxin
(Y30A + Y196A + V72F)
MGKASYDNVDTLIEKGRYNTKYNYLKRMEKYAPNAMAYFDKVTINPQGND
FYINNPKVELDGEPSMNYLEDVYFGKALLTNDTQQEQKLKSQSFTCKNTD
TVTATTTHTVGTSIQATAKFTVPFNETGVSLTTSYSFANTNTNTNSKEIT
HNVPSQDILVPANTTVEVIAYLKKVNVKGNVKLVGQVSGSEWGEIPSALA
FPRDGYKFSLSDTVNKSDLNEDGTININGKGNYSAVMGDELIVKVRNLNT
NNVQEYVIPVDKK SEQ ID NO: 19 trypsin activated recombinant epsilon toxin
(Y30A + Y196A + F92A)
MGKASYDNVDTLIEKGRYNTKYNYLKRMEKYAPNAMAYFDKVTINPQGND
FYINNPKVELDGEPSMNYLEDVYVGKALLTNDTQQEQKLKSQSATCKNTD
TVTATTTHTVGTSIQATAKFTVPFNETGVSLTTSYSFANTNTNTNSKEIT

| SEQUENCES (MUTATION POSITIONS SHOWN IN BOLD) |
|---|
| HNVPSQDILVPANTTVEVIAYLKKVNVKGNVKLVGQVSGSEWGEIPSALA<br>FPRDGYKFSLSDTVNKSDLNEDGTININGKGNYSAVMGDELIVKVRNLNT<br>NNVQEYVIPVDKK<br><br>SEQ ID NO: 20 trypsin activated recombinant epsilon toxin<br>(Y30A + Y196A + V166A)<br>MGKASYDNVDTLIEKGRYNTKYNYLKRMEKYAPNAMAYFDKVTINPQGND<br>FYINNPKVELDGEPSMNYLEDVYVGKALLTNDTQQEQKLKSQSFTCKNTD<br>TVTATTTHTVGTSIQATAKFTVPFNETGVSLTTSYSFANTNTNTNSKEIT<br>HNVPSQDILVPANTTVEAIAYLKKVNVKGNVKLVGQVSGSEWGEIPSALA<br>FPRDGYKFSLSDTVNKSDLNEDGTININGKGNYSAVMGDELIVKVRNLNT<br>NNVQEYVIPVDKK<br><br>SEQ ID NO: 21 trypsin activated recombinant epsilon toxin<br>(Y30A + Y196A + A168F)<br>MGKASYDNVDTLIEKGRYNTKYNYLKRMEKYAPNAMAYFDKVTINPQGND<br>FYINNPKVELDGEPSMNYLEDVYVGKALLTNDTQQEQKLKSQSFTCKNTD<br>TVTATTTHTVGTSIQATAKFTVPFNETGVSLTTSYSFANTNTNTNSKEIT<br>HNVPSQDILVPANTTVEVIFYLKKVNVKGNVKLVGQVSGSEWGEIPSALA<br>FPRDGYKFSLSDTVNKSDLNEDGTININGKGNYSAVMGDELIVKVRNLNT<br>NNVQEYVIPVDKK<br><br>SEQ ID NO: 22 trypsin activated recombinant epsilon toxin<br>(Y30A + Y196A + H149A + V72F)<br>MGKASYDNVDTLIEKGRYNTKYNYLKRMEKYAPNAMAYFDKVTINPQGND<br>FYINNPKVELDGEPSMNYLEDVYFGKALLTNDTQQEQKLKSQSFTCKNTD<br>TVTATTTHTVGTSIQATAKFTVPFNETGVSLTTSYSFANTNTNTNSKEIT<br>ANVPSQDILVPANTTVEVIAYLKKVNVKGNVKLVGQVSGSEWGEIPSALA<br>FPRDGYKFSLSDTVNKSDLNEDGTININGKGNYSAVMGDELIVKVRNLNT<br>NNVQEYVIPVDKK<br><br>SEQ ID NO: 23 trypsin activated recombinant epsilon toxin<br>(Y30A + Y196A + H149A + F92A)<br>MGKASYDNVDTLIEKGRYNTKYNYLKRMEKYAPNAMAYFDKVTINPQGND<br>FYINNPKVELDGEPSMNYLEDVYVGKALLTNDTQQEQKLKSQSATCKNTD<br>TVTATTTHTVGTSIQATAKFTVPFNETGVSLTTSYSFANTNTNTNSKEIT<br>ANVPSQDILVPANTTVEVIAYLKKVNVKGNVKLVGQVSGSEWGEIPSALA<br>FPRDGYKFSLSDTVNKSDLNEDGTININGKGNYSAVMGDELIVKVRNLNT<br>NNVQEYVIPVDKK<br><br>SEQ ID NO: 24 trypsin activated recombinant epsilon toxin<br>(Y30A + Y196A + H149A + V166A)<br>MGKASYDNVDTLIEKGRYNTKYNYLKRMEKYAPNAMAYFDKVTINPQGND<br>FYINNPKVELDGEPSMNYLEDVYVGKALLTNDTQQEQKLKSQSFTCKNTD<br>TVTATTTHTVGTSIQATAKFTVPFNETGVSLTTSYSFANTNTNTNSKEIT<br>ANVPSQDILVPANTTVEAIAYLKKVNVKGNVKLVGQVSGSEWGEIPSALA<br>FPRDGYKFSLSDTVNKSDLNEDGTININGKGNYSAVMGDELIVKVRNLNT<br>NNVQEYVIPVDKK<br><br>SEQ ID NO: 25 trypsin activated recombinant epsilon toxin<br>(Y30A + Y196A + H149A + A168F)<br>MGKASYDNVDTLIEKGRYNTKYNYLKRMEKYAPNAMAYFDKVTINPQGND<br>FYINNPKVELDGEPSMNYLEDVYVGKALLTNDTQQEQKLKSQSFTCKNTD<br>TVTATTTHTVGTSIQATAKFTVPFNETGVSLTTSYSFANTNTNTNSKEIT<br>ANVPSQDILVPANTTVEVIFYLKKVNVKGNVKLVGQVSGSEWGEIPSALA<br>FPRDGYKFSLSDTVNKSDLNEDGTININGKGNYSAVMGDELIVKVRNLNT<br>NNVQEYVIPVDKK<br><br>SEQ ID NO: 26 trypsin activated recombinant epsilon toxin<br>(Y30A + Y196A + V72F + F92A)<br>MGKASYDNVDTLIEKGRYNTKYNYLKRMEKYAPNAMAYFDKVTINPQGND<br>FYINNPKVELDGEPSMNYLEDVYFGKALLTNDTQQEQKLKSQSATCKNTD<br>TVTATTTHTVGTSIQATAKFTVPFNETGVSLTTSYSFANTNTNTNSKEIT<br>HNVPSQDILVPANTTVEVIAYLKKVNVKGNVKLVGQVSGSEWGEIPSALA<br>FPRDGYKFSLSDTVNKSDLNEDGTININGKGNYSAVMGDELIVKVRNLNT<br>NNVQEYVIPVDKK<br><br>SEQ ID NO: 27 trypsin activated recombinant epsilon toxin<br>(Y30A + Y196A + V72F + V166A)<br>MGKASYDNVDTLIEKGRYNTKYNYLKRMEKYAPNAMAYFDKVTINPQGND<br>FYINNPKVELDGEPSMNYLEDVYFGKALLTNDTQQEQKLKSQSFTCKNTD<br>TVTATTTHTVGTSIQATAKFTVPFNETGVSLTTSYSFANTNTNTNSKEIT<br>HNVPSQDILVPANTTVEAIAYLKKVNVKGNVKLVGQVSGSEWGEIPSALA<br>FPRDGYKFSLSDTVNKSDLNEDGTININGKGNYSAVMGDELIVKVRNLNT<br>NNVQEYVIPVDKK |

| SEQUENCES (MUTATION POSITIONS SHOWN IN BOLD) |
| --- |

SEQ ID NO: 28 trypsin activated recombinant epsilon toxin
(Y30A + Y196A + V72F + A168F)
MGKASYDNVDTLIEKGRYNTKYNYLKRMEKYAPNAMAYFDKVTINPQGND
FYINNPKVELDGEPSMNYLEDVYFGKALLTNDTQQEQKLKSQSFTCKNTD
TVTATTTHTVGTSIQATAKFTVPFNETGVSLTTSYSFANTNTNTNSKEIT
HNVPSQDILVPANTTVEVIFYLKKVNVKGNVKLVGQVSGSEWGEIPSALA
FPRDGYKFSLSDTVNKSDLNEDGTININGKGNYSAVMGDELIVKVRNLNT
NNVQEYVIPVDKK SEQ ID NO: 29 trypsin activated recombinant epsilon toxin
(Y30A + Y196A + F92A + V166A)
MGKASYDNVDTLIEKGRYNTKYNYLKRMEKYAPNAMAYFDKVTINPQGND
FYINNPKVELDGEPSMNYLEDVYVGKALLTNDTQQEQKLKSQSATCKNTD
TVTATTTHTVGTSIQATAKFTVPFNETGVSLTTSYSFANTNTNTNSKEIT
HNVPSQDILVPANTTVEAIAYLKKVNVKGNVKLVGQVSGSEWGEIPSALA
FPRDGYKFSLSDTVNKSDLNEDGTININGKGNYSAVMGDELIVKVRNLNT
NNVQEYVIPVDKK SEQ ID NO: 30 trypsin activated recombinant epsilon toxin
(Y30A + Y196A + F92A + A168F)
MGKASYDNVDTLIEKGRYNTKYNYLKRMEKYAPNAMAYFDKVTINPQGND
FYINNPKVELDGEPSMNYLEDVYVGKALLTNDTQQEQKLKSQSATCKNTD
TVTATTTHTVGTSIQATAKFTVPFNETGVSLTTSYSFANTNTNTNSKEIT
HNVPSQDILVPANTTVEVIFYLKKVNVKGNVKLVGQVSGSEWGEIPSALA
FPRDGYKFSLSDTVNKSDLNEDGTININGKGNYSAVMGDELIVKVRNLNT
NNVQEYVIPVDKK SEQ ID NO: 31 trypsin activated recombinant epsilon toxin
(Y30A + Y196A + V166A + A168F)
MGKASYDNVDTLIEKGRYNTKYNYLKRMEKYAPNAMAYFDKVTINPQGND
FYINNPKVELDGEPSMNYLEDVYVGKALLTNDTQQEQKLKSQSFTCKNTD
TVTATTTHTVGTSIQATAKFTVPFNETGVSLTTSYSFANTNTNTNSKEIT
HNVPSQDILVPANTTVRAIFYLKKVNVKGNVKLVGQVSGSEWGEIPSALA
FPRDGYKFSLSDTVNKSDLNEDGTININGKGNYSAVMGDELIVKVRNLNT
NNVQEYVIPVDKK SEQ ID NO: 32 trypsin activated recombinant epsilon toxin
(Y30A + Y196A + H149A + V72F + F92A)
MGKASYDNVDTLIEKGRYNTKYNYLKRMEKYAPNAMAYFDKVTINPQGND
FYINNPKVELDGEPSMNYLEDVYFGKALLTNDTQQEQKLKSQSATCKNTD
TVTATTTHTVGTSIQATAKFTVPFNETGVSLTTSYSFANTNTNTNSKEIT
ANVPSQDILVPANTTVEVIAYLKKVNVKGNVKLVGQVSGSEWGEIPSALA
FPRDGYKFSLSDTVNKSDLNEDGTININGKGNYSAVMGDELIVKVRNLNT
NNVQEYVIPVDKK SEQ ID NO: 33 trypsin activated recombinant epsilon toxin
(Y30A + Y196A + H149A + V72F + V166A)
MGKASYDNVDTLIEKGRYNTKYNYLKRMEKYAPNAMAYFDKVTINPQGND
FYINNPKVELDGEPSMNYLEDVYFGKALLTNDTQQEQKLKSQSFTCKNTD
TVTATTTHTVGTSIQATAKFTVPFNETGVSLTTSYSFANTNTNTNSKEIT
ANVPSQDILVPANTTVEAIAYLKKVNVKGNVKLVGQVSGSEWGEIPSALA
FPRDGYKFSLSDTVNKSDLNEDGTININGKGNYSAVMGDELIVKVRNLNT
NNVQEYVIPVDKK SEQ ID NO: 34 trypsin activated recombinant epsilon toxin
(Y30A + Y196A + H149A + V72F + A168F)
MGKASYDNVDTLIEKGRYNTKYNYLKRMEKYAPNAMAYFDKVTINPQGND
FYINNPKVELDGEPSMNYLEDVYFGKALLTNDTQQEQKLKSQSFTCKNTD
TVTATTTHTVGTSIQATAKFTVPFNETGVSLTTSYSFANTNTNTNSKEIT
ANVPSQDILVPANTTVEVIFYLKKVNVKGNVKLVGQVSGSEWGEIPSALA
FPRDGYKFSLSDTVNKSDLNEDGTININGKGNYSAVMGDELIVKVRNLNT
NNVQEYVIPVDKK SEQ ID NO: 35 trypsin activated recombinant epsilon toxin
(Y30A + Y196A + H149A + F92A + V166A)
MGKASYDNVDTLIEKGRYNTKYNYLKRMEKYAPNAMAYFDKVTINPQGND
FYINNPKVELDGEPSMNYLEDVYVGKALLTNDTQQEQKLKSQSATCKNTD
TVTATTTHTVGTSIQATAKFTVPFNETGVSLTTSYSFANTNTNTNSKEIT
ANVPSQDILVPANTTVEAIAYLKKVNVKGNVKLVGQVSGSEWGEIPSALA
FPRDGYKFSLSDTVNKSDLNEDGTININGKGNYSAVMGDELIVKVRNLNT
NNVQEYVIPVDKK SEQ ID NO: 36 trypsin activated recombinant epsilon toxin
(Y30A + Y196A + H149A + F92A + A168F)
MGKASYDNVDTLIEKGRYNTKYNYLKRMEKYAPNAMAYFDKVTINPQGND
FYINNPKVELDGEPSMNYLEDVYVGKALLTNDTQQEQKLKSQSATCKNTD

| SEQUENCES (MUTATION POSITIONS SHOWN IN BOLD) |
| --- |
| TVTATTTHTVGTSIQATAKFTVPFNETGVSLTTSYSFANTNTNTNSKEIT<br>ANVPSQDILVPANTTVEVIFYLKKVNVKGNVKLVGQVSGSEWGEIPSALA<br>FPRDGYKFSLSDTVNKSDLNEDGTININGKGNYSAVMGDELIVKVRNLNT<br>NNVQEYVIPVDKK<br><br>SEQ ID NO: 37 trypsin activated recombinant epsilon toxin<br>(Y30A + Y196A + H149A + Y166A + A168F)<br>MGKASYDNVDTLIEKGRYNTKYNYLKRMEKYAPNAMAYFDKVTINPQGND<br>FYINNPKVELDGEPSMNYLEDVYVGKALLTNDTQQEQKLKSQSFTCKNTD<br>TVTATTTHTVGTSIQATAKFTVPFNETGVSLTTSYSFANTNTNTNSKEIT<br>ANVPSQDILVPANTTVEAIFYLKKVNVKGNVKLVGQVSGSEWGEIPSALA<br>FPRDGYKFSLSDTVNKSDLNEDGTININGKGNYSAVMGDELIVKVRNLNT<br>NNVQEYVIPVDKK<br><br>SEQ ID NO: 38 trypsin activated recombinant epsilon toxin<br>(Y30A + Y196A + V72F + F92A + V166A)<br>MGKASYDNVDTLIEKGRYNTKYNYLKRMEKYAPNAMAYFDKVTINPQGND<br>FYINNPKVELDGEPSMNYLEDVYFGKALLTNDTQQEQKLKSQSATCKNTD<br>TVTATTTHTVGTSIQATAKFTVPFNETGVSLTTSYSFANTNTNTNSKEIT<br>HNVPSQDILVPANTTVEAIAYLKKVNVKGNVKLVGQVSGSEWGEIPSALA<br>FPRDGYKFSLSDTVNKSDLNEDGTININGKGNYSAVMGDELIVKVRNLNT<br>NNVQEYVIPVDKK<br><br>SEQ ID NO: 39 trypsin activated recombinant epsilon toxin<br>(Y30A + Y196A + V72F + F92A + A168F)<br>MGKASYDNVDTLIEKGRYNTKYNYLKRMEKYAPNAMAYFDKVTINPQGND<br>FYINNPKVELDGEPSMNYLEDVYFGKALLTNDTQQEQKLKSQSATCKNTD<br>TVTATTTHTVGTSIQATAKFTVPFNETGVSLTTSYSFANTNTNTNSKEIT<br>HNVPSQDILVPANTTVEVIFYLKKVNVKGNVKLVGQVSGSEWGEIPSALA<br>FPRDGYKFSLSDTVNKSDLNEDGTININGKGNYSAVMGDELIVKVRNLNT<br>NNVQEYVIPVDKK<br><br>SEQ ID NO: 40 trypsin activated recombinant epsilon toxin<br>(Y30A + Y196A + V72F + V166A + A168F)<br>MGKASYDNVDTLIEKGRYNTKYNYLKRMEKYAPNAMAYFDKVTINPQGND<br>FYINNPKVELDGEPSMNYLEDVYFGKALLTNDTQQEQKLKSQSFTCKNTD<br>TVTATTTHTVGTSIQATAKFTVPFNETGVSLTTSYSFANTNTNTNSKEIT<br>HNVPSQDILVPANTTVEAIFYLKKVNVKGNVKLVGQVSGSEWGEIPSALA<br>FPRDGYKFSLSDTVNKSDLNEDGTININGKGNYSAVMGDELIVKVRNLNT<br>NNVQEYVIPVDKK<br><br>SEQ ID NO: 41 trypsin activated recombinant epsilon toxin<br>(Y30A + Y196A + F92A + V166A + A168F)<br>MGKASYDNVDTLIEKGRYNTKYNYLKRMEKYAPNAMAYFDKVTINPQGND<br>FYINNPKVELDGEPSMNYLEDVYVGKALLTNDTQQEQKLKSQSATCKNTD<br>TVTATTTHTVGTSIQATAKFTVPFNETGVSLTTSYSFANTNTNTNSKEIT<br>HNVPSQDILVPANTTVRAIFYLKKVNVKGNVKLVGQVSGSEWGEIPSALA<br>FPRDGYKFSLSDTVNKSDLNEDGTININGKGNYSAVMGDELIVKVRNLNT<br>NNVQEYVIPVDKK<br><br>SEQ ID NO: 42 trypsin activated recombinant epsilon toxin<br>(Y30A + Y196A + H149A + V72F + F92A + V166A)<br>MGKASYDNVDTLIEKGRYNTKYNYLKRMEKYAPNAMAYFDKVTINPQGND<br>FYINNPKVELDGEPSMNYLEDVYFGKALLTNDTQQEQKLKSQSATCKNTD<br>TVTATTTHTVGTSIQATAKFTVPFNETGVSLTTSYSFANTNTNTNSKEIT<br>ANVPSQDILVPANTTVEAIAYLKKVNVKGNVKLVGQVSGSEWGEIPSALA<br>FPRDGYKFSLSDTVNKSDLNEDGTININGKGNYSAVMGDELIVKVRNLNT<br>NNVQEYVIPVDKK<br><br>SEQ ID NO: 43 trypsin activated recombinant epsilon toxin<br>(Y30A + Y196A + H149A + V72F + F92A + A168F)<br>MGKASYDNVDTLIEKGRYNTKYNYLKRMEKYAPNAMAYFDKVTINPQGND<br>FYINNPKVELDGEPSMNYLEDVYFGKALLTNDTQQEQKLKSQSATCKNTD<br>TVTATTTHTVGTSIQATAKFTVPFNETGVSLTTSYSFANTNTNTNSKEIT<br>ANVPSQDILVPANTTVEVIFYLKKVNVKGNVKLVGQVSGSEWGEIPSALA<br>FPRDGYKFSLSDTVNKSDLNEDGTININGKGNYSAVMGDELIVKVRNLNT<br>NNVQEYVIPVDKK<br><br>SEQ ID NO: 44 trypsin activated recombinant epsilon toxin<br>(Y30A + Y196A + V72F + F92A + V166A + A168F)<br>MGKASYDNVDTLIEKGRYNTKYNYLKRMEKYAPNAMAYFDKVTINPQGND<br>FYINNPKVELDGEPSMNYLEDVYFGKALLTNDTQQEQKLKSQSATCKNTD<br>TVTATTTHTVGTSIQATAKFTVPFNETGVSLTTSYSFANTNTNTNSKEIT<br>HNVPSQDILVPANTTVRAIFYLKKVNVKGNVKLVGQVSGSEWGEIPSALA<br>FPRDGYKFSLSDTVNKSDLNEDGTININGKGNYSAVMGDELIVKVRNLNT<br>NNVQEYVIPVDKK |

| SEQUENCES (MUTATION POSITIONS SHOWN IN BOLD) |
|---|
| SEQ ID NO: 45 trypsin activated recombinant epsilon toxin<br>(Y30A + Y196A + H149A + V72F + F92A + V166A + A168F)<br>MGKASYDNVDTLIEKGRYNTKYNYLKRMEKYAPNAMAYFDKVTINPQGND<br>FYINNPKVELDGEPSMNYLEDVYFGKALLTNDTQQEQKLKSQSATCKNTD<br>TVTATTTHTVGTSIQATAKFTVPFNETGVSLTTSYSFANTNTNTNSKEIT<br>ANVPSQDILVPANTTVEAIFYLKKVNVKGNVKLVGQVSGSEWGEIPSA**LA<br>FPRDGYKFSLSDTVNKSDLNEDGTININGKGNYSAVMGDELIVKVRNLNT<br>NNVQEYVIPVDKK |
| SEQ ID NO: 46 trypsin activated recombinant epsilon toxin<br>(V72F)<br>MGKASYDNVDTLIEKGRYNTKYNYLKRMEKYYPNAMAYFDKVTINPQGND<br>FYINNPKVELDGEPSMNYLEDVYFGKALLTNDTQQEQKLKSQSFTCKNTD<br>TVTATTTHTVGTSIQATAKFTVPFNETGVSLTTSYSFANTNTNTNSKEIT<br>HNVPSQDILVPANTTVEVIAYLKKVNVKGNVKLVGQVSGSEWGEIPSYLA<br>FPRDGYKFSLSDTVNKSDLNEDGTININGKGNYSAVMGDELIVKVRNLNT<br>NNVQEYVIPVDKK |
| SEQ ID NO: 47 trypsin activated recombinant epsilon toxin<br>(F92A)<br>MGKASYDNVDTLIEKGRYNTKYNYLKRMEKYYPNAMAYFDKVTINPQGND<br>FYINNPKVELDGEPSMNYLEDVYVGKALLTNDTQQEQKLKSQSATCKNTD<br>TVTATTTHTVGTSIQATAKFTVPFNETGVSLTTSYSFANTNTNTNSKEIT<br>HNVPSQDILVPANTTVEVIAYLKKVNVKGNVKLVGQVSGSEWGEIPSYLA<br>FPRDGYKFSLSDTVNKSDLNEDGTININGKGNYSAVMGDELIVKVRNLNT<br>NNVQEYVIPVDKK |
| SEQ ID NO: 48 trypsin activated type recombinant epsilon<br>toxin (H149A)<br>MGKASYDNVDTLIEKGRYNTKYNYLKRMEKYYPNAMAYFDKVTINPQGND<br>FYINNPKVELDGEPSMNYLEDVYVGKALLTNDTQQEQKLKSQSFTCKNTD<br>TVTATTTHTVGTSIQATAKFTVPFNETGVSLTTSYSFANTNTNTNSKEIT<br>ANVPSQDILVPANTTVEVIAYLKKVNVKGNVKLVGQVSGSEWGEIPSYLA<br>FPRDGYKFSLSDTVNKSDLNEDGTININGKGNYSAVMGDELIVKVRNLNT<br>NNVQEYVIPVDKK |
| SEQ ID NO: 49 trypsin activated recombinant epsilon toxin<br>(V166A)<br>MGKASYDNVDTLIEKGRYNTKYNYLKRMEKYYPNAMAYFDKVTINPQGND<br>FYINNPKVELDGEPSMNYLEDVYVGKALLTNDTQQEQKLKSQSFTCKNTD<br>TVTATTTHTVGTSIQATAKFTVPFNETGVSLTTSYSFANTNTNTNSKEIT<br>HNVPSQDILVPANTTVEAIAYLKKVNVKGNVKLVGQVSGSEWGEIPSYLA<br>FPRDGYKFSLSDTVNKSDLNEDGTININGKGNYSAVMGDELIVKVRNLNT<br>NNVQEYVIPVDKK |
| SEQ ID NO: 50 trypsin activated recombinant epsilon toxin<br>(A168F)<br>MGKASYDNVDTLIEKGRYNTKYNYLKRMEKYYPNAMAYFDKVTINPQGND<br>FYINNPKVELDGEPSMNYLEDVYVGKALLTNDTQQEQKLKSQSFTCKNTD<br>TVTATTTHTVGTSIQATAKFTVPFNETGVSLTTSYSFANTNTNTNSKEIT<br>HNVPSQDILVPANTTVEVIFYLKKVNVKGNVKLVGQVSGSEWGEIPSYLA<br>FPRDGYKFSLSDTVNKSDLNEDGTININGKGNYSAVMGDELIVKVRNLNT<br>NNVQEYVIPVDKK |
| SEQ ID NO: 51 Y43A FORWARD<br>GAAAGGAAGATATAATACAAAATATAATTACTTAAAGAGAATGGAAAAATATGCGCCTAATGCTATGGCATA<br>TTTTGATAAGG |
| SEQ ID NO: 52 Y43A REVERSE<br>CCTTATCAAAATATGCCATAGCATTAGGCGCATATTTTTCCATTCTCTTTAAGTAATTATATTTTGTATTAT<br>ATCTTCCTTTC |
| SEQ ID NO: 53 Y209A FORWARD<br>GTGAATGGGGAGAGATACCTAGTGCGTTAGCTTTTCCTAGGGATGGTTA |
| SEQ ID NO: 54 Y209A REVERSE<br>TAACCATCCCTAGGAAAAGCTAACGCACTAGGTATCTCTCCCCATTCAC |
| SEQ ID NO: 55 H149A FORWARD<br>CAAATACAAATACAAATACTAATTCAAAAGAAATTACTGCTAATGTCCCTTCACAAGATATACTA |
| SEQ ID NO: 56 H149A REVERSE<br>TAGTATATCTTGTGAAGGGACATTAGCAGTAATTTCTTTTGAATTAGTATTTGTATTTGTATTTG |
| SEQ ID NO: 57 V72F FORWARD<br>AGAACCATCAATGAATTATCTTGAAGATGTTTATTTTGGAAAAGCTCTCTTAAC |

| SEQUENCES (MUTATION POSITIONS SHOWN IN BOLD) |
|---|
| SEQ ID NO: 58 V72F REVERSE<br>GTTAAGAGAGCTTTTCCAAAATAAACATCTTCAAGATAATTCATTGATGGTTCT |
| SEQ ID NO: 59 F92A FORWARD<br>TCTTAACTAATGATACTCAACAAGAACAAAAATTAAAATCACAATCAGCGACTTGTAAAAATACTGATACAGTAAC |
| SEQ ID NO: 60 F92A REVERSE<br>GTTACTGTATCAGTATTTTTACAAGTCGCTGATTGTGATTTTAATTTTTGTTCTTGTTGAGTATCATTAGTTAAGA |
| SEQ ID NO: 61 V166A FORWARD<br>ATACTAGTACCAGCTAATACTACTGTAGAAGCGATAGCATATTTAAAAAAAGTTAATGTTAAAG |
| SEQ ID NO: 62 V166A REVERSE<br>CTTTAACATTAACTTTTTTTAAATATGCTATCGCTTCTACAGTAGTATTAGCTGGTACTAGTAT |
| SEQ ID NO: 63 A168F FORWARD<br>GATATACTAGTACCAGCTAATACTACTGTAGAAGTAATATTTTATTTAAAAAAAGTTAATGTTAAAGGAAATGTAAAGTTAG |
| SEQ ID NO: 64 A168F REVERSE<br>CTAACTTTACATTTCCTTTAACATTAACTTTTTTTAAATAAAATATTACTTCTACAGTAGTATTAGCTGGTACTAGTATATC |
| SEQ ID NO: 65 (FIG. 2 residues 1 to 260 of unmutated sequence; trypsin activated polypeptide)<br>KASYDNVDTL IEKGRYNTKY NYLKRMEKYY PNAMAYFDKV TINPQGNDFY<br>INNPKVELDG EPSMNYLEDV YVGKALLTND TQQEQKLKSQ SFTCKNTDTV<br>TATTTHTVGT SIQATAKFTV PFNETGVSLT TSYSFANTNT NTNSKEITHN<br>VPSQDILVPA NTTVEVIAYL KKVNVKGNVK LVGQVSGSEW GEIPSYLAFP<br>RDGYKFSLSD TVNKSDLNED GTININGKGN YSAVMGDELI VKVRNLNTNN<br>VQEYVIPVDK |
| SEQ ID NO: 66 (FIG. 2 signal sequence residues 1 to 32)<br>MKKNLVKSLAIASAVISIYSIVNIVSPTNVIA |
| SEQ ID NO: 67 (FIG. 2 N-terminal pro-peptide residues 33 to 45)<br>KEISNTVSNEMSK |
| SEQ ID NO: 68 (FIG. 2 C-terminal pro-peptide residues 305 to 328)<br>KEKSNDSNIVKYRSLYIKAPGIK |

The invention claimed is:

1. A *Clostridium perfringens* epsilon toxin (Etx) polypeptide having reduced toxicity to cells expressing Myelin And Lymphocyte (MAL) protein,
   wherein said Etx polypeptide comprises a Y30A mutation, a Y196A mutation, and an A168F mutation compared to wild type Etx polypeptide SEQ ID NO:65,
   wherein said reduced toxicity is relative to a Y30A-Y196A mutation,
   wherein said Etx polypeptide is capable of binding at least one antibody which binds to a sequence represented by SEQ ID NO: 65 and/or SEQ ID NO: 14, and
   wherein the Etx polypeptide comprises SEQ ID NO:21.

2. The Etx polypeptide of claim 1, wherein said ETX polypeptide further comprises one or more amino acid substitutions in the glycan (β-octyl-glucoside) binding site of domain III.

3. The Etx polypeptide of claim 2, wherein said substitutions are selected from: H149A, V72F, F92A, and V166A.

4. The Etx polypeptide of claim 1, wherein said reduced toxicity Etx polypeptide further comprises mutation(s) selected from the group consisting of:
   (a) H149X,
   (b) V72X,
   (c) F92X,
   (d) V166X,
   (e) V92X,
   (f) H149X, V72X,
   (g) H149X, F92X,
   (h) H149X, V166X,
   (i) V72X, F92X,
   (j) V72X, V166X,
   (k) V92X, V166X,
   (l) F92X, V166X, (m) H149X, V72X, F92X,
(n) H149X, V72X, V166X,
(o) H149X, F92X, V166X,
(p) V72X, F92X, V166X, and
(q) H149X, V72X, F92X, V166X,
  wherein the mutation positions are counted from residue 1 of SEQ ID NO:65, and
  wherein X is an amino acid differing from the amino acid shown proceeding the position number.

5. The Etx polypeptide of claim 4, wherein the further mutation(s) are selected from the group consisting of
(a) H149A,
(b) V72F,
(c) F92A,
(d) V166A,
(e) V92F,
(f) H149A, V72F,
(g) H149A, F92A,
(h) H149A, V166A,
(i) V72F, F92A,
(j) V72F, V166A,
(k) V92F, V166A,
(l) F92A, V166A,
(m) H149A, V72F, F92A,
(n) H149A, V72F, V166A,
(0) H149A, F92A, V166A,
(p) V72F, F92A, V166A, and
(q) H149A, V72F, F92A, V166A.

6. An immunotherapy or vaccine composition comprising the Etx polypeptide of claim 1.

7. An immunotherapy composition or a vaccine composition according to claim 6, wherein the immunotherapy composition or vaccine composition is a foodstuff for a human or animal.

8. An immunotherapy or vaccine composition comprising an Etx polypeptide having reduced toxicity to cells expressing Myelin And Lymphocyte (MAL) protein,
  wherein said Etx polypeptide comprises a Y30A mutation, a Y196A mutation, and an A168F mutation compared to wild type Etx polypeptide SEQ ID NO:65,
  wherein said reduced toxicity is relative to a Y30A-Y196A mutation,
  wherein said Etx polypeptide is capable of binding at least one antibody which binds to a sequence represented by SEQ ID NO: 65 and/or SEQ ID NO: 14, and
  wherein the Etx polypeptide comprises SEQ ID NO:21.

9. An immunotherapy or vaccine composition comprising an Etx polypeptide having reduced toxicity to cells expressing Myelin And Lymphocyte (MAL) protein,
  wherein said Etx polypeptide comprises a Y30A mutation, a Y196A mutation, an H149A mutation and an A168F mutation compared to wild type Etx polypeptide SEQ ID NO: 65,
  wherein said reduced toxicity is relative to a Y30A-Y196A mutation,
  wherein said Etx polypeptide is capable of binding at least one antibody which binds to a sequence represented by SEQ ID NO: 65 and/or SEQ ID NO: 14, and
  wherein the Etx polypeptide comprises SEQ ID NO:21.

* * * * *